US012748105B2

(12) United States Patent
Tateno

(10) Patent No.: US 12,748,105 B2

(45) Date of Patent: Sep. 29, 2026

(54) METHOD FOR ANALYZING GLYCAN

(71) Applicant: NATIONAL INSTITUTE OF ADVANCED INDUSTRIAL SCIENCE AND TECHNOLOGY, Tokyo (JP)

(72) Inventor: Hiroaki Tateno, Tsukuba (JP)

(73) Assignee: NATIONAL INSTITUTE OF ADVANCED INDUSTRIAL SCIENCE AND TECHNOLOGY (JP)

( * ) Notice: Subject to any disclaimer, the term of this patent is extended or adjusted under 35 U.S.C. 154(b) by 778 days.

(21) Appl. No.: 17/913,698

(22) PCT Filed: Mar. 15, 2021

(86) PCT No.: PCT/JP2021/010385

§ 371 (c)(1),
(2) Date: Sep. 22, 2022

(87) PCT Pub. No.: WO2021/193199

PCT Pub. Date: Sep. 30, 2021

(65) Prior Publication Data

US 2023/0117360 A1 Apr. 20, 2023

(30) Foreign Application Priority Data

Mar. 24, 2020 (JP) ................................ 2020-053296

(51) Int. Cl.

*C12Q 1/686* (2018.01)
*G01N 33/53* (2006.01)
*G01N 33/58* (2006.01)

(52) U.S. Cl.

CPC ......... *G01N 33/5308* (2013.01); *C12Q 1/686* (2013.01); *G01N 33/58* (2013.01); *G01N 2400/10* (2013.01)

(58) Field of Classification Search

CPC ............... G01N 33/5308; G01N 33/58; G01N 2400/10; C12Q 1/686; C07K 14/42
See application file for complete search history.

(56) References Cited

U.S. PATENT DOCUMENTS

| | | | | |
|---|---|---|---|---|
| 2010/0028913 A1* | 2/2010 | Laine | ................ | G01N 33/5308 435/7.21 |
| 2018/0250360 A1 | 9/2018 | Tateno et al. | | |
| 2019/0250360 A1* | 8/2019 | Liu | ....................... | G02B 7/001 |

FOREIGN PATENT DOCUMENTS

| | | |
|---|---|---|
| JP | A-2008-187932 | 8/2008 |
| JP | A-2009-219388 | 10/2009 |
| JP | A-2017-507656 | 3/2017 |
| JP | A-2020-503893 | 2/2020 |
| WO | WO 2010/131641 A1 | 11/2010 |
| WO | WO 2015/128272 A2 | 9/2015 |
| WO | WO 2017/061449 A1 | 4/2017 |
| WO | WO 2018/122162 A1 | 7/2018 |
| WO | WO 2019089836 * | 5/2019 |

OTHER PUBLICATIONS

CA3081441, referred herein as WO219089836 A1, Chee et al, May 9, 2019.*

Office Action dated Oct. 31, 2023 issued in corresponding Japanese Patent Application No. 2020-053296 with English translation.

"Background and observations on a low molecular compound binding to Nakagawa Dominant, third Life Chain and Sugar chain", Pharmacia, 2014, vol. 50, pp. 1117-1122 (concise explanation of relevance in Japanese Office Action).

International Search Report mailed May 18, 2021 in corresponding PCT International Application No. PCT/JP2021/010385.

Feng, Y. et al., Lectin-mediated in situ rolling circle amplification on exosomes for probing cancer-related glycan pattern, Anal. Chim. Acta, 2018, vol. 1039, pp. 108-115.

Hirabayashi, J. et al., Glycomics, Coming of Age!, Trends in Glycoscience and Glycotechnology, 2000, vol. 12(63), pp. 1-5.

Fluorescence labeling rBC2LCN, FUJIFILM[online], Jan. 28, 2019, URL: https://labchem-wako.fujifilm.com/jp/category/00571.html, [retrieved on May 10, 2021].

Tateno, Hiroaki, "Development of sugar chain profiling technique and application to regenerative medicine and drug development", Bioscience & industry Award-winning achievements of Bioindustry Research Award, 2019, vol. 77(4), pp. 326-327.

Misevic, G. N. et al., New Nanotechnology Applications in Single Cell Analysis: Why and How?, Expression Profiling in Neuroscience, 2012, vol. 64, pp. 271-281.

* cited by examiner

*Primary Examiner* — Cynthia B Wilder

(74) *Attorney, Agent, or Firm* — OSTROLENK FABER LLP

(57) ABSTRACT

A method for analyzing a cell surface glycan is provided, the method including bringing a glycan-binding substance labeled with a nucleic acid into contact with the cell and detecting the nucleic acid labeled to the glycan-binding substance bound to the cell, in which a kind and a quantity of the nucleic acid correspond to a kind and a quantity of the cell surface glycan.

12 Claims, 26 Drawing Sheets

Specification includes a Sequence Listing.

| Lectin | GSLII | rABA | rBC2LCN | rLSLN | SNA |
|---|---|---|---|---|---|
| MFI | 253 | 11569 | 628769 | 41469 | 1014 |

SEQUENCE LISTING

<160> NUMBER OF SEQ ID NOS: 76

<210> SEQ ID NO 1
<211> LENGTH: 156
<212> TYPE: PRT
<213> ORGANISM: Burkholderia cepacia

<400> SEQUENCE: 1

```
Met Pro Leu Leu Ser Ala Ser Ile Val Ser Ala Pro Val Val Thr Ser
1               5                   10                  15

Glu Thr Tyr Val Asp Ile Pro Gly Leu Tyr Leu Asp Val Ala Lys Ala
            20                  25                  30

Gly Ile Arg Asp Gly Lys Leu Gln Val Ile Leu Asn Val Pro Thr Pro
        35                  40                  45

Tyr Ala Thr Gly Asn Asn Phe Pro Gly Ile Tyr Phe Ala Ile Ala Thr
    50                  55                  60

Asn Gln Gly Val Val Ala Asp Gly Cys Phe Thr Tyr Ser Ser Lys Val
65                  70                  75                  80

Pro Glu Ser Thr Gly Arg Met Pro Phe Thr Leu Val Ala Thr Ile Asp
                85                  90                  95

Val Gly Ser Gly Val Thr Phe Val Lys Gly Gln Trp Lys Ser Val Arg
            100                 105                 110

Gly Ser Ala Met His Ile Asp Ser Tyr Ala Ser Leu Ser Ala Ile Trp
        115                 120                 125

Gly Thr Ala Ala Pro Ser Ser Gln Gly Ser Gly Asn Gln Gly Ala Glu
    130                 135                 140

Thr Gly Gly Thr Gly Ala Gly Asn Ile Gly Gly Gly
145                 150                 155
```

<210> SEQ ID NO 2
<211> LENGTH: 4
<212> TYPE: PRT
<213> ORGANISM: Artificial Sequence
<220> FEATURE:
<223> OTHER INFORMATION: Synthesized peptide

<400> SEQUENCE: 2

```
Arg Arg Arg Arg
1
```

<210> SEQ ID NO 3
<211> LENGTH: 5
<212> TYPE: PRT
<213> ORGANISM: Artificial Sequence
<220> FEATURE:
<223> OTHER INFORMATION: Synthesized peptide

<400> SEQUENCE: 3

```
Arg Arg Arg Arg Arg
1               5
```

<210> SEQ ID NO 4
<211> LENGTH: 6
<212> TYPE: PRT
<213> ORGANISM: Artificial Sequence
<220> FEATURE:
<223> OTHER INFORMATION: Synthesized peptide

<400> SEQUENCE: 4

```
Arg Arg Arg Arg Arg Arg
1               5
```

```
<210> SEQ ID NO 5
<211> LENGTH: 7
<212> TYPE: PRT
<213> ORGANISM: Artificial Sequence
<220> FEATURE:
<223> OTHER INFORMATION: Synthesized peptide

<400> SEQUENCE: 5

Arg Arg Arg Arg Arg Arg Arg
1               5


<210> SEQ ID NO 6
<211> LENGTH: 10
<212> TYPE: PRT
<213> ORGANISM: Artificial Sequence
<220> FEATURE:
<223> OTHER INFORMATION: Synthesized peptide

<400> SEQUENCE: 6

Arg Arg Arg Arg Arg Arg Arg Arg Arg Arg
1               5                   10


<210> SEQ ID NO 7
<211> LENGTH: 79
<212> TYPE: PRT
<213> ORGANISM: Homo sapiens

<400> SEQUENCE: 7

Ser Ser Val Leu Ala Ser Cys Pro Lys Lys Pro Val Ser Ser Tyr Leu
1               5                   10                  15

Arg Phe Ser Lys Glu Gln Leu Pro Ile Phe Lys Ala Gln Asn Pro Asp
            20                  25                  30

Ala Lys Thr Thr Glu Leu Ile Arg Arg Ile Ala Gln Arg Trp Arg Glu
        35                  40                  45

Leu Pro Asp Ser Lys Lys Lys Ile Tyr Gln Asp Ala Tyr Arg Ala Glu
    50                  55                  60

Trp Gln Val Tyr Lys Glu Glu Ile Ser Arg Phe Lys Glu Gln Leu
65                  70                  75


<210> SEQ ID NO 8
<211> LENGTH: 65
<212> TYPE: DNA
<213> ORGANISM: Artificial Sequence
<220> FEATURE:
<223> OTHER INFORMATION: Synthesized oligonucleotide

<400> SEQUENCE: 8

gatattccgg gtctgtatct cgatgttgcg aaagcgggca tacgcgatgg gaaactgcag     60

gtgat                                                                 65


<210> SEQ ID NO 9
<211> LENGTH: 62
<212> TYPE: DNA
<213> ORGANISM: Artificial Sequence
<220> FEATURE:
<223> OTHER INFORMATION: Synthesized oligonucleotide

<400> SEQUENCE: 9

cgacgctctt ccgatctctg atgttgcgaa agcgggcata cggtcagatc ggaagagcac     60

ac                                                                    62


<210> SEQ ID NO 10
```

<211> LENGTH: 143
<212> TYPE: PRT
<213> ORGANISM: Agaricus bisporus

<400> SEQUENCE: 10

Met Thr Tyr Thr Ile Ser Ile Arg Val Tyr Gln Thr Thr Pro Lys Gly
1 5 10 15

Phe Phe Arg Pro Val Glu Arg Thr Asn Trp Lys Tyr Ala Asn Gly Gly
20 25 30

Thr Trp Asp Glu Val Arg Gly Glu Tyr Val Leu Thr Met Gly Gly Ser
35 40 45

Gly Thr Ser Gly Ser Leu Arg Phe Val Ser Ser Asp Thr Asp Glu Ser
50 55 60

Phe Val Ala Thr Phe Gly Val His Asn Tyr Lys Arg Trp Cys Asp Ile
65 70 75 80

Val Thr Asn Leu Thr Asn Glu Gln Thr Ala Leu Val Ile Asn Gln Glu
85 90 95

Tyr Tyr Gly Val Pro Ile Arg Asp Gln Ala Arg Glu Asn Gln Leu Thr
100 105 110

Ser Tyr Asn Val Ala Asn Ala Lys Gly Arg Arg Phe Ala Ile Glu Tyr
115 120 125

Thr Val Thr Glu Gly Asp Asn Leu Lys Ala Asn Leu Ile Ile Gly
130 135 140

<210> SEQ ID NO 11
<211> LENGTH: 78
<212> TYPE: DNA
<213> ORGANISM: Artificial Sequence
<220> FEATURE:
<223> OTHER INFORMATION: Synthesized oligonucleotide

<400> SEQUENCE: 11
tgggatgaag tgcgtggaga gtacgttctg actatgggtg gctctgggac ctcaggaagc 60
ttacggttcg tttcgagt 78

<210> SEQ ID NO 12
<211> LENGTH: 62
<212> TYPE: DNA
<213> ORGANISM: Artificial Sequence
<220> FEATURE:
<223> OTHER INFORMATION: Synthesized oligonucleotide

<400> SEQUENCE: 12
cgacgctctt ccgatctctg tgggtggctc tgggacctca gggtcagatc ggaagagcac 60
ac 62

<210> SEQ ID NO 13
<211> LENGTH: 149
<212> TYPE: PRT
<213> ORGANISM: Laetiporus sulphureus

<400> SEQUENCE: 13

Met Thr Asp Ile Tyr Ile Pro Pro Glu Gly Leu Tyr Phe Arg Leu Leu
1 5 10 15

Gly Phe Ala Ser Arg Gln Val Ile Phe Ala Arg Asn Ser Pro Ser Pro
20 25 30

Asp Val Gly Leu Ser Pro Val Asn Asp Gln Ala Thr Asp Gln Tyr Phe
35 40 45

Ser Leu Ile Tyr Gly Thr Gly Glu His Ala Gly Leu Tyr Ala Ile Lys

```
    50                  55                  60

Ser Lys Ala Thr Gly Lys Val Leu Phe Ser Arg Arg Pro Ala Glu Pro
65                  70                  75                  80

Tyr Val Gly Gln Ile Asp Gly Asp Gly Arg Tyr Pro Asp Asn Trp Phe
                85                  90                  95

Lys Ile Glu Pro Gly Lys Thr Tyr Leu Ser Lys Tyr Phe Arg Leu Val
            100                 105                 110

Gln Pro Ser Thr Gly Thr Ala Leu Val Ser Arg Thr His Leu Gln Pro
        115                 120                 125

Tyr Phe Trp Asn His Pro Gln Thr Glu Val Phe Asp Asp Gln Tyr Phe
    130                 135                 140

Thr Phe Leu Phe Glu
145


<210> SEQ ID NO 14
<211> LENGTH: 77
<212> TYPE: DNA
<213> ORGANISM: Artificial Sequence
<220> FEATURE:
<223> OTHER INFORMATION: Synthesized oligonucleotide

<400> SEQUENCE: 14

cgacatctac attccgccgg aaggcttgta ctttcgcttg cttgggtttg ccagtcgcca     60

ggtgattttc gcacgga                                                    77


<210> SEQ ID NO 15
<211> LENGTH: 63
<212> TYPE: DNA
<213> ORGANISM: Artificial Sequence
<220> FEATURE:
<223> OTHER INFORMATION: Synthesized oligonucleotide

<400> SEQUENCE: 15

cgacgctctt ccgatctctg cgcttgcttg ggtttgccag tcggtcagat cggaagagca     60

cac                                                                   63


<210> SEQ ID NO 16
<211> LENGTH: 94
<212> TYPE: DNA
<213> ORGANISM: Artificial Sequence
<220> FEATURE:
<223> OTHER INFORMATION: Synthesized oligonucleotide

<400> SEQUENCE: 16

tgcatcccgt accatcctgt tgctacagaa caatatctat gccgctagcc agggttggac     60

tgtgtcaaat aatgtacagc ccatcgttgc ttcg                                 94


<210> SEQ ID NO 17
<211> LENGTH: 62
<212> TYPE: DNA
<213> ORGANISM: Artificial Sequence
<220> FEATURE:
<223> OTHER INFORMATION: Synthesized oligonucleotide

<400> SEQUENCE: 17

cgacgctctt ccgatctctg tgccgctagc cagggttgga ctgtcagatc ggaagagcac     60

ac                                                                    62


<210> SEQ ID NO 18
<211> LENGTH: 66
```

<212> TYPE: DNA
<213> ORGANISM: Artificial Sequence
<220> FEATURE:
<223> OTHER INFORMATION: Synthesized oligonucleotide

<400> SEQUENCE: 18
tcggcaatgc tgtaagtgac ttaatcctcc aaggagccgc cacaccggac aaggggaccg 60
tcaaac 66

<210> SEQ ID NO 19
<211> LENGTH: 62
<212> TYPE: DNA
<213> ORGANISM: Artificial Sequence
<220> FEATURE:
<223> OTHER INFORMATION: Synthesized oligonucleotide

<400> SEQUENCE: 19
cgacgctctt ccgatctctg tcctccaagg agccgccaca ccgtcagatc ggaagagcac 60
ac 62

<210> SEQ ID NO 20
<211> LENGTH: 313
<212> TYPE: PRT
<213> ORGANISM: Aleuria aurantia

<400> SEQUENCE: 20

Met Pro Thr Glu Phe Leu Tyr Thr Ser Lys Ile Ala Ala Ile Ser Trp
1 5 10 15

Ala Ala Thr Gly Gly Arg Gln Gln Arg Val Tyr Phe Gln Asp Leu Asn
20 25 30

Gly Lys Ile Arg Glu Ala Gln Arg Gly Gly Asp Asn Pro Trp Thr Gly
35 40 45

Gly Ser Ser Gln Asn Val Ile Gly Glu Ala Lys Leu Phe Ser Pro Leu
50 55 60

Ala Ala Val Thr Trp Lys Ser Ala Gln Gly Ile Gln Ile Arg Val Tyr
65 70 75 80

Cys Val Asn Lys Asp Asn Ile Leu Ser Glu Phe Val Tyr Asp Gly Ser
85 90 95

Lys Trp Ile Thr Gly Gln Leu Gly Ser Val Gly Val Lys Val Gly Ser
100 105 110

Asn Ser Lys Leu Ala Ala Leu Gln Trp Gly Gly Ser Glu Ser Ala Pro
115 120 125

Pro Asn Ile Arg Val Tyr Tyr Gln Lys Ser Asn Gly Ser Gly Ser Ser
130 135 140

Ile His Glu Tyr Val Trp Ser Gly Lys Trp Thr Ala Gly Ala Ser Phe
145 150 155 160

Gly Ser Thr Val Pro Gly Thr Gly Ile Gly Ala Thr Ala Ile Gly Pro
165 170 175

Gly Arg Leu Arg Ile Tyr Tyr Gln Ala Thr Asp Asn Lys Ile Arg Glu
180 185 190

His Cys Trp Asp Ser Asn Ser Trp Tyr Val Gly Gly Phe Ser Ala Ser
195 200 205

Ala Ser Ala Gly Val Ser Ile Ala Ala Ile Ser Trp Gly Ser Thr Pro
210 215 220

Asn Ile Arg Val Tyr Trp Gln Lys Gly Arg Glu Glu Leu Tyr Glu Ala
225 230 235 240

Ala Tyr Gly Gly Ser Trp Asn Thr Pro Gly Gln Ile Lys Asp Ala Ser

```
            245                 250                 255

Arg Pro Thr Pro Ser Leu Pro Asp Thr Phe Ile Ala Ala Asn Ser Ser
        260                 265                 270

Gly Asn Ile Asp Ile Ser Val Phe Phe Gln Ala Ser Gly Val Ser Leu
    275                 280                 285

Gln Gln Trp Gln Trp Ile Ser Gly Lys Gly Trp Ser Ile Gly Ala Val
    290                 295                 300

Val Pro Thr Gly Thr Pro Ala Gly Trp
305                 310


<210> SEQ ID NO 21
<211> LENGTH: 86
<212> TYPE: DNA
<213> ORGANISM: Artificial Sequence
<220> FEATURE:
<223> OTHER INFORMATION: Synthesized oligonucleotide

<400> SEQUENCE: 21

cgcgattagc tggggttcaa ccccgaacat tcgcgtttac tggcagaaag gtcgcgaaga     60

gctgtacgaa gccgcttatg gtggtt                                          86


<210> SEQ ID NO 22
<211> LENGTH: 64
<212> TYPE: DNA
<213> ORGANISM: Artificial Sequence
<220> FEATURE:
<223> OTHER INFORMATION: Synthesized oligonucleotide

<400> SEQUENCE: 22

cgacgctctt ccgatctctg actggcagaa aggtcgcgaa gagcgtcaga tcggaagagc     60

acac                                                                  64


<210> SEQ ID NO 23
<211> LENGTH: 99
<212> TYPE: DNA
<213> ORGANISM: Artificial Sequence
<220> FEATURE:
<223> OTHER INFORMATION: Synthesized oligonucleotide

<400> SEQUENCE: 23

gtgacgccac aacaggaaca gatggtaact tggaactcac aagggtgtca agtaatggga     60

gtccacaggg aagcagtgtg ggccgggctt tgttctatg                            99


<210> SEQ ID NO 24
<211> LENGTH: 64
<212> TYPE: DNA
<213> ORGANISM: Artificial Sequence
<220> FEATURE:
<223> OTHER INFORMATION: Synthesized oligonucleotide

<400> SEQUENCE: 24

cgacgctctt ccgatctctg tgggagtcca cagggaagca gtgtgtcaga tcggaagagc     60

acac                                                                  64


<210> SEQ ID NO 25
<211> LENGTH: 76
<212> TYPE: DNA
<213> ORGANISM: Artificial Sequence
<220> FEATURE:
<223> OTHER INFORMATION: Synthesized oligonucleotide

<400> SEQUENCE: 25
```

atttcctcga tttggcaagc aagtggtctg gggtcaactc cgtggcgtag cgaaatcttt 60
gattgcgatg acttcg 76

<210> SEQ ID NO 26
<211> LENGTH: 64
<212> TYPE: DNA
<213> ORGANISM: Artificial Sequence
<220> FEATURE:
<223> OTHER INFORMATION: Synthesized oligonucleotide

<400> SEQUENCE: 26
cgacgctctt ccgatctctg ggtctggggt caactccgtg gcgtgtcaga tcggaagagc 60
acac 64

<210> SEQ ID NO 27
<211> LENGTH: 74
<212> TYPE: DNA
<213> ORGANISM: Artificial Sequence
<220> FEATURE:
<223> OTHER INFORMATION: Synthesized oligonucleotide

<400> SEQUENCE: 27
caatcagacg cgtattggtg tccaaccgcg caacatcacg accaaagggt ttgactgcgt 60
gttttatacg tgga 74

<210> SEQ ID NO 28
<211> LENGTH: 64
<212> TYPE: DNA
<213> ORGANISM: Artificial Sequence
<220> FEATURE:
<223> OTHER INFORMATION: Synthesized oligonucleotide

<400> SEQUENCE: 28
cgacgctctt ccgatctctg tccaaccgcg caacatcacg accagtcaga tcggaagagc 60
acac 64

<210> SEQ ID NO 29
<211> LENGTH: 73
<212> TYPE: DNA
<213> ORGANISM: Artificial Sequence
<220> FEATURE:
<223> OTHER INFORMATION: Synthesized oligonucleotide

<400> SEQUENCE: 29
caggcaatag ctgggaaaac gtctttagcg gctggtgtgt aggggccaat acggctagta 60
cccaaggtct gtc 73

<210> SEQ ID NO 30
<211> LENGTH: 62
<212> TYPE: DNA
<213> ORGANISM: Artificial Sequence
<220> FEATURE:
<223> OTHER INFORMATION: Synthesized oligonucleotide

<400> SEQUENCE: 30
cgacgctctt ccgatctctg agcggctggt gtgtaggggc cagtcagatc ggaagagcac 60
ac 62

<210> SEQ ID NO 31
<211> LENGTH: 75
<212> TYPE: DNA

<213> ORGANISM: Artificial Sequence
<220> FEATURE:
<223> OTHER INFORMATION: Synthesized oligonucleotide

<400> SEQUENCE: 31
ttggtgatgc cggtgtttac gtcgccctga acaacggcaa tggcacattt ggcccggtta 60
aacgcgtgat cgaca 75

<210> SEQ ID NO 32
<211> LENGTH: 64
<212> TYPE: DNA
<213> ORGANISM: Artificial Sequence
<220> FEATURE:
<223> OTHER INFORMATION: Synthesized oligonucleotide

<400> SEQUENCE: 32
cgacgctctt ccgatctctg tcgccctgaa caacggcaat ggcagtcaga tcggaagagc 60
acac 64

<210> SEQ ID NO 33
<211> LENGTH: 68
<212> TYPE: DNA
<213> ORGANISM: Artificial Sequence
<220> FEATURE:
<223> OTHER INFORMATION: Synthesized oligonucleotide

<400> SEQUENCE: 33
gcagaacgac tttaaacccg aatctgtggc agccattcgt tcctccgcgt ttaacagcaa 60
aggtggca 68

<210> SEQ ID NO 34
<211> LENGTH: 64
<212> TYPE: DNA
<213> ORGANISM: Artificial Sequence
<220> FEATURE:
<223> OTHER INFORMATION: Synthesized oligonucleotide

<400> SEQUENCE: 34
cgacgctctt ccgatctctg tgtggcagcc attcgttcct ccgcgtcaga tcggaagagc 60
acac 64

<210> SEQ ID NO 35
<211> LENGTH: 74
<212> TYPE: DNA
<213> ORGANISM: Artificial Sequence
<220> FEATURE:
<223> OTHER INFORMATION: Synthesized oligonucleotide

<400> SEQUENCE: 35
atcgtgaaca tcccgatcag ggtctgattt gccacgatgc gttctgtgga gccttggtga 60
tgaagatcgg caat 74

<210> SEQ ID NO 36
<211> LENGTH: 64
<212> TYPE: DNA
<213> ORGANISM: Artificial Sequence
<220> FEATURE:
<223> OTHER INFORMATION: Synthesized oligonucleotide

<400> SEQUENCE: 36
cgacgctctt ccgatctctg tgccacgatg cgttctgtgg agccgtcaga tcggaagagc 60
acac 64

<210> SEQ ID NO 37
<211> LENGTH: 75
<212> TYPE: DNA
<213> ORGANISM: Artificial Sequence
<220> FEATURE:
<223> OTHER INFORMATION: Synthesized oligonucleotide

<400> SEQUENCE: 37
cgttggattg tgacgacaca ctcggatggt actcgcacct tggaaaccgt aggcatcaac 60
agcagtgcct tcata 75

<210> SEQ ID NO 38
<211> LENGTH: 64
<212> TYPE: DNA
<213> ORGANISM: Artificial Sequence
<220> FEATURE:
<223> OTHER INFORMATION: Synthesized oligonucleotide

<400> SEQUENCE: 38
cgacgctctt ccgatctctg tggtactcgc accttggaaa ccgtgtcaga tcggaagagc 60
acac 64

<210> SEQ ID NO 39
<211> LENGTH: 75
<212> TYPE: DNA
<213> ORGANISM: Artificial Sequence
<220> FEATURE:
<223> OTHER INFORMATION: Synthesized oligonucleotide

<400> SEQUENCE: 39
tgcaaccagt tggggtacgg ttccgtccat tcgcgtctac accgcgaaca acggcaagat 60
caccgaacgt tgctg 75

<210> SEQ ID NO 40
<211> LENGTH: 64
<212> TYPE: DNA
<213> ORGANISM: Artificial Sequence
<220> FEATURE:
<223> OTHER INFORMATION: Synthesized oligonucleotide

<400> SEQUENCE: 40
cgacgctctt ccgatctctg tccgtccatt cgcgtctaca ccgcgtcaga tcggaagagc 60
acac 64

<210> SEQ ID NO 41
<211> LENGTH: 73
<212> TYPE: DNA
<213> ORGANISM: Artificial Sequence
<220> FEATURE:
<223> OTHER INFORMATION: Synthesized oligonucleotide

<400> SEQUENCE: 41
gtgttcgcga tgacaatctc gtcgatggtg cagctctggt tggctcacaa cagcctactc 60
cggtttccat tga 73

<210> SEQ ID NO 42
<211> LENGTH: 62
<212> TYPE: DNA
<213> ORGANISM: Artificial Sequence
<220> FEATURE:
<223> OTHER INFORMATION: Synthesized oligonucleotide

<400> SEQUENCE: 42
cgacgctctt ccgatctctg tggtgcagct ctggttggct cagtcagatc ggaagagcac 60
ac 62

<210> SEQ ID NO 43
<211> LENGTH: 75
<212> TYPE: DNA
<213> ORGANISM: Artificial Sequence
<220> FEATURE:
<223> OTHER INFORMATION: Synthesized oligonucleotide

<400> SEQUENCE: 43
tctcctttgt catcgatgca cctaacaaag ccaaagctgc agatggcctt gccttcttcc 60
ttgcacctgt ggata 75

<210> SEQ ID NO 44
<211> LENGTH: 64
<212> TYPE: DNA
<213> ORGANISM: Artificial Sequence
<220> FEATURE:
<223> OTHER INFORMATION: Synthesized oligonucleotide

<400> SEQUENCE: 44
cgacgctctt ccgatctctg gccaaagctg cagatggcct tgccgtcaga tcggaagagc 60
acac 64

<210> SEQ ID NO 45
<211> LENGTH: 71
<212> TYPE: DNA
<213> ORGANISM: Artificial Sequence
<220> FEATURE:
<223> OTHER INFORMATION: Synthesized oligonucleotide

<400> SEQUENCE: 45
cgaattggcc aagaacatca cctttgcgag tccgtattgc cgtccaccgg tagttctgct 60
gagcattacc c 71

<210> SEQ ID NO 46
<211> LENGTH: 64
<212> TYPE: DNA
<213> ORGANISM: Artificial Sequence
<220> FEATURE:
<223> OTHER INFORMATION: Synthesized oligonucleotide

<400> SEQUENCE: 46
cgacgctctt ccgatctctg gcgagtccgt attgccgtcc accggtcaga tcggaagagc 60
acac 64

<210> SEQ ID NO 47
<211> LENGTH: 70
<212> TYPE: DNA
<213> ORGANISM: Artificial Sequence
<220> FEATURE:
<223> OTHER INFORMATION: Synthesized oligonucleotide

<400> SEQUENCE: 47
gcgataatgc taagtggcag gtagcactcg ttgctgggtc tggggacagc gccgagtacc 60
tgatcatcaa 70

<210> SEQ ID NO 48
<211> LENGTH: 64

<212> TYPE: DNA
<213> ORGANISM: Artificial Sequence
<220> FEATURE:
<223> OTHER INFORMATION: Synthesized oligonucleotide

<400> SEQUENCE: 48
cgacgctctt ccgatctctg gcactcgttg ctgggtctgg ggacgtcaga tcggaagagc 60
acac 64

<210> SEQ ID NO 49
<211> LENGTH: 75
<212> TYPE: DNA
<213> ORGANISM: Artificial Sequence
<220> FEATURE:
<223> OTHER INFORMATION: Synthesized oligonucleotide

<400> SEQUENCE: 49
ctggtcaaaa tcggtccatg gggtggcaat ggaggcagtg cacaagacat ctcggttcca 60
cccaagaaac tgctt 75

<210> SEQ ID NO 50
<211> LENGTH: 64
<212> TYPE: DNA
<213> ORGANISM: Artificial Sequence
<220> FEATURE:
<223> OTHER INFORMATION: Synthesized oligonucleotide

<400> SEQUENCE: 50
cgacgctctt ccgatctctg gggtggcaat ggaggcagtg cacagtcaga tcggaagagc 60
acac 64

<210> SEQ ID NO 51
<211> LENGTH: 71
<212> TYPE: DNA
<213> ORGANISM: Artificial Sequence
<220> FEATURE:
<223> OTHER INFORMATION: Synthesized oligonucleotide

<400> SEQUENCE: 51
gaccatctac tactcctcaa ccatggtgaa cggcctgcaa gtcgtgtatg gcaatgggac 60
gacaaaactc c 71

<210> SEQ ID NO 52
<211> LENGTH: 64
<212> TYPE: DNA
<213> ORGANISM: Artificial Sequence
<220> FEATURE:
<223> OTHER INFORMATION: Synthesized oligonucleotide

<400> SEQUENCE: 52
cgacgctctt ccgatctctg tggtgaacgg cctgcaagtc gtgtgtcaga tcggaagagc 60
acac 64

<210> SEQ ID NO 53
<211> LENGTH: 72
<212> TYPE: DNA
<213> ORGANISM: Artificial Sequence
<220> FEATURE:
<223> OTHER INFORMATION: Synthesized oligonucleotide

<400> SEQUENCE: 53
tactcaaatc caagcgtcca ggttggcgaa gtctcaatcg gcgatcggag tctgaattcg 60
ggtacaggta gc 72

<210> SEQ ID NO 54
<211> LENGTH: 64
<212> TYPE: DNA
<213> ORGANISM: Artificial Sequence
<220> FEATURE:
<223> OTHER INFORMATION: Synthesized oligonucleotide

<400> SEQUENCE: 54
cgacgctctt ccgatctctg ggcgaagtct caatcggcga tcgggtcaga tcggaagagc 60
acac 64

<210> SEQ ID NO 55
<211> LENGTH: 78
<212> TYPE: DNA
<213> ORGANISM: Artificial Sequence
<220> FEATURE:
<223> OTHER INFORMATION: Synthesized oligonucleotide

<400> SEQUENCE: 55
cacctaatcc cagtacagca gctactgatg gtttagcgtt cttcttggca cccgctgata 60
cacaaccaca atctgccg 78

<210> SEQ ID NO 56
<211> LENGTH: 62
<212> TYPE: DNA
<213> ORGANISM: Artificial Sequence
<220> FEATURE:
<223> OTHER INFORMATION: Synthesized oligonucleotide

<400> SEQUENCE: 56
cgacgctctt ccgatctctg agcgttcttc ttggcacccg ctgtcagatc ggaagagcac 60
ac 62

<210> SEQ ID NO 57
<211> LENGTH: 74
<212> TYPE: DNA
<213> ORGANISM: Artificial Sequence
<220> FEATURE:
<223> OTHER INFORMATION: Synthesized oligonucleotide

<400> SEQUENCE: 57
caatatgggc cgtcgttttg ggccgtatgg cggtagcggt ggtagcgcga atacgctgtc 60
aaacgtcaaa gtga 74

<210> SEQ ID NO 58
<211> LENGTH: 63
<212> TYPE: DNA
<213> ORGANISM: Artificial Sequence
<220> FEATURE:
<223> OTHER INFORMATION: Synthesized oligonucleotide

<400> SEQUENCE: 58
cgacgctctt ccgatctctg cgtatggcgg tagcggtggt agcgtcagat cggaagagca 60
cac 63

<210> SEQ ID NO 59
<211> LENGTH: 62
<212> TYPE: DNA
<213> ORGANISM: Artificial Sequence
<220> FEATURE:
<223> OTHER INFORMATION: Synthesized oligonucleotide

<400> SEQUENCE: 59
acgattaccg acgatcaaca cgtgctgacg atgggtggca gtggaacctc tggtacctta 60
cg 62

<210> SEQ ID NO 60
<211> LENGTH: 62
<212> TYPE: DNA
<213> ORGANISM: Artificial Sequence
<220> FEATURE:
<223> OTHER INFORMATION: Synthesized oligonucleotide

<400> SEQUENCE: 60
cgacgctctt ccgatctctg cgtgctgacg atgggtggca gtgtcagatc ggaagagcac 60
ac 62

<210> SEQ ID NO 61
<211> LENGTH: 64
<212> TYPE: DNA
<213> ORGANISM: Artificial Sequence
<220> FEATURE:
<223> OTHER INFORMATION: Synthesized oligonucleotide

<400> SEQUENCE: 61
cgacgctctt ccgatctctg tggcaagtct gctgggatca tggcgtcaga tcggaagagc 60
acac 64

<210> SEQ ID NO 62
<211> LENGTH: 63
<212> TYPE: DNA
<213> ORGANISM: Artificial Sequence
<220> FEATURE:
<223> OTHER INFORMATION: Synthesized oligonucleotide

<400> SEQUENCE: 62
cgacgctctt ccgatctctg gtgggaatgg tggctcagcg ttcgtcagat cggaagagca 60
cac 63

<210> SEQ ID NO 63
<211> LENGTH: 62
<212> TYPE: DNA
<213> ORGANISM: Artificial Sequence
<220> FEATURE:
<223> OTHER INFORMATION: Synthesized oligonucleotide

<400> SEQUENCE: 63
cgacgctctt ccgatctctg actgatgcgc gtttagcccc gagtcagatc ggaagagcac 60
ac 62

<210> SEQ ID NO 64
<211> LENGTH: 64
<212> TYPE: DNA
<213> ORGANISM: Artificial Sequence
<220> FEATURE:
<223> OTHER INFORMATION: Synthesized oligonucleotide

<400> SEQUENCE: 64
cgacgctctt ccgatctctg acccaagcga tctgactgtc caccgtcaga tcggaagagc 60
acac 64

<210> SEQ ID NO 65

<211> LENGTH: 62
<212> TYPE: DNA
<213> ORGANISM: Artificial Sequence
<220> FEATURE:
<223> OTHER INFORMATION: Synthesized oligonucleotide

<400> SEQUENCE: 65
cgacgctctt ccgatctctg ggcggcaaca atcccattgc gtgtcagatc ggaagagcac 60
ac 62

<210> SEQ ID NO 66
<211> LENGTH: 63
<212> TYPE: DNA
<213> ORGANISM: Artificial Sequence
<220> FEATURE:
<223> OTHER INFORMATION: Synthesized oligonucleotide

<400> SEQUENCE: 66
cgacgctctt ccgatctctg tggcctttca cttcaaccca cgcgtcagat cggaagagca 60
cac 63

<210> SEQ ID NO 67
<211> LENGTH: 61
<212> TYPE: DNA
<213> ORGANISM: Artificial Sequence
<220> FEATURE:
<223> OTHER INFORMATION: Synthesized oligonucleotide

<400> SEQUENCE: 67
cgacgctctt ccgatctctg ctcgccacgc atccactggt ggtcagatcg gaagagcaca 60
c 61

<210> SEQ ID NO 68
<211> LENGTH: 61
<212> TYPE: DNA
<213> ORGANISM: Artificial Sequence
<220> FEATURE:
<223> OTHER INFORMATION: Synthesized oligonucleotide

<400> SEQUENCE: 68
cgacgctctt ccgatctctg gccgtgttgg tcgtgcttcg ggtcagatcg gaagagcaca 60
c 61

<210> SEQ ID NO 69
<211> LENGTH: 64
<212> TYPE: DNA
<213> ORGANISM: Artificial Sequence
<220> FEATURE:
<223> OTHER INFORMATION: Synthesized oligonucleotide

<400> SEQUENCE: 69
cgacgctctt ccgatctctg ggactccgat tgtaggctgg cagtgtcaga tcggaagagc 60
acac 64

<210> SEQ ID NO 70
<211> LENGTH: 63
<212> TYPE: DNA
<213> ORGANISM: Artificial Sequence
<220> FEATURE:
<223> OTHER INFORMATION: Synthesized oligonucleotide

<400> SEQUENCE: 70
cgacgctctt ccgatctctg tggaaagtgg gtcgctcagt ggggtcagat cggaagagca 60
cac 63

<210> SEQ ID NO 71
<211> LENGTH: 61
<212> TYPE: DNA
<213> ORGANISM: Artificial Sequence
<220> FEATURE:
<223> OTHER INFORMATION: Synthesized oligonucleotide

<400> SEQUENCE: 71
cgacgctctt ccgatctctg tgcgaatgca gccaacacgc agtcagatcg gaagagcaca 60
c 61

<210> SEQ ID NO 72
<211> LENGTH: 63
<212> TYPE: DNA
<213> ORGANISM: Artificial Sequence
<220> FEATURE:
<223> OTHER INFORMATION: Synthesized oligonucleotide

<400> SEQUENCE: 72
cgacgctctt ccgatctctg acagctactc gtgcgggaaa gcagtcagat cggaagagca 60
cac 63

<210> SEQ ID NO 73
<211> LENGTH: 64
<212> TYPE: DNA
<213> ORGANISM: Artificial Sequence
<220> FEATURE:
<223> OTHER INFORMATION: Synthesized oligonucleotide

<400> SEQUENCE: 73
cgacgctctt ccgatctctg gccggcgaaa tcacatgtgt ttgcgtcaga tcggaagagc 60
acac 64

<210> SEQ ID NO 74
<211> LENGTH: 61
<212> TYPE: DNA
<213> ORGANISM: Artificial Sequence
<220> FEATURE:
<223> OTHER INFORMATION: Synthesized oligonucleotide

<400> SEQUENCE: 74
cgacgctctt ccgatctctg agtgacgacg gtggcttgcc agtcagatcg gaagagcaca 60
c 61

<210> SEQ ID NO 75
<211> LENGTH: 73
<212> TYPE: DNA
<213> ORGANISM: Artificial Sequence
<220> FEATURE:
<223> OTHER INFORMATION: Synthesized oligonucleotide
<220> FEATURE:
<221> NAME/KEY: misc_feature
<222> LOCATION: (30)..(37)
<223> OTHER INFORMATION: n is a, c, g, or t

<400> SEQUENCE: 75
aatgatacgg cgaccaccga gatctacacn nnnnnnnaca ctctttccct acacgacgct 60
cttccgatct ctg 73

<210> SEQ ID NO 76

-continued

```
<211> LENGTH: 69
<212> TYPE: DNA
<213> ORGANISM: Artificial Sequence
<220> FEATURE:
<223> OTHER INFORMATION: Synthesized oligonucleotide
<220> FEATURE:
<221> NAME/KEY: misc_feature
<222> LOCATION: (25)..(32)
<223> OTHER INFORMATION: n is a, c, g, or t

<400> SEQUENCE: 76

caagcagaag acggcatacg agatnnnnnn nngtgactgg agttcagacg tgtgctcttc     60

cgatctgac                                                              69
```

METHOD FOR ANALYZING GLYCAN

CROSS-REFERENCE TO RELATED APPLICATIONS

The present application is a 35 U.S.C. §§ 371 national stage application of International Application No. PCT/JP2021/010385, filed Mar. 15, 2021, which claims priority to Japanese Patent Application No. 2020-053296, filed Mar. 24, 2020.

FIELD OF INVENTION

The present invention relates to a method for analyzing a glycan. More specifically, the present invention relates to a method for analyzing a glycan, a kit for analyzing a glycan, and a glycan-binding substance. Priority is claimed on Japanese Patent Application No. 2020-053296, filed Mar. 24, 2020, the content of which is incorporated herein by reference.

DESCRIPTION OF RELATED ART

Various proteins and lipids are present on the surface of cells. A large number of these have been subjected to glycan modification, and it is known that the surface of cells is covered with a wide variety of glycans.

It is known that glycans have a function such as mediating a cell-cell interaction and change depending on the kind and state of cells. For example, it is known that glycans can be used as cell undifferentiation markers or cancer markers.

In the related art, the analysis of glycans has been carried out by a method of staining cells or the like using a lectin or an antibody, a method of using a liquid chromatography apparatus and a mass spectrometer, a method of using a lectin array in which various kinds of lectins are immobilized on a substrate, and the like (see, for example, Patent Document 1).

CITATION LIST

Patent Document

Patent Document 1
PCT International Publication No. WO2010/131641

SUMMARY OF THE INVENTION

Technical Problem

However, it may be difficult to grasp the whole picture of glycans by the method of staining cells or the like using a lectin or an antibody. In addition, the method of using a liquid chromatography apparatus and a mass spectrometer requires a great deal of labor and a lot of time and samples.

On the other hand, according to the method of using a lectin array, glycans can be analyzed relatively easily. However, it may be difficult to analyze the glycome of an actual living cell since proteins extracted by destroying a cell are analyzed. In addition, it is necessary to use about 500 ng of proteins for analysis, and thus it is not possible to analyze glycans at a single cell level. For this reason, it is particularly difficult to analyze a tissue section. Further, although a lectin array is produced by using a special spotter, it tends to be difficult to produce a uniform lectin array due to the difference between lots. As a result, it may be difficult to obtain analysis results having good reproducibility by the method using a lectin array. In addition, the analysis of glycans using a lectin array requires a special and expensive scanner for detection. Based on this background, an object of the present invention is to provide a novel technique for analyzing a glycan.

Solution to Problem

The present invention includes the following aspects.

[1] A method for analyzing a cell surface glycan, the method including:

- bringing a glycan-binding substance labeled with a nucleic acid into contact with the cell; and
- detecting the nucleic acid labeled to the glycan-binding substance bound to the cell,
- in which a kind and a quantity of the nucleic acid correspond to a kind and a quantity of the glycan on the surface of the cell.

[2] The method according to claim 1, further including analyzing a phenotype of the cell or RNA information in the cell, together with the glycan.

[3] The method according to [1] or [2], in which the bringing of the glycan-binding substance labeled with the nucleic acid into contact with the cell is carried out in a buffer solution containing albumin.

[4] The method according to any one of [1] to [3], in which the method is carried out at a single cell level.

[5] The method according to any one of [1] to [4], in which the detection is carried out by real-time quantitative PCR, digital PCR, or sequencing with a next generation sequencer.

[6] A glycan-binding substance labeled with a nucleic acid.

[7] A kit for analyzing a cell surface glycan, the kit including the glycan-binding substance according to [6].

Advantageous Effects of Invention

According to the present invention, it is possible to provide a novel technique for analyzing a glycan.

DETAILED DESCRIPTION OF THE INVENTION

[Glycan-Binding Substance Labeled with Nucleic Acid]

Figure 1:
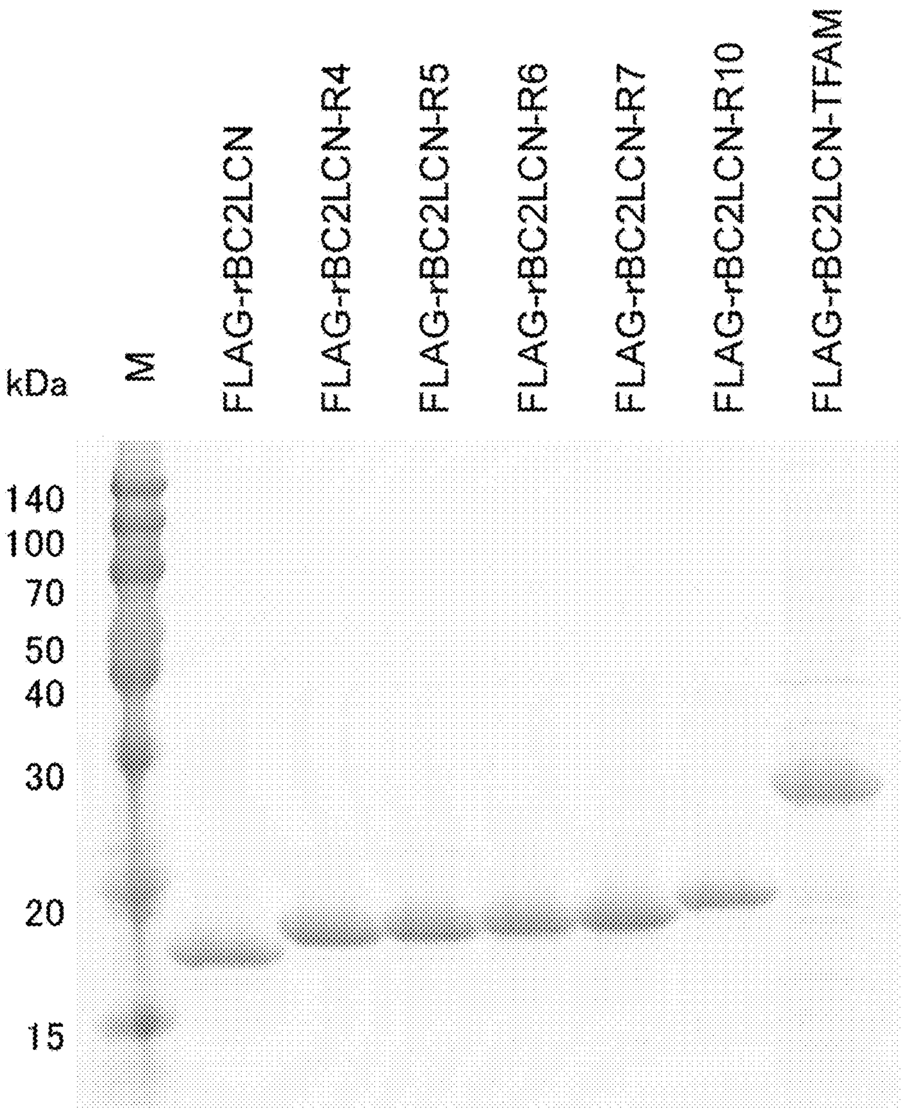
FIG. 1 is a photographic image showing the results of Coomassie Brilliant Blue (CBB) staining after separating each purified fusion protein by SDS-polyacrylamide gel electrophoresis (SDS-PAGE) in Experimental Example 1.

In one embodiment, the present invention provides a glycan-binding substance labeled with a nucleic acid. As will be described later, in a case of using the glycan-binding substance of the present embodiment, a cell surface glycan can be easily analyzed with a high sensitivity.

The glycan-binding substance is not particularly limited as long as it is a substance that recognizes glycan structure and specifically binds thereto, and examples thereof include a lectin, an antibody, an antibody fragment, and an aptamer. Examples of the antibody fragment include F(ab')2, Fab', Fab, Fv, and scFv.

In the present specification, lectin is defined as a general term referring to proteins having an activity of binding to a glycan. The lectin is not particularly limited, and it is possible to suitably use, for example, the lectins shown in Tables 1 to 5 below. In Tables 1 to 5, “Natural” indicates that the corresponding one is derived from a natural product, and “*E. coli*” indicates that the corresponding one is a genetically modified product. In addition, “EY Lab.” indicates EY Laboratories Inc., “Wako” indicates FUJIFILM Wako Pure Chemical Corporation, “Seikagaku” indicates SEIKAGAKU CORPORATION, “Vector” indicates Vector Laboratories, Inc., “JOM” indicates J-OIL MILLS, Inc., and “AIST” indicates National Institute of Advanced Industrial Science and Technology. The lectin from the source of supply of “AIST” is prepared by the inventors (Tateno H., et al., Glycome diagnosis of human induced pluripotent stem cells using lectin microarray, J Biol Chem., 286 (23), see 20345-20353, 2011).

In addition, “Sia” indicates sialic acid, “GlcNAc” indicates N-acetyl-glucosamine, “Man” indicates mannose, “Gal” indicates D-galactose, “GalNAc” indicates N-acetyl-galactosamine, “Fuc” indicates L-fucose, “Glc” indicates D-glucose, and “LacNAc” indicates N-acetyl-lactosamine.

The lectin is preferably a recombinant lectin derived from *Escherichia coli*, which has not been subjected to glycan modification. Further, in order to comprehensively analyze the glycan, it is preferable to use a mix of lectins that recognize Sia, Gal, GlcNAc, Man, Fuc, and GalNAc, which are monosaccharides constituting the glycan.

TABLE 1

| Number | Name of lectin | Species from which lectin is derived | Origin | Source of supply | Specificity |
|---|---|---|---|---|---|
| 1 | LFA | *Limax flavus* | Natural | EY Lab. | Sia |
| 2 | WGA | *Triticum vulgaris* | Natural | EY Lab. | (GlcNAc)n, polySia |
| 3 | PVL | *Psathyrella velutina* | Natural | Wako | Sia, GlcNAc |
| 4 | MAL | *Maackia amurensis* | Natural | Seikagaku | α2-3Sia |
| 5 | MAH | *Maackia amurensis* | Natural | Vector | α2-3Sia |
| 6 | ACG | *Agrocybe cylindracea* | Natural | JOM | α2-3Sia |
| 7 | rACG | *Agrocybe cylindracea* | *E. coli* | AIST | α2-3Sia |
| 8 | rGal8N | *Homo sapiens* | *E. coli* | AIST | α2-3Sia |
| 9 | SNA | *Sambucus nigra* | Natural | Seikagaku | α2-6Sia |
| 10 | SSA | *Sambucus sieboldiana* | Natural | Vector | α2-6Sia |
| 11 | TJAI | *Trichosanthes japonica* | Natural | Vector | α2-6Sia |
| 12 | rPSL1a | *Polyporus squamosus* | *E. coli* | AIST | α2-6Sia |
| 13 | PHAL | *Phaseolus vulgaris* | Natural | Seikagaku | GlcNAcβ1-6Man (Tetraantenna) |
| 14 | DSA | *Datura stramonium* | Natural | Seikagaku | GlcNAcβ1-6Man (Tetraantenna) |
| 15 | TxLcI | *Tulipa gesneriana* | Natural | JOM | Galactosylated N-glycans up to triantenna |
| 16 | ECA | *Erythrina cristagalli* | Natural | Seikagaku | βGal |
| 17 | RCA120 | *Ricinus communis* | Natural | Vector | βGal |
| 18 | rGal7 | *Homo sapiens* | *E. coli* | AIST | Type1 LacNAc, chondroitin polymer |
| 19 | rGal9N | *Homo sapiens* | *E. coli* | AIST | GalNAcα1-4Gal (A), PolyLacNAc |
| 20 | rGal9C | *Homo sapiens* | *E. coli* | AIST | PolyLacNAc, Branched LacNAc |

TABLE 2

| Number | Name of lectin | Species from which lectin is derived | Origin | Source of supply | Specificity |
|---|---|---|---|---|---|
| 21 | rC14 | *Gallus gallus domesticus* | *E. coli* | AIST | Branched LacNAc |
| 22 | rDiscoidin II | *Dictyostelium dicodeum* | *E. coli* | AIST | LacNAc, Galβ1-3GalNAc (T), GalNAc (Tn) |
| 23 | BPL | *Bauhinia purpurea alba* | Natural | Vector | Galβ1-3GlcNAc(GalNAc), α/βGalNAc |
| 24 | rCGL2 | *Homo sapiens* | *E. coli* | AIST | GalNAcα1-3Gal (A), PolyLacNAc |
| 25 | PHAE | *Phaseolus vulgaris* | Natural | Vector | bisecting GlcNAc |
| 26 | GSLII | *Griffonia simplicifolia* | Natural | Vector | GlcNAcβ1-4Man |
| 27 | rSRL | *Sclerotium rolfsii* | *E. coli* | AIST | Core1,3, agalacto N-glycan |
| 28 | UDA | *Urtica dioica* | Natural | Vector | (GlcNAc)n |
| 29 | PWM | *Phytolacca americana* | Natural | Vector | (GlcNAc)n |
| 30 | rF17AG | *Escherichia coli* | *E. coli* | AIST | GlcNAc |
| 31 | rGRFT | *Griffithia* sp. | *E. coli* | AIST | Man |
| 32 | NPA | *Narcissus pseudonarcissus* | Natural | Seikagaku | Mana1-3Man |
| 33 | ConA | *Canavalia ensiformis* | Natural | Vector | M3, Manα1-2Manα1-3(Manα1-6)Man, GlcNAcβ1-2Manα1-3(Manα1-6)Man |
| 34 | GNA | *Galanthus nivalis* | Natural | Vector | Manα1-3Man, Manα1-6Man |
| 35 | HHL | *Hippeastrum hybrid* | Natural | Vector | Manα1-3Man, Manα1-6Man |
| 36 | ASA | *Allium sativum* | Natural | JOM | Galβ1-4GlcNAcβ1-2Man |

TABLE 2-continued

| Number | Name of lectin | Species from which lectin is derived | Origin | Source of supply | Specificity |
|---|---|---|---|---|---|
| 37 | DBAI | *Dioscorea batatas* | Natural | JOM | High-man |
| 38 | CCA | *Castanea crenata* | Natural | JOM | Galactosylated N-glycans up to triantenna |
| 39 | Heltuba | *Helianthus tuberosus* | Natural | JOM | Manα1-3Man |
| 40 | rHeltuba | *Helianthus tuberosus* | *E. coli* | AIST | Manα1-3Man |

TABLE 3

| Number | Name of lectin | Species from which lectin is derived | Origin | Source of supply | Specificity |
|---|---|---|---|---|---|
| 41 | ADA | *Allomyrina dichtoma* | Natural | JOM | α2-6Sia, Forssman, A, B |
| 42 | VVAII | *Vicia villosa* | Natural | JOM | Man, Agalacto |
| 43 | rOrysata | *Oryza sativa* | *E. coli* | AIST | Manα1-3Man, Highman, biantenna |
| 44 | rPALa | *Phlebodium aureum* | *E. coli* | AIST | Man5, biantenna |
| 45 | rBanana | *Musa acuminata* | *E. coli* | AIST | Manα1-2Manα1-3(6)Man |
| 46 | rCalsepa | *Calystegia sepium* | *E. coli* | AIST | Biantenna with bisecting GlcNAc |
| 47 | rRSL | *Ralstonia solanacearum* | *E. coli* | AIST | αMan, α1-2Fuc (H), α1-3Fuc (Lex), α1-4Fuc (Lea) |
| 48 | rBC2LA | *Burkholderia cenocepacia* | *E. coli* | AIST | αMan, High-man |
| 49 | AOL | *Aspergillus oryzae* | Natural | Vector | α1-2Fuc (H), α1-3Fuc (Lex), α1-3Fuc(Lea) |
| 50 | AAL | *Aleuria aurantia* | Natural | Vector | α1-2Fuc (H), α1-3Fuc (Lex), α1-4Fuc (Lea) |
| 51 | rAAL | *Aleuria aurantia* | *E. coli* | AIST | α1-2Fuc (H), α1-3Fuc (Lex), α1-3Fuc (Lea) |
| 52 | rPAIIL | *Pseudomonas aeruginosa* | *E. coli* | AIST | αMan, α1-2Fuc (H), α1-3Fuc (Lex), α1-4Fuc (Lea) |
| 53 | rRSIIL | *Ralstonia solanacearum* | *E. coli* | AIST | α1-2Fuc (H), α1-3Fuc (Lex), α1-3Fuc (Lea) |
| 54 | rPTL | *Pholiota terrestris* | *E. coli* | AIST | α1-6Fuc |
| 55 | PSA | *Pisum sativum* | Natural | Seikagaku | α1-6Fuc up to biantenna |
| 56 | LCA | *Lens culinaris* | Natural | Vector | α1-6Fuc up to biantenna |
| 57 | rAOL | *Aspergillus oryzae* | *E. coli* | AIST | α1-2Fuc (H), α1-3Fuc (Lex), α1-3Fuc (Lea) |
| 58 | rBC2LCN | *Burkholderia cenocepacia* | *E. coli* | AIST | Fuc α1-2Galβ1-3GlcNAc (GalNAc) |
| 59 | LTL | *Lotus tetragonolobus* | Natural | Seikagaku | Lex, Ley |
| 60 | UEAI | *Ulex europaeus* | Natural | Vector | α1-2Fuc |

TABLE 4

| Number | Name of lectin | Species from which lectin is derived | Origin | Source of supply | Specificity |
|---|---|---|---|---|---|
| 61 | TJAII | *Trichosanthes japonica* | Natural | Vector | α1-2Fuc |
| 62 | MCA | *Momordica charantia* | Natural | JOM | α1-2Fuc |
| 63 | GSLI | *Griffonia simplicifolia* | Natural | Seikagaku | αGalNAc (A, Tn), αGal (B) |
| 64 | PTLI | *Psophocarpus tetragonolobus* | Natural | Tokyo Kasei | αGalNAc (A, Tn) |
| 65 | GSLIA4 | *Griffonia simplicifolia* | Natural | EY Lab. | αGalNAc (A, Tn) |
| 66 | rGC2 | *Geodia cydonium* | *E. coli* | AIST | α1-2Fuc (H), αGalNAc (A), αGal (B) |

TABLE 4-continued

| Number | Name of lectin | Species from which lectin is derived | Origin | Source of supply | Specificity |
|---|---|---|---|---|---|
| 67 | GSLIB4 | *Griffonia simplicifolia* | Natural | Vector | αGal (B) |
| 68 | rMOA | *Marasmius oreades* | *E. coli* | AIST | αGal (B) |
| 69 | EEL | *Euonymus europaeus* | Natural | Vector | αGal (B) |
| 70 | rPAIL | *Pseudomonas aeruginosa* | *E. coli* | AIST | α,βGal, αGalNAc (Tn) |
| 71 | LEL | *Lycopersicon esculentum* | Natural | Vector | Polylactosamine, (GlcNAc)n |
| 72 | STL | *Solanum tuberosum* | Natural | Seikagaku | Polylactosamine, (GlcNAc)n |
| 73 | rGal3C | *Homo sapiens* | *E. coli* | AIST | LacNAc, polylactosamine |
| 74 | rLSLN | *Laetiporus sulphureus* | *E. coli* | AIST | LacNAc, polylactosamine |
| 75 | rCGL3 | *Coprinopsis cinerea* | *E. coli* | AIST | LacDiNAc |
| 76 | PNA | *Arachis hypogaea* | Natural | Vector | Galβ1-3GalNAc (T) |
| 77 | ACA | *Amaranthus caudatus* | Natural | Vector | Galβ1-3GalNAc (T) |
| 78 | HEA | *Hericium erinaceum* | Natural | JOM | Galβ1-3GalNAc (T) |
| 79 | ABA | *Agarics bisporus* | Natural | Vector | Galβ1-3GalNAc (T), GlcNAc |
| 80 | Jacalin | *Artocarpus integrifolia* | Natural | Seikagaku | Galβ1-3GalNAc (T), GalNAcα (Tn) |

TABLE 5

| Number | Name of lectin | Species from which lectin is derived | Origin | Source of supply | Specificity |
|---|---|---|---|---|---|
| 81 | MPA | *Maclura pomifera* | Natural | Seikagaku | Galβ1-3GalNAc (T), GalNAcα (Tn) |
| 82 | HPA | *Helix pomatia* | Natural | Seikagaku | αGalNAc (A, Tn) |
| 83 | VVA | *Vicia villosa* | Natural | Vector | α,βGalNAc (A, Tn, LacDiNAc) |
| 84 | DBA | *Dolichos biflorus* | Natural | Vector | α,βGalNAc (A, Tn, LacDiNAc) |
| 85 | SBA | *Glycine max* | Natural | EY Lab. | α,βGalNAc (A, Tn, LacDiNAc) |
| 86 | rPPL | *Pleurocybella porrigens* | *E. coli* | AIST | α,βGalNAc (A, Tn, LacDiNAc) |
| 87 | rCNL | *Clitocybe nebularis* | *E. coli* | AIST | α,βGalNAc (A, Tn, LacDiNAc) |
| 88 | rXCL | *Xerocomus chrysenteron* | *E. coli* | AIST | Core1,3, agalacto N-glycan |
| 89 | VVA I | *Vicia villosa* | Natural | JOM | GalNAcβ1-3(4)Gal |
| 90 | WFA | *Wisteria floribunda* | Natural | Vector | Terminal GalNAc, LacDiNAc |
| 91 | rABA | *Agarics bisporus* | *E. coli* | AIST | Galβ1-3GalNAc (T), GlcNAc |
| 92 | rDiscoidin I | *Dictyostelium Discodeum* | *E. coli* | AIST | Gal |
| 93 | DBAIII | *Dioscorea batatas* | Natural | JOM | Maltose |
| 94 | rMalectin | *Homo sapiens* | *E. coli* | AIST | Glcα1-2Glc |
| 95 | CSA | *Oncorhynchus keta* | Natural | JOM | Rhamnose, Galα1-4Gal |
| 96 | FLAG-EW29Ch-E20K | *Lumbricus terrestris* | *E. coli* | AIST | 6-sulfo-Gal |

The nucleic acid with which the glycan-binding substance is labeled may be, for example, a cyclic nucleic acid. It may be, for example, a single-stranded nucleic acid fragment or may be, for example, a double-stranded nucleic acid fragment. Examples of the circular nucleic acid include plasmid DNA. In addition, the nucleic acid with which the glycan-binding substance is labeled may be DNA or RNA; however, it is preferably DNA from the viewpoint of stability.

It is preferable to label a specific kind of glycan-binding substance with a specific kind of nucleic acid. For example, in a case of causing the kind of glycan-binding substance to correspond to the base sequence of the nucleic acid with which the glycan-binding substance is labeled, it is possible to encode the glycan-binding substance. As a result, the base sequence of the nucleic acid with which the glycan-binding substance is labeled is preferably a base sequence that is not present in nature. In a case of detecting the base sequence specific to the nucleic acid with which the glycan-binding substance is labeled, it is possible to detect the presence of the glycan-binding substance corresponding thereto.

Further, in a case of amplifying the nucleic acid bonded to the glycan-binding substance by PCR or the like, it is possible to amplify the signal that indicates the presence of the glycan-binding substance. As a result, it is possible to increase, for example, the detection sensitivity.

In a case where the nucleic acid with which the glycan-binding substance is labeled is a single-stranded nucleic acid fragment or a double-stranded nucleic acid fragment, the length thereof does not affect the binding of the glycan and is not particularly limited as long as it can retain the information that indicates the corresponding glycan-binding substance. For example, it may be several tens of bases (or base pairs) to several tens of kilobases (or base pairs). Further, the nucleic acid may be circular DNA such as a plasmid.

As will be described later, the nucleic acid with which the glycan-binding substance is labeled may be detected by real-time quantitative PCR, digital PCR, or sequencing by a next generation sequencer.

Therefore, it is preferable that the nucleic acid with which the glycan-binding substance is labeled further have a base sequence region to which a PCR primer can hybridize. In addition, in a case where the nucleic acid with which the glycan-binding substance is labeled is detected by sequencing with a next generation sequencer, the nucleic acid with which the glycan-binding substance is labeled preferably further has a base sequence that enables the pretreatment for the next generation sequencing such as bridge PCR or emulsion PCR.

The length of the nucleic acid with which the glycan-binding substance is labeled is particularly preferably 50 to 100 bases. Among these, the base sequence for encoding the glycan-binding substance is 10 to 30 bases, and it is preferable to add an adapter sequence of 10 to 30 bases to each of the 5' side and the 3' side thereof. The base sequence for encoding the glycan-binding substance is selected so that the base is not biased.

In addition to the sequence complementary to the adapter sequence, the base sequence of the PCR primer preferably includes a base sequence (5 to 10 bases) for identifying various kinds of cells and a base sequence (20 to 30 bases) for hybridizing to a flow cell in the next generation sequencing.

As will be described later in Examples, the binding of a nucleic acid to the glycan-binding substance may be carried out, for example, by linking a nucleic acid-binding domain to the glycan-binding substance and binding the nucleic acid to the nucleic acid binding domain, may be carried out by using a chemical linker to bind the glycan-binding substance to a nucleic acid, or may be carried out by using the click reaction to bind the glycan-binding substance to a nucleic acid.

In order for a chemical linker to be capable of being usable, a functional group such as an amino group or an SH group may be introduced into the nucleic acid. Further, in order for the click reaction to be capable of being usable, an azide group, an alkyne group, or the like may be introduced into the nucleic acid. The introduction of this group can be carried out by chemical synthesis of nucleic acid, or the like.

Further, a spacer may be present between the glycan-binding substance and the nucleic acid. The spacer is not particularly limited, and examples thereof include a polyethylene glycol chain, a polyacrylamide chain, a polyester chain, a polyurethane chain, and a copolymer thereof. The spacer may be derived from a chemical linker.

The spacer may also contain a cleavable group. For example, as will be described later in Examples, in a case where the spacer contains a group that is cleavable upon irradiation with light, it is possible to detach the nucleic acid from the glycan-binding substance and recover it by irradiating the glycan-binding substance labeled with a nucleic acid with light.

[Method of Analyzing a Glycan]

In one embodiment, the present invention provides a method for analyzing a cell surface glycan, the method including bringing glycan-binding substance labeled with a nucleic acid into contact with the cell and detecting the nucleic acid labeled to the glycan-binding substance bound to the cell, in which a kind and a quantity of the nucleic acid correspond to a kind and a quantity of the glycan on the surface of the cell.

The cell is not particularly limited, and examples thereof include a microorganism (a virus, a bacterium, a fungus), an insect cell, a plant cell, and an animal cell. Further, a tissue section or the like can also be used as a specimen. Regarding the cell or the tissue section, the cell may be in a state of being alive or fixed.

In the method of the present embodiment, first, a glycan-binding substance labeled with a nucleic acid is brought into contact with cells to be analyzed. As the glycan-binding substance labeled with a nucleic acid, the above-described substance can be used.

One kind of glycan-binding substance labeled with a nucleic acid may be singly brought into contact with cells, or two or more kinds thereof may be mixed and brought into contact with cells. In a case of simultaneously bringing various kinds of glycan-binding substances labeled with a nucleic acid into contact with cells, it is possible to comprehensively analyze the glycan structures on the surface of cells.

The bringing of the glycan-binding substance labeled with a nucleic acid into contact with cells can be carried out by mixing the cell and the glycan-binding substance labeled with a nucleic acid, in a solution such as in a culture medium, physiological saline, or a buffer solution.

Among the above, the bringing of the glycan-binding substance labeled with a nucleic acid into contact with cells is preferably carried out in a buffer solution containing albumin. As will be described later in Examples, the detection signal can be significantly enhanced by carrying out the bringing of the glycan-binding substance labeled with a nucleic acid into contact with cells in a buffer solution containing albumin.

Examples of the buffer solution include a Tris buffer solution and phosphate-buffered saline. Examples of the composition of the phosphate-buffered saline include NaCl 137 mmol/L, KCl 2.7 mmol/L, $Na_2HPO_4$ 10 mmol/L, and $KH_2PO_4$ 1.76 mmol/L. Further, it is preferable that the pH of the phosphate-buffered saline be adjusted to about 7.4.

As the albumin, bovine serum albumin, human serum albumin, and the like can be used. The albumin may be a recombinant thereof. The concentration of albumin in the buffer solution is preferably about 0.1 to 10% by mass.

Regarding the amount of the glycan-binding substance labeled with a nucleic acid to be brought into contact with the cells to be analyzed, it suffices that one or more molecules with respect to one kind of glycan-binding substance labeled with a nucleic acid be brought into contact per a single cell, and it is preferable that the amount be such that the cell surface glycan can be saturated.

In addition, the time required for the glycan-binding substance labeled with a nucleic acid to be brought into contact with the cell to be analyzed is not particularly limited as long as it is a time sufficient for the glycan-binding substance to bind to the glycan on the surface of the cells to be analyzed. It may be, for example, about 10 minutes to 24 hours, for example, may be about 10 minutes to 8 hours, for example, may be about 10 minutes to 3 hours, and for example, may be about 1 hour. In addition, the temperature at which the glycan-binding substance labeled with a nucleic acid is brought into contact is not particularly limited as long as the glycan-binding substance binds to the cell surface glycan to be analyzed, and it may be, for example, about 4° C. to 37° C.

As a result of bringing the glycan-binding substance labeled with a nucleic acid into contact with the cells to be analyzed, the glycan-binding substance binds to the cell surface glycan to be analyzed. Here, it is preferable to remove the unreacted glycan-binding substance. The unreacted glycan-binding substance can be removed, for example, by repeating the operation of adding a buffer solution and centrifuging cells to remove the supernatant one to several times.

Subsequently, the nucleic acid labeled to the glycan-binding substance bound to the cell is detected. Here, the detection of the nucleic acid may be carried out in a state where the glycan-binding substance labeled with a nucleic acid is bound to the cell, may be carried out after the glycan-binding substance labeled with a nucleic acid is dissociated from the cell and further the glycan-binding substance labeled with a nucleic acid is separated from the cell, or may be carried out after a nucleic acid is detached and recovered from the glycan-binding substance labeled with the nucleic acid.

Examples of the method of dissociating the glycan-binding substance labeled with a nucleic acid from the cell include a method of reacting a cell with sugar that competes with the glycan-binding substance, a method of allowing a surfactant to act to dissociate the binding between the glycan-binding substance and the cell surface glycan, a method of changing the pH to dissociate the binding between the glycan-binding substance and the cell surface glycan, and a method of allowing a reducing agent to act to dissociate the binding between the glycan-binding substance and the glycan on the surface of the cell.

Further, as described above, in a case where a cleavable group is introduced between the nucleic acid and the glycan-binding substance, the nucleic acid can be detached and recovered from the glycan-binding substance labeled with a nucleic acid. For example, in a case where a group that can be cleavable upon irradiation with light is introduced between the nucleic acid and the glycan-binding substance in advance, the nucleic acid can be detached from the glycan-binding substance labeled with a nucleic acid by irradiating with light. Then, it is possible to recover the nucleic acid, for example, by carrying out centrifugal separation to recover the supernatant.

The detection of the nucleic acid labeled to the glycan-binding substance bound to the cell may be carried out by, for example, real-time quantitative PCR, digital PCR, or sequencing with a next generation sequencer. By amplifying the nucleic acid by PCR or the like, the detection signal can be amplified, and the detection sensitivity can be increased. Here, a kind and a quantity of the nucleic acid detected corresponds to a kind and a quantity of the cell surface glycan.

Here, the kind of the nucleic acid is the kind of the base sequence of the nucleic acid labeled to the glycan-binding substance. In a case of specifying the kind of the nucleic acid, it is possible to specify the kind of the glycan-binding substance to which the nucleic acid is labeled. As a result, in a case of specifying the base sequence of the nucleic acid, it is possible to specify the structure of the cell surface glycan to be analyzed. In addition, the amount of the nucleic acid having a specific base sequence corresponds to the amount of the glycan-binding substance bound to the cells to be analyzed. That is, the amount of the nucleic acid having a specific base sequence corresponds to the amount of the specific glycan structure present on the surface of the cells to be analyzed. This makes it possible to quantitatively analyze the kind of structure of the glycan and the quantity of glycan present on the surface of the cells to be analyzed.

Real-time quantitative PCR, digital PCR, and next generation sequencing can be carried out using general-purpose devices. Accordingly, in a case where these devices are already present, it is not necessary to prepare a new special device for the analysis of glycans.

Further, as will be described later in Examples, since the method of the present embodiment has high detection sensitivity, it is also possible to analyze a cell surface glycan at a single cell level. Here, to analyze a cell surface glycan at a single cell level means that a single cell is used as a specimen, a glycan-binding substance labeled with a nucleic acid is brought into contact with the specimen, the nucleic acid labeled to the glycan-binding substance bound is detected, and the kind and quantity of the cell surface glycan are specified. The analysis of glycan at a single cell level could not be carried out by the methods in the related art.

Further, in the method of the present embodiment, cells are still alive even after the nucleic acid is recovered from the surface of the cells. Therefore, it is possible to analyze the cell surface glycan and simultaneously analyze the phenotype of the cell or the RNA information in the cell.

Examples of the phenotype of the cell include cell morphology, proliferation ability, differentiation ability, infiltration ability, tumor-forming ability, and the expression of marker protein. In addition, it is also possible to analyze the intracellular genetic information or the phenotype of cells at a single cell level. Examples of the RNA information in the cell include base sequence information or expression level information on mRNA, microRNA, 16S rRNA, non-coding RNA, and the like.

[Kit]

In one embodiment, the present invention provides a kit for analyzing a cell surface glycan, which includes the above-described glycan-binding substance labeled with a nucleic acid. In a case of using the kit of the present embodiment, it is possible to suitably carry out the analysis of a cell surface glycan.

The kit of the present embodiment may contain one kind of glycan-binding substance labeled with a nucleic acid, or it may contain two or more kinds thereof, for example, 10 kinds or more thereof, for example, 30 kinds or more thereof, for example, 50 kinds or more thereof, or for example, 100 kinds or more thereof. In a case where the kit of the present embodiment contains various kinds of glycan-binding substances labeled with a nucleic acid, it is easy to comprehensively analyze the structures of the cell surface glycan, which is preferable.

The kit of the present embodiment may further contain a buffer solution containing albumin as a solvent in which the glycan-binding substance labeled with a nucleic acid is brought into contact with the cells to be analyzed. The buffer solution containing albumin is the same as that described above. As will be described later in Examples, it is possible to suppress the background in a case in which bringing the glycan-binding substance labeled with a nucleic acid into contact with the cells is carried out in a buffer solution containing albumin.

In addition, the kit of the present embodiment may further contain a primer for detecting a nucleic acid bonded to the glycan-binding substance. The nucleic acid bonded to the glycan-binding substance can be detected by real-time quantitative PCR, digital PCR, next generation sequencing, or the like using the above primer.

EXAMPLES

Next, the present invention will be described in more detail by showing Examples; however, the present invention is not limited to Examples below.

[Lectin]

The lectins shown in Table 6 below were used. In addition, in a case where each lectin was labeled with a nucleic acid, it was labeled with a nucleic acid consisting of the base sequence set forth in the SEQ ID NO shown in Table 6 below. In Table 6, "Seikagaku" indicates SEIKAGAKU CORPORATION, "Vector" indicates Vector Laboratories, Inc., "AIST" indicates National Institute of Advanced Industrial Science and Technology, "Wako" indicates FUJIFILM Wako Pure Chemical Corporation, and "JOM" indicates J-OIL MILLS, Inc. Further, "For real-time PCR" indicates that it is SEQ ID NO of the base sequence used for the real-time PCR analysis in the experimental examples described later, and "For next generation sequencing" indicates that it is SEQ ID NO of the base sequence used for the next generation sequencing in the experimental examples described later.

TABLE 6

| Name of lectin | SEQ ID NO of amino acid sequence of lectin | Source of supply | SEQ ID NO of base sequence of labeled nucleic acid: For real-time PCR | SEQ ID NO of base sequence of labeled nucleic acid: For next generation sequencing |
|---|---|---|---|---|
| SNA | — | Seikagaku | 16 | 17 |
| ConA | — | Vector | 23 | 24 |
| GSLII | — | Vector | 18 | 19 |
| rBC2LCN | 1 | AIST | 8 | 9 |
| rAAL | 20 | AIST | 21 | 22 |
| rABA | 10 | AIST | 11 | 12 |
| rLSLN | 13 | AIST | 14 | 15 |
| rPSL1a | — | AIST | 25 | 26 |
| rDiscoidinI | — | AIST | 27 | 28 |
| rF17AG | — | AIST | 29 | 30 |
| rPVL | — | Wako | 31 | 32 |
| rCGL2 | — | AIST | 33 | 34 |
| rPAIL | — | AIST | 35 | 36 |
| rPPL | — | AIST | 37 | 38 |
| rRSIIL | — | AIST | 39 | 40 |
| rCNL | — | AIST | 41 | 42 |
| WFA | — | Vector | 43 | 44 |
| HPA | — | Seikagaku | 45 | 46 |
| SSA | — | Vector | 47 | 48 |
| rOrysata | — | AIST | 49 | 50 |
| rPALa | — | AIST | 51 | 52 |
| rDiscoidinII | — | AIST | 53 | 54 |
| CSA | — | JOM | 55 | 56 |
| rGRFT | — | AIST | 57 | 58 |
| rSRL | — | AIST | 59 | 60 |
| rAOL | — | AIST | — | 61 |
| rBanana | — | AIST | — | 62 |
| rBC2LA | — | AIST | — | 63 |

TABLE 6-continued

| Name of lectin | SEQ ID NO of amino acid sequence of lectin | Source of supply | SEQ ID NO of base sequence of labeled nucleic acid: For real-time PCR | SEQ ID NO of base sequence of labeled nucleic acid: For next generation sequencing |
|---|---|---|---|---|
| rC14 | — | AIST | — | 64 |
| rCalsepa | — | AIST | — | 65 |
| rGal3C | — | AIST | — | 66 |
| rGC2 | — | AIST | — | 67 |
| rMalectin | — | AIST | — | 68 |
| rMOA | — | AIST | — | 69 |
| rPTL | — | AIST | — | 70 |
| rRSL | — | AIST | — | 71 |
| TJAI | — | Vector | — | 72 |
| TJAII | — | Vector | — | 73 |
| UEAI | — | Vector | — | 74 |

Experimental Example 1

(Preparation of Nucleic Acid-Labeled Lectin 1)

A nucleic acid-labeled lectin was prepared. First, a fusion protein of a lectin and a nucleic acid binding domain was prepared. A BC2LCN lectin was used as the lectin. The amino acid sequence of BC2LCN lectin is set forth in SEQ ID NO: 1.

Further, as the nucleic acid binding domain, the following peptides were used; a peptide having four consecutive arginine residues (SEQ ID NO: 2, hereinafter referred to as "R4"), a peptide having five consecutive arginine residues (SEQ ID NO: 3, hereinafter referred to as "R5"), a peptide having six consecutive arginine residues (SEQ ID NO: 4, hereinafter referred to as "R6"), a peptide having seven consecutive arginine residues (SEQ ID NO: 5, hereinafter referred to as "R7"), a peptide having ten consecutive arginine residues (SEQ ID NO: 6, hereinafter referred to as "R10"), and an HMG Box A domain of mitochondrial transcription factor A (TFAM) (SEQ ID NO: 7, hereinafter referred to as "TFAM"). It is to be noted that it is known that arginine is basic and easily binds to a nucleic acid having a phosphoric acid moiety.

First, a fusion protein of a recombinant BC2LCN lectin (hereinafter referred to as "rBC2LCN") in which each nucleic acid binding domain was bound to the C-terminal side was expressed and purified in *Escherichia coli*. A FLAG tag was introduced on the N-terminal side of each fusion protein.

FIG. 1 is a photographic image showing the results of Coomassie Brilliant Blue (CBB) staining after separating each purified fusion protein by SDS-polyacrylamide gel electrophoresis (SDS-PAGE).

In FIG. 1, "M" indicates a molecular weight marker, "FLAG-rBC2LCN" indicates a fusion protein having no nucleic acid binding domain, "FLAG-rBC2LCN-R4" indicates a fusion protein linked with "R4". "FLAG-rBC2LCN-R5" indicates a fusion protein linked with "R5", "FLAG-rBC2LCN-R6" indicates a fusion protein linked with "R6", "FLAG-rBC2LCN-R7" indicates a fusion protein linked with "R7", "FLAG-rBC2LCN-R10" indicates a fusion protein linked with "R10", and "FLAG-rBC2LCN-TFAM" indicates a fusion protein linked with "TFAM".

Subsequently, the binding property of each purified fusion protein to the plasmid DNA (pCR2.1) was analyzed. Specifically, 1 μg of the plasmid DNA (pCR2.1) was mixed with 1, 2, 3, 4, or 5 μg of each fusion protein and subjected to agarose gel electrophoresis.

Figure 2:
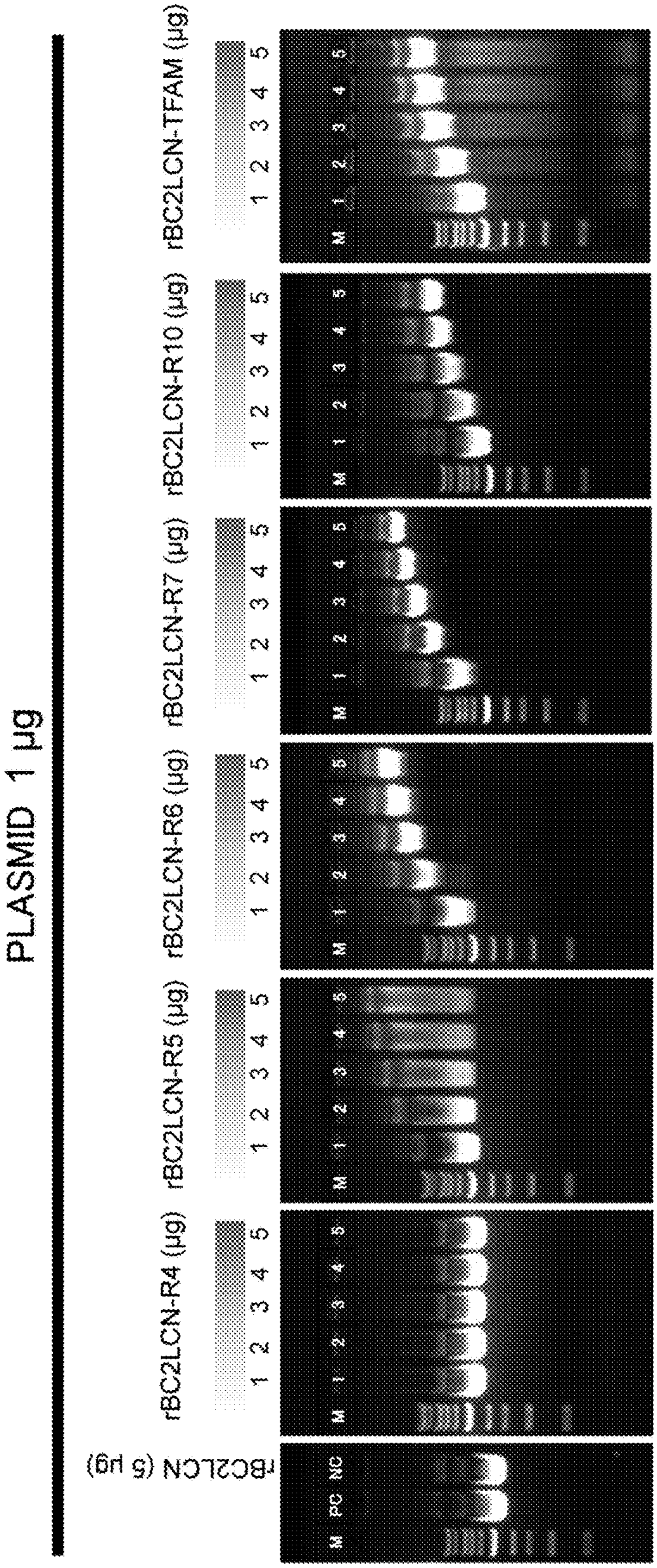
FIG. 2 is photographic images showing the results of agarose gel electrophoresis in Experimental Example 1.

FIG. 2 is photographic images showing the results of agarose gel electrophoresis. In FIG. 2, "M" indicates a molecular weight marker, "rBC2LCN" indicates a fusion protein having no nucleic acid binding domain, "rBC2LCN-R4" indicates a fusion protein linked with "R4". "rBC2LCN-R5" indicates a fusion protein linked with "R5", "rBC2LCN-R6" indicates a fusion protein linked with "R6", "rBC2LCN-R7" indicates a fusion protein linked with "R7", "rBC2LCN-R10" indicates a fusion protein linked with "R10", and "rBC2LCN-TFAM" indicates a fusion protein linked with "TFAM".

As a result, it was revealed that the fusion protein fused with 5 or more arginine residues or TFAM binds to the plasmid DNA. Therefore, it was revealed that a nucleic acid-labeled lectin can be prepared by mixing a nucleic acid with a fusion protein of a lectin and a nucleic acid binding domain.

Experimental Example 2

(Preparation of Nucleic Acid-Labeled Lectin 2)

A nucleic acid-labeled lectin was prepared using a commercially available kit (a Protein-oligo conjugation kit, catalog number: "S-9011-1", Solulink, Inc.).

In this kit, first, N-succinimidyl-4-formylbenzamide (hereinafter, referred to as "S-4FB") is bonded to an amino group of an oligonucleotide, in which the 5' terminal or 3' terminal is modified with the amino group, to prepare a 4-formylbenzamide (4FB)-modified oligonucleotide (a "4FB-oligonucleotide").

Further, succinimidyl-4-hydrazinonicotinate acetone hydrazone (hereinafter, referred to as "S-HyNic") is bonded to a protein to prepare a hydrazinonicotinate acetone hydrazone (HyNic)-modified protein (a "HyNic-protein").

Subsequently, in a case where the above 4FB-oligonucleotide and the above HyNic-protein are mixed, both can be covalently bonded to obtain a nucleic acid-labeled protein.

In the present experimental example, an oligonucleotide was bonded to rBC2LCN according to the instruction manual of the kit to prepare a nucleic acid-labeled lectin. rBC2LCN was used as the lectin. Further, an oligonucleotide having a base sequence set forth in SEQ ID NO: 8 was used as the nucleic acid.

Figure 3:
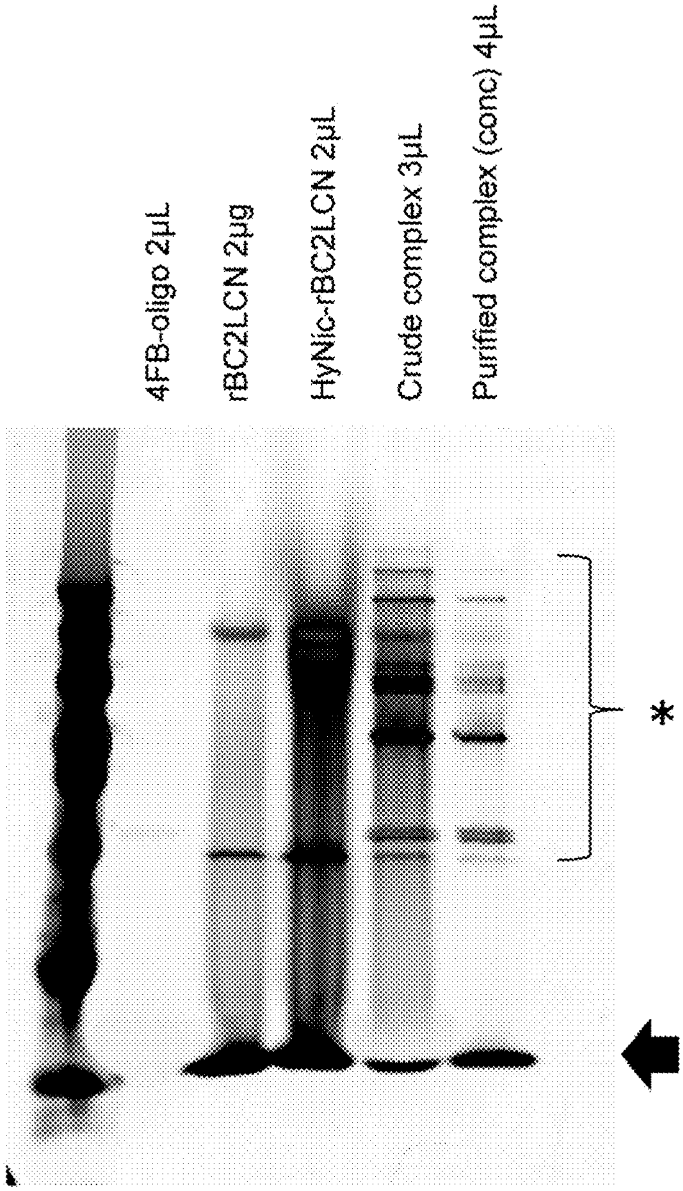
FIG. 3 is a photographic image showing the results obtained by subjecting specimens from each process of the preparation of nucleic acid-labeled lectin to SDS-PAGE and subjecting them to silver staining, in Experimental Example 2.

FIG. 3 is a photographic image showing the results obtained by subjecting specimens from each process of the preparation of nucleic acid-labeled lectin to SDS-PAGE and subjecting them to silver staining. In FIG. 3, "4FB-oligo" indicates a 4FB-modified oligonucleotide, "HyNic-rBC2LCN" indicates a HyNic-modified rBC2LCN, "Crude complex" indicates an unpurified reactant, and "Purified complex (conc)" indicates a purified and concentrated reactant. Further, "*" indicates rBC2LCN to which the oligonucleotide is bonded, and the arrow indicates rBC2LCN to which the oligonucleotide is not bonded.

As a result, rBC2LCN having an increased molecular weight due to the bonding of oligonucleotides was detected in the final product (the Purified complex (conc)). From this result, it was revealed that the nucleic acid-labeled lectin can be prepared by using a commercially available kit.

Experimental Example 3

(Preparation of Nucleic Acid-Labeled Lectin 3)

A nucleic acid-labeled lectin was prepared using the click reaction between an azide group and an alkyne group. Specifically, first, rBC2LCN was reacted with each of 15-fold, 30-fold, and 50-fold molar concentrations of dibenzocyclooctyne-N-hydroxysuccinimidyl ester (NHS-DBCO) at room temperature for 1 hour to be subjected to DBCO modification. Subsequently, each rBC2LCN subjected to DBCO modification was mixed with a 10-fold molar concentration of an azinated oligonucleotide (SEQ ID NO: 8) and reacted at 4° C. overnight. The oligonucleotide was subjected to the azination modification at the 5' terminal.

Figure 4:
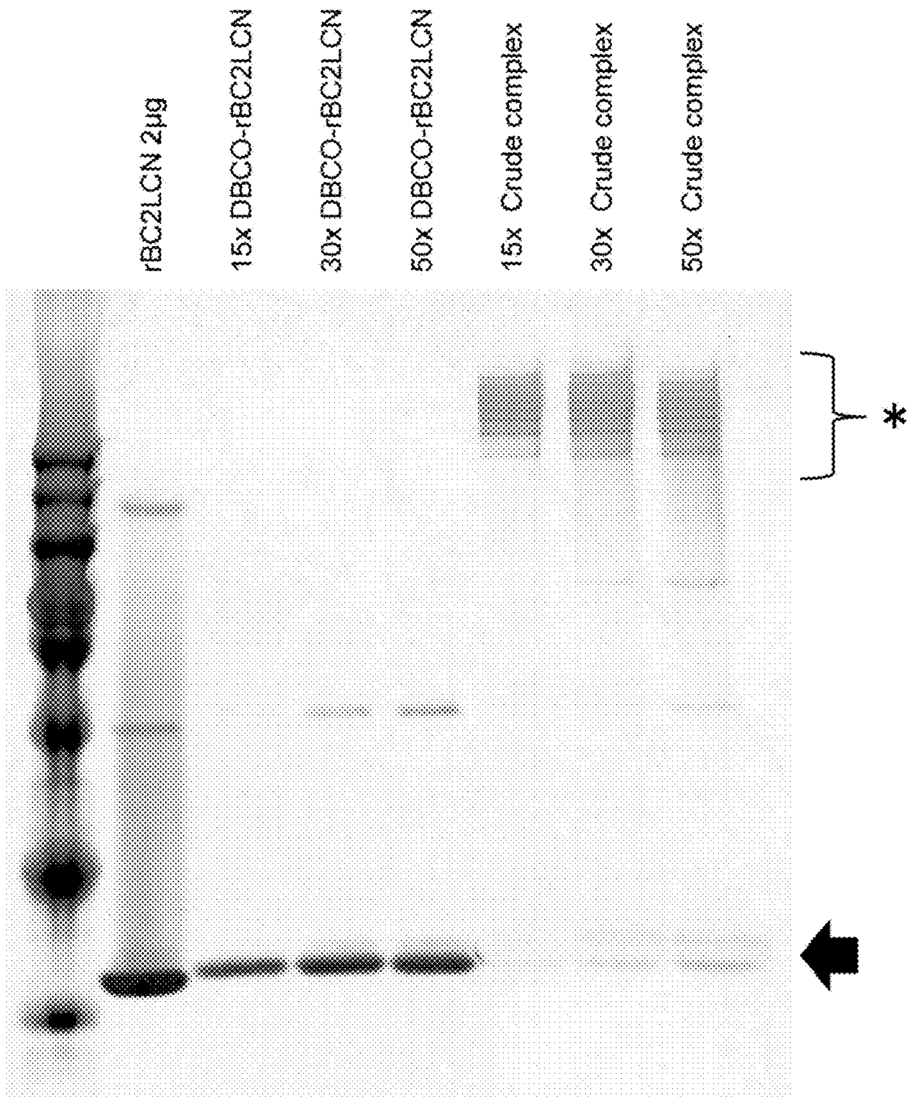
FIG. 4 is a photographic image showing the results obtained by subjecting specimens from each process of the preparation of nucleic acid-labeled lectin to SDS-PAGE and subjecting them to silver staining, in Experimental Example 3.

FIG. 4 is a photographic image showing the results obtained by subjecting specimens from each process to SDS-PAGE and subjecting them to silver staining. In FIG. 4, "DBCO-rBC2LCN" indicates rBC2LCN subjected to DBCO modification, "15×", "30×", and "50×" indicate that the corresponding result is obtained by the reaction with each of 15-fold, 30-fold, and 50-fold molar concentrations of NHS-DBCO, and "Crude complex" indicates an unpurified reactant. Further, "*" indicates rBC2LCN to which the oligonucleotide is bonded, and the arrow indicates rBC2LCN to which the oligonucleotide is not bonded.

As a result, rBC2LCN having an increased molecular weight due to the bonding of oligonucleotides was detected. From this result, it was revealed that the nucleic acid-labeled lectin can be efficiently prepared by the click reaction.

Experimental Example 4

(Preparation of Nucleic Acid-Labeled Lectin 4)

The click reaction between an azide group and an alkyne group was used to prepare a nucleic acid-labeled lectin. Specifically, first, rBC2LCN was reacted with a 2-fold molar concentration of dibenzocyclooctyne-N-hydroxysuccinimidyl ester (NHS-DBCO) at room temperature for 1 hour to be subjected to DBCO modification. Subsequently, rBC2LCN subjected to DBCO modification was mixed with a 10-fold molar concentration of an azinated oligonucleotide (SEQ ID NO: 8) and reacted at 4° C. overnight to obtain a nucleic acid-labeled lectin. The oligonucleotide was subjected to the azination modification at the 5' terminal. Subsequently, the nucleic acid-labeled lectin was purified by affinity chromatography using fucose Sepharose.

Figure 5:
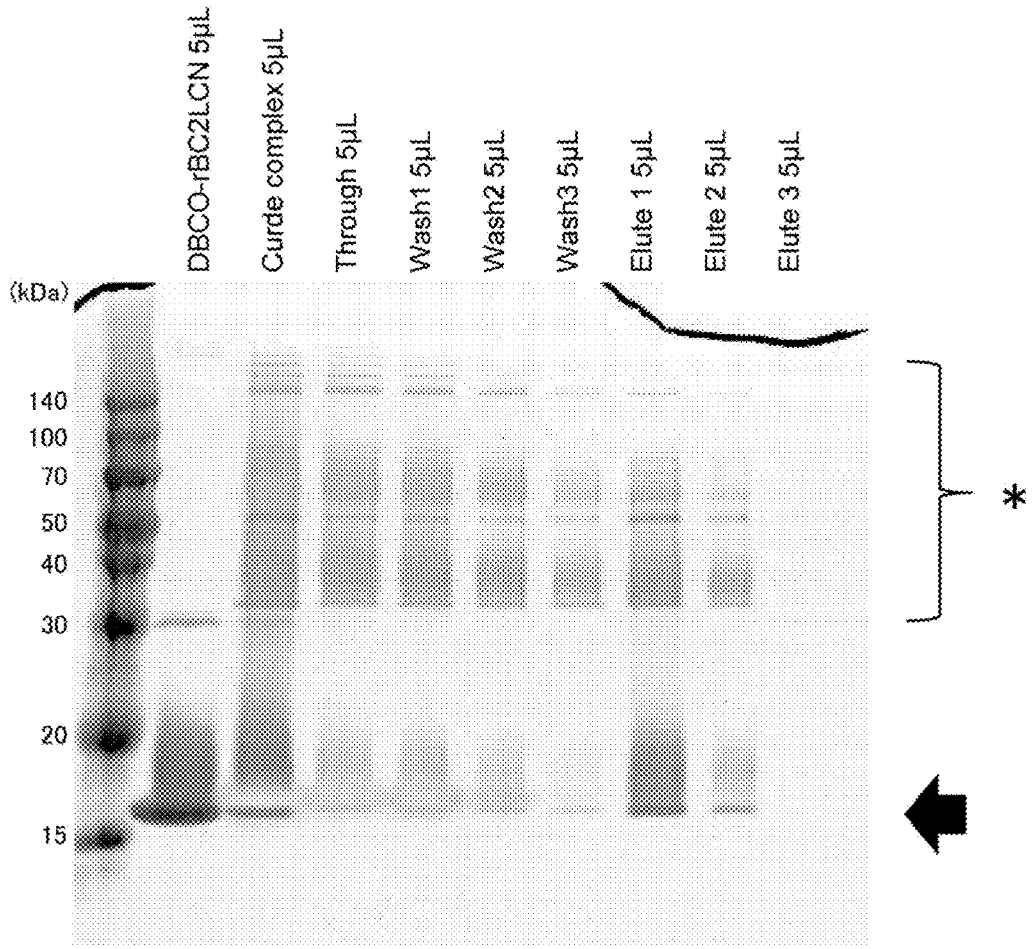
FIG. 5 is a photographic image showing the results obtained by subjecting specimens from each process of the purification of nucleic acid-labeled lectin to SDS-PAGE and subjecting them to silver staining, in Experimental Example 4.

FIG. 5 is a photographic image showing the results obtained by subjecting specimens from each process of the purification of nucleic acid-labeled lectin to SDS-PAGE and subjecting them to silver staining. In FIG. 5, "DBCO-rBC2LCN" indicates rBC2LCN subjected to DBCO modification, and "Crude complex" indicates an unpurified nucleic acid-labeled lectin. In addition, "Through" indicates a specimen that has passed through the affinity column, "Wash 1", "Wash 2", and "Wash 3" respectively indicate the first, second, and third washing solutions, and "Elute 1", "Elute 2", and "Elute 3" respectively indicate the first, second, and third elution solutions. Further, "*" indicates rBC2LCN to which the oligonucleotide is bonded, and the arrow indicates rBC2LCN to which the oligonucleotide is not bonded.

As a result, rBC2LCN having an increased molecular weight due to the bonding of oligonucleotides was detected. From this result, it was confirmed that a nucleic acid-labeled lectin can be prepared by the click reaction.

Subsequently, according to the same method as in rBC2LCN, each of nucleic acid-labeled lectins was prepared, where they were obtained by bonding the oligonucleotides shown in Table 6 to a recombinant (rABA) of an ABA lectin, a recombinant (rLSLN) of an LSLN lectin, an SNA lectin (catalog number: "L-1300", Vector Laboratories, Inc.), a GSLII lectin (catalog number: "L-1210", Vector Laboratories, Inc.), a recombinant (rAAL) of an AAL lectin, and concanavalin A (ConA, catalog number: "300036", SEIKAGAKU CORPORATION).

Each lectin was purified by affinity chromatography using Sepharose beads on which the sugar to which each lectin could be bound had been immobilized. Specifically, Sepharose beads on which N-acetylglucosamine had been immobilized were used for the purification of rABA, Sepharose beads on which galactose had been immobilized were used for the purification of rLSLN, Sepharose beads on which lactose had been immobilized were used for the purification of SNA, Sepharose beads on which N-acetylglucosamine had been immobilized were used for the purification of GSLII, Sepharose beads on which fucose had been immobilized were used for the purification of rAAL, and Sepharose beads on which mannose had been immobilized were used for the purification of ConA.

As a result of subjecting specimens from each process of the purification to SDS-PAGE and subjecting them to silver staining, it was confirmed that rABA, rLSLN, SNA, GSLII, rAAL, and ConA could be labeled with a nucleic acid.

Experimental Example 5

(Preparation of Nucleic Acid-Labeled Lectin 5)

The click reaction between an azide group and an alkyne group was used to prepare a nucleic acid-labeled lectin capable of releasing the nucleic acid upon irradiation with light. Specifically, first, a 16-fold molar concentration of an NHS-PC-DBCO ester (catalog number: "1160", Click Chemistry Tools, LLC) was reacted with rBC2LCN at room temperature for 1 hour to subject it to PC-DBCO modification.

Subsequently, rBC2LCN subjected to PC-DBCO modification was mixed with a 10-fold molar concentration of an azinated oligonucleotide (SEQ ID NO: 8) and reacted at 4° C. overnight to obtain a nucleic acid-labeled lectin. The oligonucleotide was subjected to the azination modification at the 5' terminal. Subsequently, the nucleic acid-labeled lectin was purified by affinity chromatography using fucose Sepharose.

Figure 6:
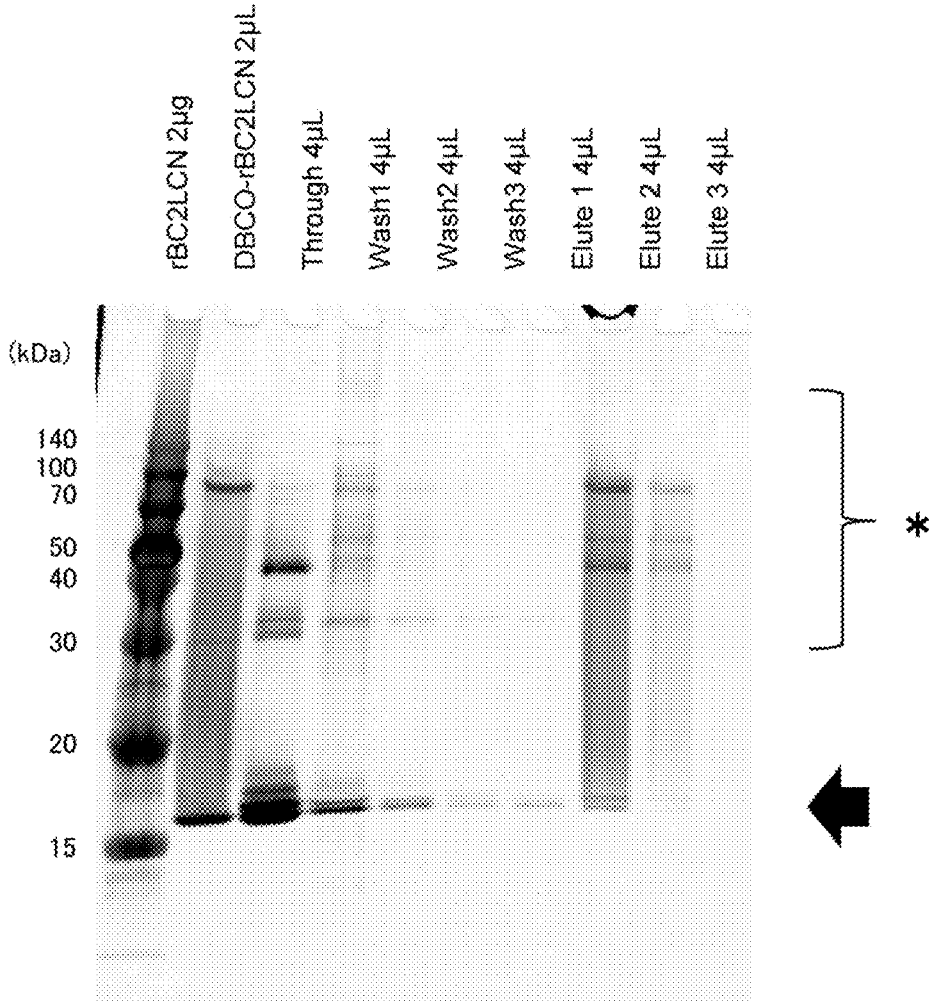
FIG. 6 is a photographic image showing the results obtained by subjecting specimens from each process of the purification of nucleic acid-labeled lectin to SDS-PAGE and subjecting them to silver staining, in Experimental Example 5.

FIG. 6 is a photographic image showing the results obtained by subjecting specimens from each process of the purification of nucleic acid-labeled lectin to SDS-PAGE and subjecting them to silver staining. In FIG. 5, "PC-DBCO-rBC2LCN" indicates rBC2LCN subjected to PC-DBCO modification, "Through" indicates a specimen that has passed through the affinity column, "Wash 1", "Wash 2", and "Wash 3" respectively indicate the first, second, and third washing solutions, and "Elute 1", "Elute 2", and "Elute 3" respectively indicate the first, second, and third elution solutions. Further, "*" indicates rBC2LCN to which the oligonucleotide is bonded, and the arrow indicates rBC2LCN to which the oligonucleotide is not bonded.

As a result, rBC2LCN having an increased molecular weight due to the bonding of oligonucleotides was detected. From this result, it was confirmed that a nucleic acid-labeled lectin capable of releasing the nucleic acid upon irradiation with light can be prepared by the click reaction.

Subsequently, according to the same method as in rBC2LCN, each of nucleic acid-labeled lectins was prepared, where they were obtained by cleavably bonding the oligonucleotides shown in Table 6 to rABA, rLSLN, an SNA lectin (catalog number: "L-1300", Vector Laboratories, Inc.), a GSLII lectin (catalog number: "L-1210", Vector Laboratories, Inc.), rAAL, and concanavalin A (ConA, catalog number: "300036", SEIKAGAKU CORPORATION) upon irradiation with light.

Each lectin was purified by affinity chromatography using Sepharose beads on which the sugar to which each lectin could be bound had been immobilized. As a result of subjecting specimens from each process of the purification to SDS-PAGE and subjecting them to silver staining, it was confirmed that each of the nucleotides could be cleavably bonded to rABA, rLSLN, SNA, GSLII, rAAL, and ConA upon irradiation with light.

Experimental Example 6

(Examination of Reaction Conditions Between Nucleic Acid-Labeled Lectin and Cell)

The reaction conditions between the nucleic acid-labeled lectin and cells were examined. Specifically, the nucleic acid-labeled lectin and cells were reacted and compared under the conditions of method 1 and method 2 below.

<<Method 1>>

As the nucleic acid-labeled lectin, a nucleic acid-labeled rBC2LCN lectin prepared in the same manner as in Experimental Example 4 was used. In addition, as the cell, a MIAPaCa-2 cell, a BxPC-3 cell, and a Capan-1 cell, all of which are cells derived from human pancreatic cancer, were used.

First, $1\times10^5$ cells of each of the above cells was suspended in each 100 μL of phosphate-buffered saline (PBS) containing 1% by mass of bovine serum albumin (BSA) (hereinafter, may be referred to as "BSA-PBS"). Subsequently, 100 ng of the nucleic acid-labeled rBC2LCN lectin was added to each cell suspension and reacted at 4° C. for 1 hour. Subsequently, each cell was washed 3 times with 1 mL of BSA-PBS and then suspended in 200 μL of BSA-PBS.

Subsequently, $1\times10^4$ live cells were placed in a new tube, centrifuged to remove the supernatant, 100 μL of 0.2 M fucose was added thereto and reacted at 4° C. for 30 minutes to release the nucleic acid-labeled rBC2LCN lectin from the cells. Subsequently, the supernatant was recovered by centrifugation at 15,000 rpm for 10 minutes, and the oligonucleotide bonded to the rBC2LCN lectin was quantified by real-time quantitative PCR.

For comparison, each cell was stained with an rBC2LCN lectin labeled with R-phycoerythrin, and the flow cytometric analysis was carried out.

<<Method 2>>

Method 2 was mainly different from method 1 in that the reaction between the nucleic acid-labeled lectin and cells was carried out in an OptiMEM culture medium rather than in BSA-PBS.

As the nucleic acid-labeled lectin and cells, the same ones as in Method 1 were used. First, $1\times10^5$ cells of each of the above cells were suspended in 100 μL of an OptiMEM culture medium (Thermo Fisher Scientific, Inc.). Subsequently, 100 ng of the nucleic acid-labeled rBC2LCN lectin was added to each cell suspension and reacted at 4° C. for 1 hour. Subsequently, each cell was washed 3 times with 1 mL of BSA-PBS and then suspended in 200 μL of PBS.

Subsequently, $1\times10^4$ live cells were placed in a new tube, centrifuged to remove the supernatant, 100 μL of 0.2 M fucose was added thereto and reacted at 4° C. for 30 minutes to release the nucleic acid-labeled rBC2LCN lectin from the cells.

Subsequently, the supernatant was recovered by centrifugation at 15,000 rpm for 10 minutes, and the oligonucleotide bonded to the rBC2LCN lectin was quantified by real-time quantitative PCR.

Figure 7A:
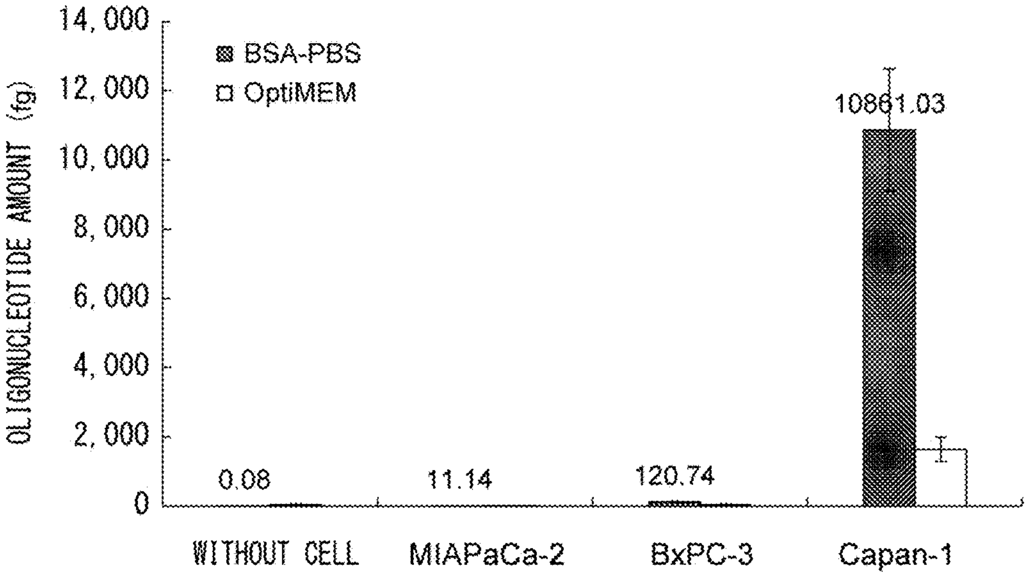
FIG. 7A is a graph showing the results of real-time quantitative PCR in Experimental Example 6.

FIG. 7A is a graph showing the results of real-time quantitative PCR. In FIG. 7A, "BSA-PBS" indicates the result of method 1, and "OptiMEM" indicates the result of method 2. As a result, it was revealed that the binding between the cell and the lectin can be detected with higher sensitivity in method 1.

Figure 7B:
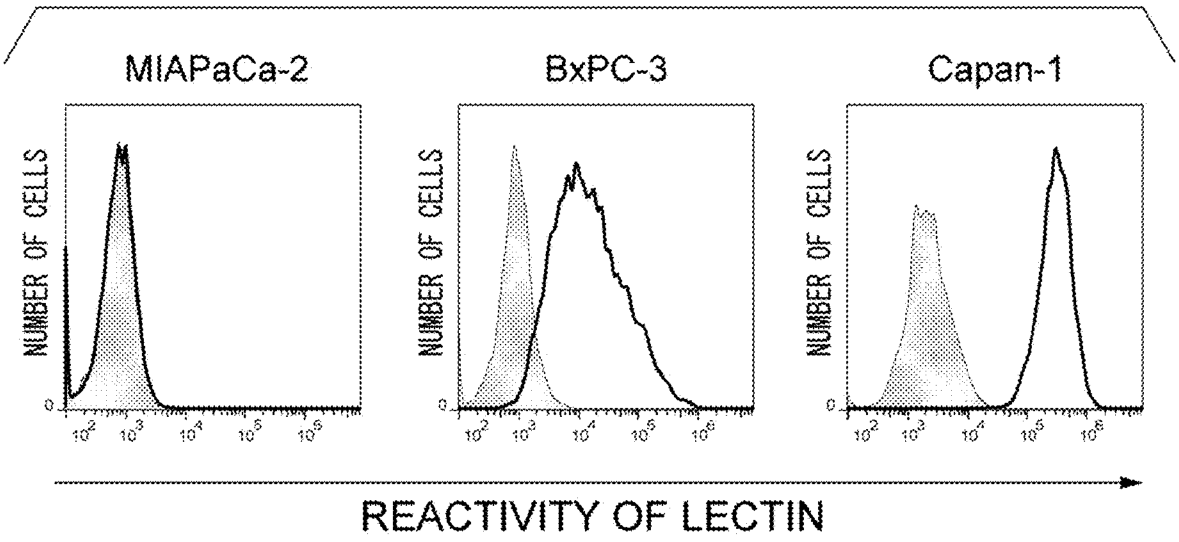
FIG. 7B is graphs showing the results of flow cytometric analysis in Experimental Example 6.

In addition, FIG. 7B is graphs showing the results of flow cytometric analysis. As a result, it was revealed that the analysis result from the real-time quantitative PCR shown in FIG. 7A is in agreement with the result of flow cytometric analysis, and the rBC2LCN lectin exhibits the highest reactivity to the Capan-1 cell, also reacts to the BxPC-3 cell, but does not react to the MIAPaCa-2 cell.

Experimental Example 7

(Examination of Nucleic Acid Release Conditions Upon Irradiation with Light)

The conditions for releasing the nucleic acid from the nucleic acid-labeled lectin capable of releasing the nucleic acid upon irradiation with light were examined. As the nucleic acid-labeled lectin, a nucleic acid-labeled rBC2LCN lectin prepared in the same manner as in Experimental Example 5 was used. In addition, as the cell, a Capan-1 cell, which is a cell derived from human pancreatic cancer, was used.

First, $1\times10^5$ cells were suspended in 100 µL of BSA-PBS. Subsequently, 100 ng of the nucleic acid-labeled rBC2LCN lectin was added to the cell suspension and reacted at 4° C. for 1 hour. Subsequently, the cells were washed 3 times with 1 mL of BSA-PBS and then suspended in 200 µL of BSA-PBS.

Subsequently, each aliquot of $1\times10^4$ cells was placed in a new tube, and an ultraviolet (UV) irradiation device (catalog number: "95-0042-14", Funakoshi Co., Ltd.) was used to carry out irradiation with ultraviolet rays having a peak wavelength at a wavelength of 365 nm at 15 W for 5 minutes, 10 minutes, or 15 minutes, thereby releasing the oligonucleotide. Subsequently, the supernatant was recovered by centrifugation at 15,000 rpm for 10 minutes, and the oligonucleotide bonded to the rBC2LCN lectin was quantified by real-time quantitative PCR.

For comparison, the oligonucleotide bonded to the rBC2LCN lectin was quantified by real-time quantitative PCR on a specimen of a supernatant recovered by immediate centrifugation without ultraviolet irradiation, a specimen of a supernatant recovered by centrifugation after allowing to stand at room temperature for 15 minutes without ultraviolet irradiation, and a specimen of a supernatant recovered by centrifugation after adding 100 µL of 0.2 M fucose to allow it to react at 4° C. for 15 minutes and releasing the nucleic acid-labeled rBC2LCN lectin from the cells.

Figure 8:
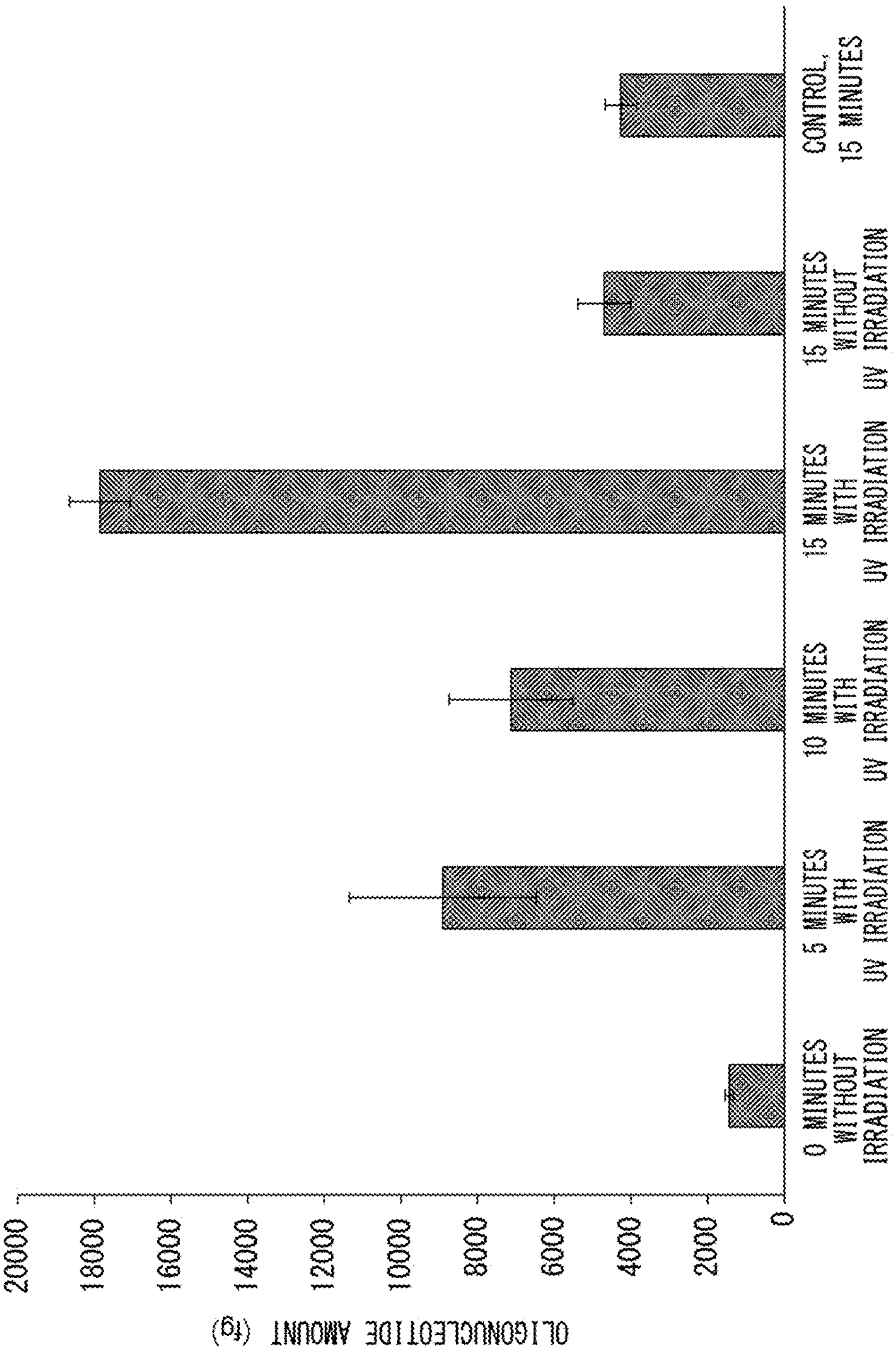
FIG. 8 is a graph showing the results of real-time quantitative PCR in Experimental Example 7.

FIG. 8 is a graph showing the results of real-time quantitative PCR. In FIG. 8, "0 minutes without irradiation" indicates the result of a specimen of a supernatant recovered by centrifuging at 15,000 rpm for 10 minutes without ultraviolet irradiation, "15 minutes without irradiation" indicates the result of a specimen of a supernatant recovered by centrifuging at 15,000 rpm for 10 minutes after allowing to stand at room temperature for 15 minutes without ultraviolet irradiation, and "Control, 15 minutes" indicates the result of a specimen of a supernatant recovered by centrifuging at 15,000 rpm for 10 minutes after adding 100 µL of 0.2 M fucose to allow it to react at 4° C. for 15 minutes to release the nucleic acid-labeled rBC2LCN lectin from the cells.

As a result, it was revealed that the largest number of oligonucleotides can be released in a case of being irradiated with ultraviolet rays for 15 minutes.

Experimental Example 8

(Examination of Reactivity of Nucleic Acid-Labeled Lectin 1)

It was examined whether or not there was a difference in the reactivity between an ordinary lectin not labeled with a nucleic acid and the nucleic acid-labeled lectin.

Specifically, each of the ordinary lectin (the unlabeled lectin) and the nucleic acid-labeled lectin was labeled with fluorescein isothiocyanate (FITC) and reacted with cells, and then flow cytometric analysis was carried out.

As the unlabeled lectin, GSLII, rABA, rBC2LCN, rLSLN, and SNA were used. As the nucleic acid-labeled lectin, nucleic acid-labeled bodies of the same lectins (GSLII, rABA, rBC2LCN, rLSLN, and SNA) as described above, prepared in the same manner as in Experimental Example 4, were used. As the cell, a SUIT-2 cell, an AsPC-1 cell, a BxPC-3 cell, a MIAPaCa-2 cell, and a Capan-1 cell, all of which are human pancreatic cancer-derived cells, were used.

First, each aliquot of $1\times10^5$ cells of each cell was suspended in 100 µL of BSA-PBS and dispensed into a tube. Subsequently, 100 ng of each of the unlabeled lectins (GSLII, rABA, rBC2LCN, rLSLN, and SNA) or nucleic acid-labeled lectins (GSLII, rABA, rBC2LCN, rLSLN, and SNA) was added to each cell suspension and reacted at 4° C. for 1 hour. Subsequently, each cell was washed 3 times with 1 mL of BSA-PBS and then suspended in 500 µL of BSA-PBS.

Figure 9A:
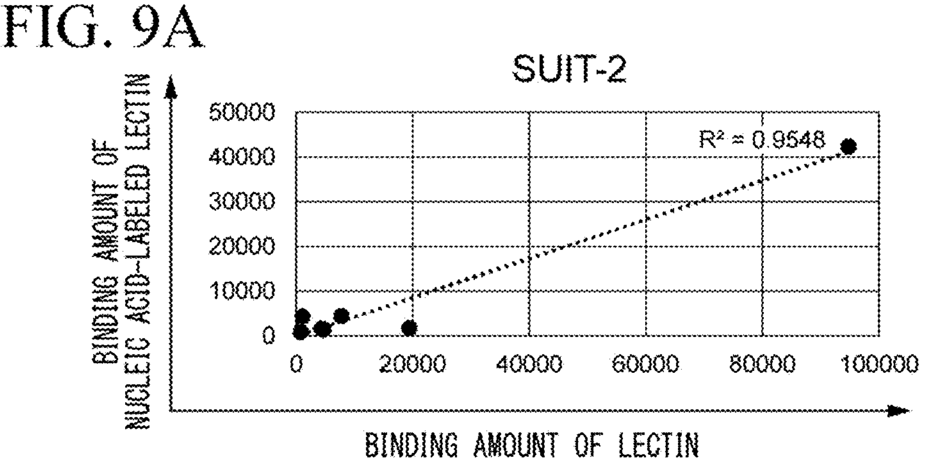
FIG. 9A is a graph showing the results of flow cytometric analysis in Experimental Example 8.
Figure 9B:
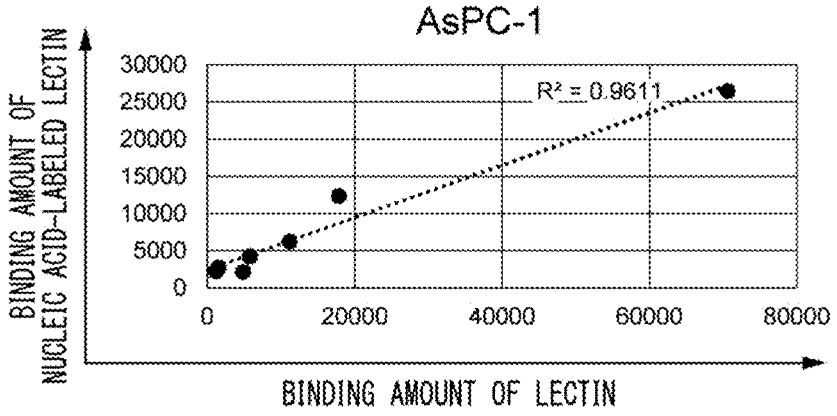
FIG. 9B is graph showing the results of flow cytometric analysis in Experimental Example 8.
Figure 9C:
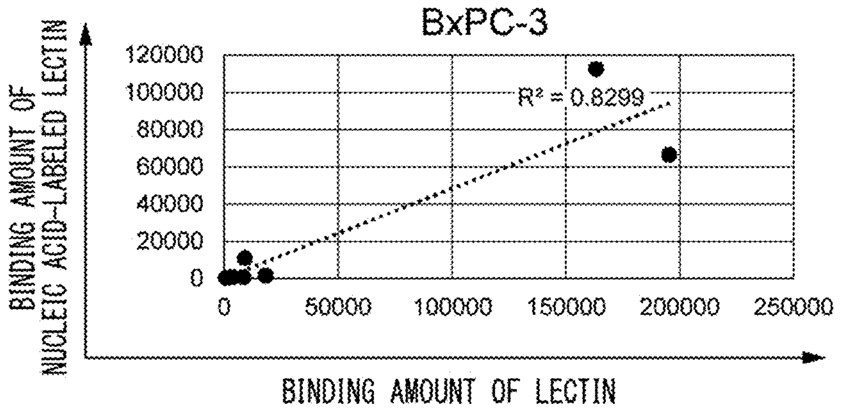
FIG. 9C is a graph showing the results of flow cytometric analysis in Experimental Example 8.
Figure 9D:
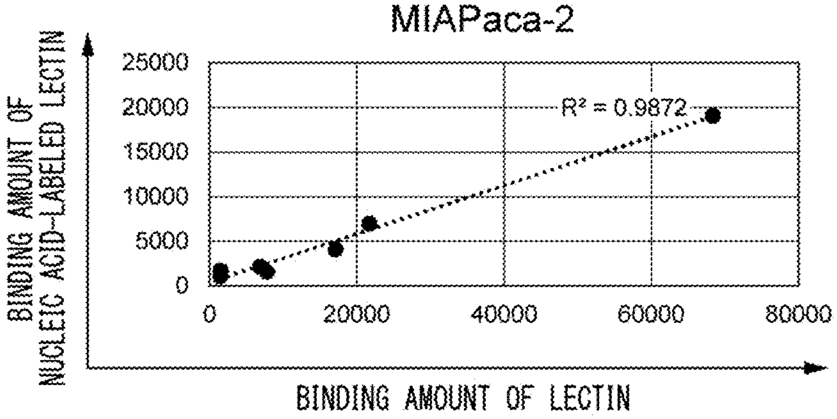
FIG. 9D is a graph showing the results of flow cytometric analysis in Experimental Example 8.
Figure 9E:
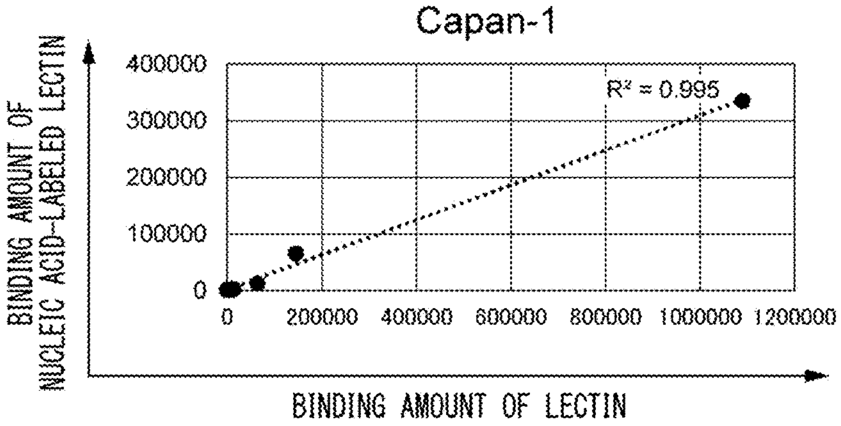
FIG. 9E is graph showing the results of flow cytometric analysis in Experimental Example 8.

Subsequently, each cell was subjected to flow cytometric analysis, the amount of each lectin bound to the cell was measured, and the correlation of the reactivity between the unlabeled body and the nucleic acid labeled body was investigated for each lectin. FIG. 9A to FIG. 9E are graphs showing the results of flow cytometric analysis. FIG. 9A is the result of the SUIT-2 cell, FIG. 9B is the result of the AsPC-1 cell, FIG. 9C is the result of the BxPC-3 cell, FIG. 9D is the result of the MIAPaCa-2 cell, and FIG. 9E is the result of the Capan-1 cell. Further, in FIG. 9A to FIG. 9E, the lateral axis indicates the binding amount (the average fluorescence intensity) of the unlabeled lectins (GSLII, rABA, rBC2LCN, rLSLN, and SNA), and the vertical axis indicates the binding amount (the average fluorescence intensity) of the nucleic acid-labeled lectins (GSLII, rABA, rBC2LCN, rLSLN, and SNA).

As a result, it was revealed that the reactivity of the unlabeled lectin and the reactivity of the nucleic acid-labeled lectin to each cell each show a high correlation. From this result, it was confirmed that the reactivity of the lectin does not change even in a case where the lectin is labeled with a nucleic acid.

Experimental Example 9

(Examination of Reactivity of Nucleic Acid-Labeled Lectin 2)

The nucleic acid-labeled lectin was reacted with cells, and the binding amount thereof was measured and compared by flow cytometric analysis and real-time quantitative PCR analysis.

As the nucleic acid-labeled lectin, nucleic acid-labeled lectins (GSLII, rABA, rBC2LCN, rLSLN, and SNA) prepared in the same manner as in Experimental Example 5 and capable of releasing the nucleic acid upon irradiation with light were used. In addition, as the cell, a Capan-1 cell, which is a cell derived from human pancreatic cancer, was used.

First, each aliquot of $1\times10^5$ cells was suspended in 100 μL of BSA-PBS and dispensed into a tube. Subsequently, 100 ng of the nucleic acid-labeled lectins (GSLII, rABA, rBC2LCN, rLSLN, and SNA) were added to each cell suspension and reacted at 4° C. for 1 hour. Subsequently, each cell was washed 3 times with 1 mL of BSA-PBS and then suspended in 500 μL of BSA-PBS.

Subsequently, some cells were subjected to flow cytometric analysis, and the remainder were subjected to real-time quantitative PCR to measure the amount of lectin bound to the cell. Real-time quantitative PCR was carried out as follows. First, an ultraviolet (UV) irradiation device (catalog number: "95-0042-14", Funakoshi Co., Ltd.) was used to irradiate a part of cells with ultraviolet rays having a peak wavelength at a wavelength of 365 nm at 15 W for 15 minutes, thereby releasing the oligonucleotide. Subsequently, the supernatant was recovered by centrifugation at 15,000 rpm for 10 minutes, and the oligonucleotide released was quantified by real-time quantitative PCR.

Figure 10:
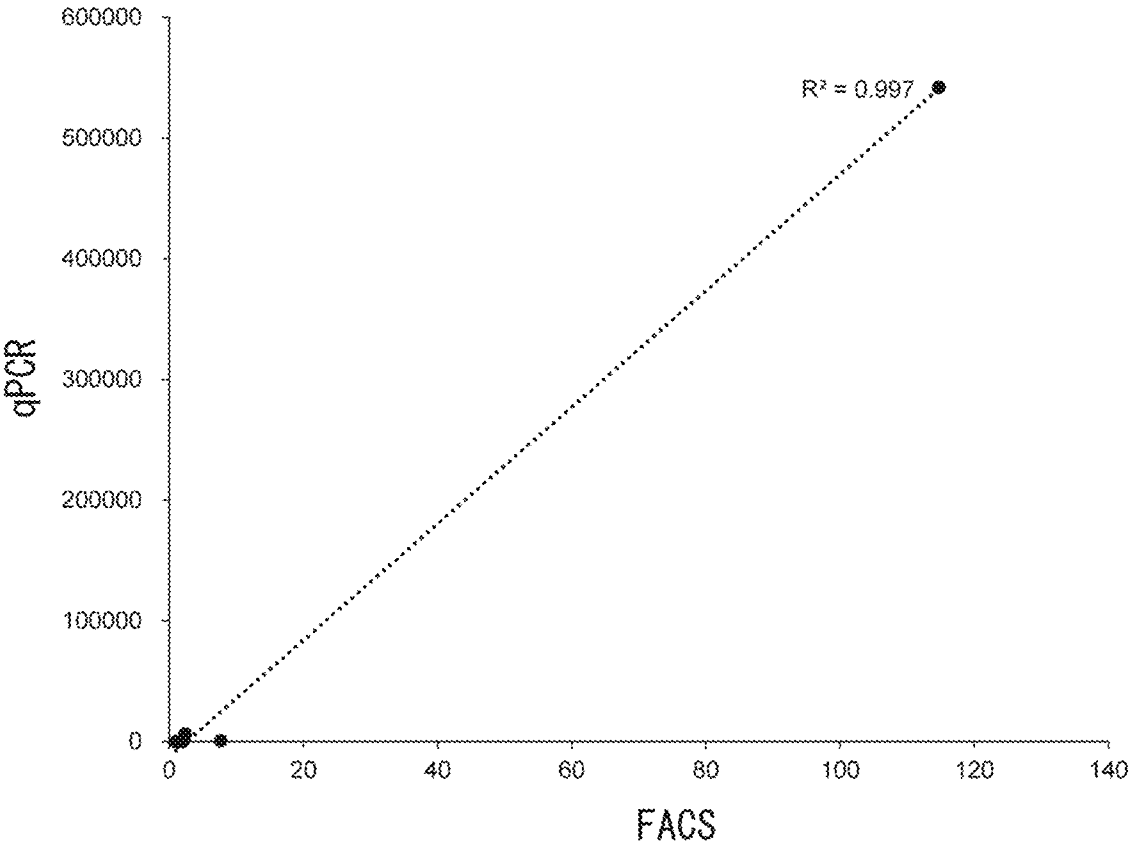
FIG. 10 is a graph showing the results of flow cytometric analysis and real-time quantitative PCR in Experimental Example 9.

FIG. 10 is a graph showing the results of flow cytometric analysis and real-time quantitative PCR. In FIG. 10, "qPCR" indicates the result of real-time quantitative PCR (the oligonucleotide amount), and "FACS" indicates the result of flow cytometric analysis (the average fluorescence intensity).

As a result, it was revealed that the result of flow cytometric analysis and the result of real-time quantitative PCR show a high correlation. From this result, it was revealed that the same result as the flow cytometric analysis can be obtained by real-time quantitative PCR using a nucleic acid-labeled lectin.

Experimental Example 10

(Examination of Reactivity of Nucleic Acid-Labeled Lectin 3)

A plurality of kinds of lectins were reacted with cells, and the binding of the lectins was analyzed by flow cytometric analysis and real-time quantitative PCR. Specifically, GSLII, rABA, rBC2LCN, rLSLN, and SNA, each labeled with fluorescein isothiocyanate (FITC), were each reacted with the Capan-1 cell, and the flow cytometric analysis was carried out.

First, each aliquot of $1\times10^5$ cells of the Capan-1 cell was suspended in 100 μL of BSA-PBS and dispensed into a tube. Subsequently, 100 ng of each FITC-labeled lectin was added to each cell suspension and reacted at 4° C. for 1 hour. Subsequently, each cell was washed 3 times with 1 mL of BSA-PBS and then suspended in 200 μL of BSA-PBS. Subsequently, each cell was subjected to flow cytometric analysis, and the amount of each lectin bound to the cell was measured.

In addition, each of GSLII, rABA, rBC2LCN, rLSLN, and SNA, which were subjected to nucleic acid labeling in the same manner as in Experimental Example 5, was reacted with the Capan-1 cell, and the bound lectin was measured by real-time quantitative PCR.

Specifically, each aliquot of $1\times10^5$ cells of the Capan-1 cell was suspended in 100 μL of BSA-PBS and dispensed into a tube. Subsequently, 100 ng of each nucleic acid-labeled lectin was added to each cell suspension and reacted at 4° C. for 1 hour. Subsequently, each cell was washed 3 times with 1 mL of BSA-PBS and then suspended in 500 μL of BSA-PBS.

Subsequently, an ultraviolet (UV) irradiation device (catalog number: "95-0042-14", Funakoshi Co., Ltd.) was used to irradiate each cell with ultraviolet rays having a peak wavelength at a wavelength of 365 nm at 15 W for 15 minutes, thereby releasing the oligonucleotide. Subsequently, the supernatant was recovered by centrifugation at 15,000 rpm for 10 minutes, and each oligonucleotide released was quantified by real-time quantitative PCR.

Figure 11A:
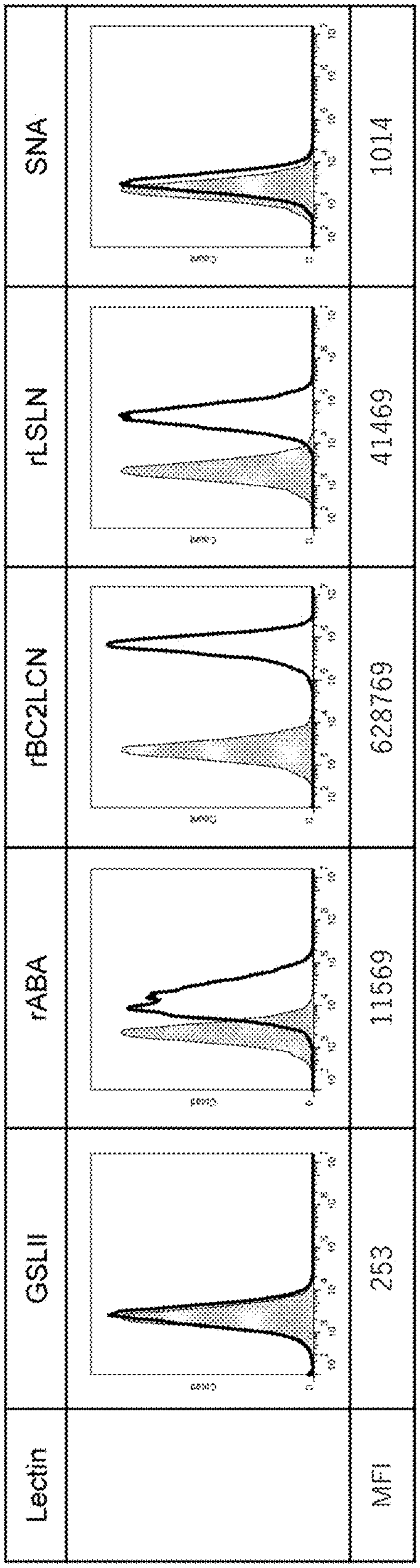
FIG. 11A is graphs showing the results of flow cytometric analysis in Experimental Example 10.
Figure 11B:
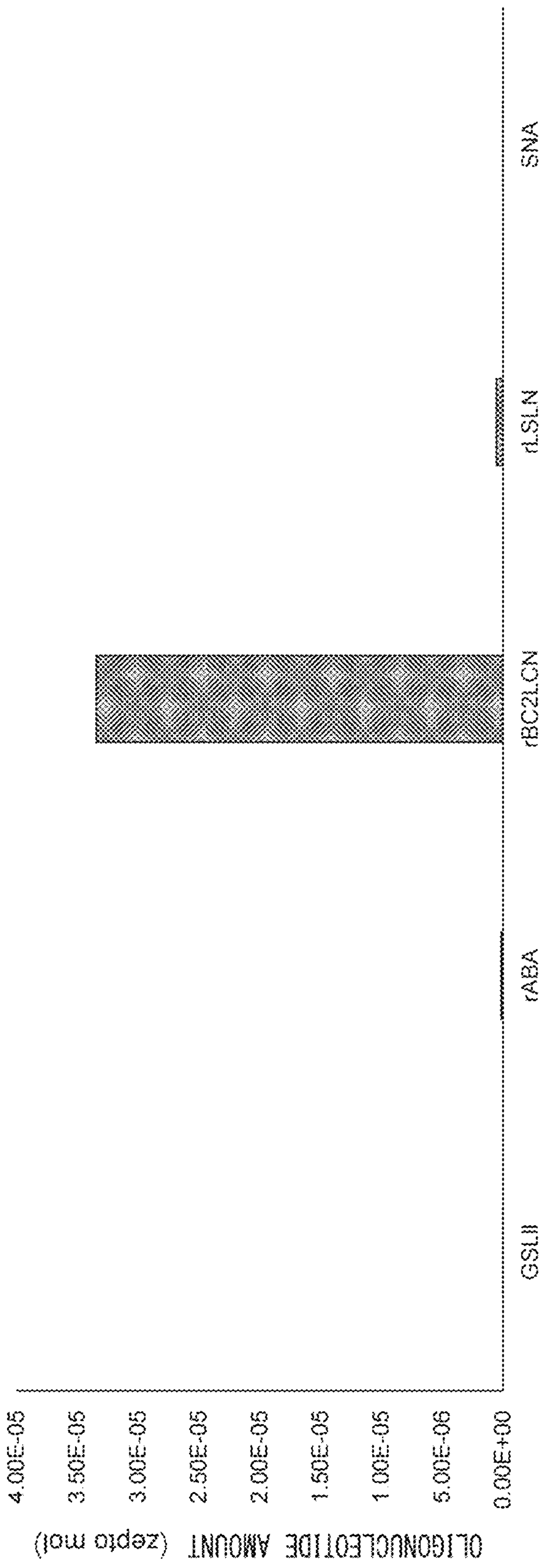
FIG. 11B is a graph showing the results of real-time quantitative PCR in Experimental Example 10.
Figure 12:
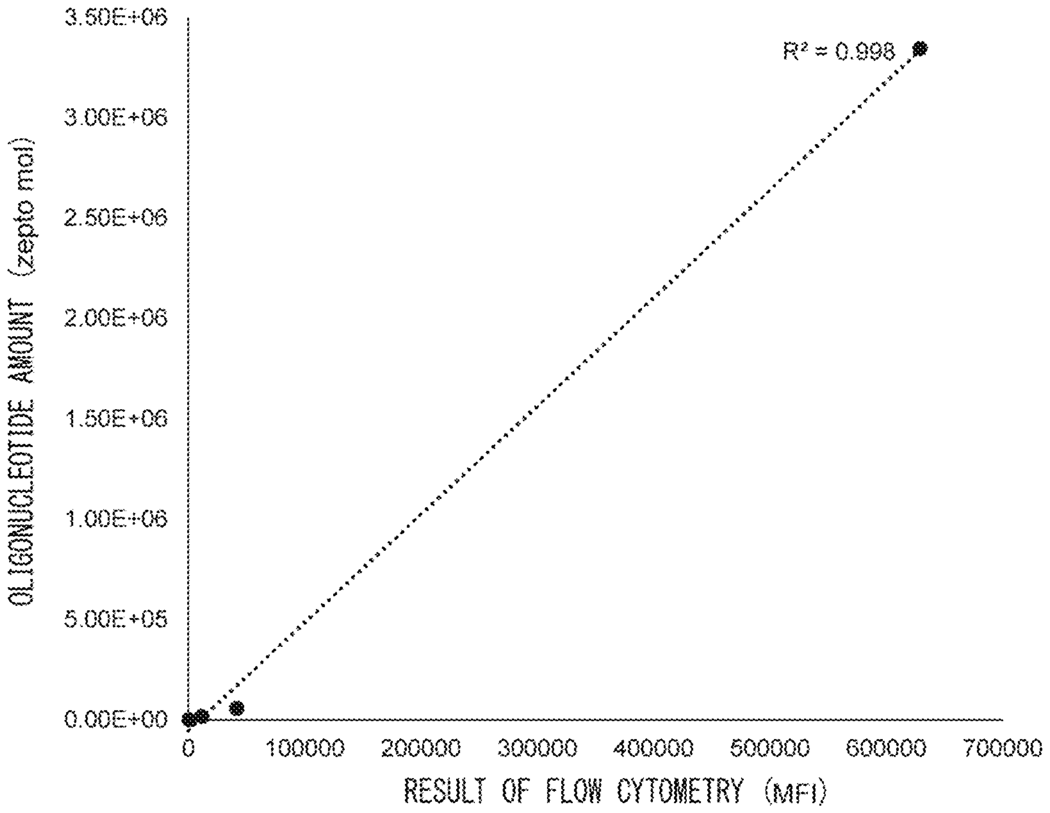
FIG. 12 is a graph showing the results of flow cytometric analysis on the lateral axis and the results of real-time quantitative PCR on the vertical axis based on the results of FIG. 11A and FIG. 11B.

FIG. 11A is graphs showing the results of flow cytometric analysis. In FIG. 11A, "MFI" indicates the average value of the measured fluorescence intensities. In addition, FIG. 11B is a graph showing the results of real-time quantitative PCR. In addition, FIG. 12 is a graph showing the results of flow cytometric analysis on the lateral axis and the results of real-time quantitative PCR on the vertical axis based on the results of FIG. 11A and FIG. 11B.

As a result, it was confirmed that the results of flow cytometric analysis and the result of real-time quantitative PCR show a high correlation. These results further support that the binding of the lectin to the cell can be analyzed by reacting the nucleic acid-labeled lectin with cells and detecting the nucleic acid bonded to the nucleic acid-labeled lectin.

Experimental Example 11

(Examination of Reactivity of Nucleic Acid-Labeled Lectin 4)

The nucleic acid-labeled lectin was reacted with serially diluted cells and the binding amount thereof was measured by real-time quantitative PCR analysis.

As the nucleic acid-labeled lectin, a nucleic acid-labeled lectin rBC2LCN lectin prepared in the same manner as in Experimental Example 5 and capable of releasing the nucleic acid upon irradiation with light was used. In addition, as the cell, a Capan-1 cell, which is a cell derived from human pancreatic cancer, was used.

First, 10,000 cells, 1,000, 100 cells, 10 cells, 1 cell, and 0 cells of the Capan-1 cell were each suspended in 100 μL of BSA-PBS and placed in a tube. Subsequently, 100 ng of the nucleic acid-labeled rBC2LCN lectin was added to each cell suspension and reacted at 4° C. for 1 hour. Subsequently, each cell was washed 3 times with 1 mL of BSA-PBS and then suspended in 200 μL of BSA-PBS.

Subsequently, an ultraviolet (UV) irradiation device (catalog number: "95-0042-14", Funakoshi Co., Ltd.) was used to irradiate each cell with ultraviolet rays having a peak wavelength at a wavelength of 365 nm at 15 W for 15 minutes, thereby releasing the oligonucleotide. Subsequently, the supernatant was recovered by centrifugation at 15,000 rpm for 10 minutes, and each oligonucleotide released was quantified by real-time quantitative PCR.

Figure 13:
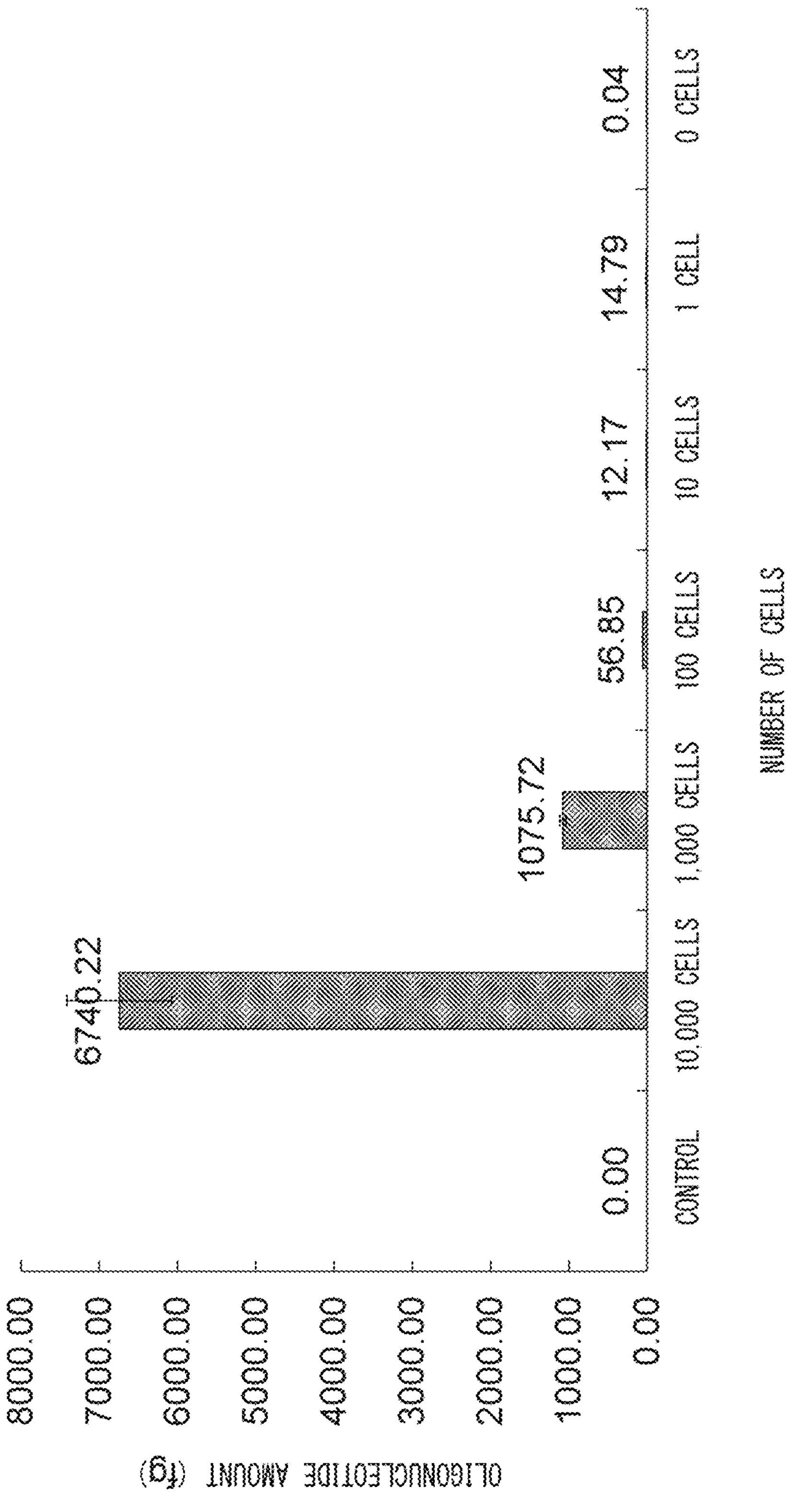
FIG. 13 is a graph showing the results of real-time quantitative PCR in Experimental Example 11.

FIG. 13 is a graph showing the results of real-time quantitative PCR. In FIG. 13, "Control" is the result of a specimen obtained by undergoing a series of reactions without adding the nucleic acid-labeled rBC2LCN lectin. As a result, it was revealed that the binding of the lectin to even a single cell can be analyzed by reacting the nucleic acid-labeled lectin with cells and detecting the nucleic acid bonded to the nucleic acid-labeled lectin.

Experimental Example 12

(Examination of Reactivity of Nucleic Acid-Labeled Lectin 5)

A mixture of a plurality of kinds of nucleic acid-labeled lectins was reacted with 100,000 cells, and the nucleic acid bound to 10,000 cells among them was analyzed using a next generation sequencer. Nucleic acid-labeled lectins (SNA, ConA, GSLII, rBC2LCN, rAAL, rABA, rLSLN, rPSL1a, rDiscoidin I, rF17AG, rPVL, rCGL2, rPAIL, rPPL, rRSIIL, rCNL, WFA, HPA, SSA, rOrysata, rPALa, rDiscoidin II, CSA, rGRFT, rSRL, rAOL, rBanana, rBC2LA, rC14, rCalsepa, rGal3C, rGC2, rMalectin, rMOA, rPTL, rRSL, TJAI, TJAII, and, UEAI) prepared in the same manner as in Experimental Example 4 were used as the nucleic acid-labeled lectin, and a podocalyxin (PODXL) antibody (manufactured by R&D Systems, Inc.) was used. In addition, as the cell, a Capan-1 cell, a BxPC-3 cell, a PANC-1 cell, and an AsPC1 cell, which are cells derived from human pancreatic cancer, as well as a CHO cell and Lec1, Lec2, and Lec8, which are mutant cells of the CHO cell, were used.

First, each aliquot of 100,000 cells of each cell was suspended in 100 μL of BSA-PBS and dispensed into a tube. Subsequently, 50 ng of each nucleic acid-labeled lectin was added to each cell suspension and reacted at 4° C. for 1 hour. Subsequently, each cell was washed 3 times with 1 mL of BSA-PBS and then suspended in 200 μL of BSA-PBS. Subsequently, the number of cells was measured, and 10,000 were transferred to a new tube. Subsequently, the supernatant was removed by centrifugation, and then the cells were suspended in 100 μL PBS. Subsequently, an ultraviolet (UV) irradiation device (catalog number: "95-0042-14", Funakoshi Co., Ltd.) was used to carry out irradiation with ultraviolet rays having a peak wavelength at a wavelength of 365 nm at 15 W for 15 minutes and to release the oligonucleotide, thereby recovering the supernatant after centrifugation. Subsequently, a PCR reaction was carried out using this as a template, and the analysis was carried out using a next generation sequencer.

The following operations were carried out in a case of carrying out the sequencing with the next generation sequencer. PCR was carried out with an IS index primer (SEQ ID NO: 75) and an 17 index primer (SEQ ID NO: 76), the amplified PCR product was purified and concentrated, and then the degree of purification and the concentration thereof were checked with a microchip electrophoresis device for DNA/RNA analysis (Shimadzu Corporation). Subsequently, the base sequence of the nucleic acid labeled to the nucleic acid-labeled lectin bound to each cell was sequenced using a next generation sequencer (product name: "MiSeq", Illumina, Inc.), and the number of reads of the detected base sequence was totaled. Further, "nnnnnnnn" in SEQ ID NOs: 75 and 76 (here, "n" indicates "a", "t", "g", or "c") has a different sequence for each cell, which is used for identification of cells.

Figure 14:
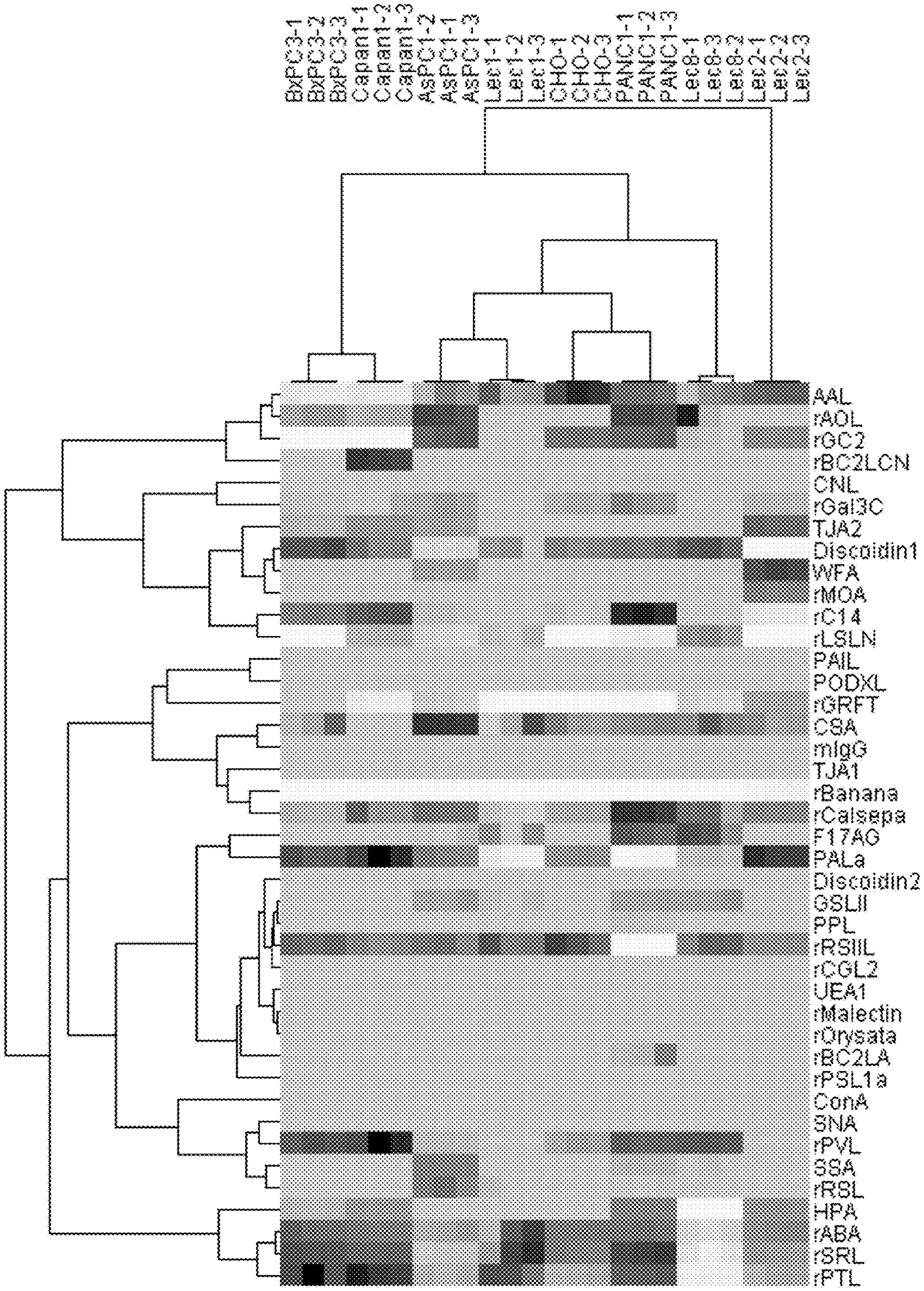
FIG. 14 is a diagram showing the results of Experimental Example 12.

FIG. 14 is a diagram showing the results of cluster analysis using the number of reads of the base sequence of the nucleic acid labeled to each lectin.

As a result, it was revealed that the binding of the lectin to the cell can be analyzed by reacting the nucleic acid-labeled lectin with 10,000 cells and sequencing the nucleic acid bonded to the nucleic acid-labeled lectin with a next generation sequencer. Further, it was revealed that the pattern of the reaction with the lectin was different in each cell.

Experimental Example 13

(Examination of Reactivity of Nucleic Acid-Labeled Lectin 6)

Each mixture of a plurality of kinds of nucleic acid-labeled lectins was reacted with 10,000 cells and a single cell, and the binding thereof was analyzed using a next generation sequencer. Nucleic acid-labeled lectins (SNA, ConA, GSLII, rBC2LCN, rAAL, rABA, rLSLN, rPSL1a, rDiscoidin I, rF17AG, rPVL, rCGL2, rPAIL, rPPL, rRSIIL, rCNL, WFA, HPA, SSA, rOrysata, rPALa, rDiscoidin II, CSA, rGRFT, rSRL, rAOL, rBanana, rBC2LA, rC14, rCalsepa, rGal3C, rGC2, rMalectin, rMOA, rPTL, rRSL, TJAI, TJAII, and, UEAD prepared in the same manner as in Example 4 were used as the nucleic acid-labeled lectin, and a podocalyxin (PODXL) antibody was used. In addition, as the cell, 201B7, which is a human iPS cell line, was used.

First, each aliquot of 100,000 cells of the human iPS cell was suspended in 100 μL of BSA-PBS and dispensed into a tube. Subsequently, 0.5 ng of each nucleic acid-labeled lectin was added to each cell suspension and reacted at 4° C. for 1 hour. Subsequently, the cells were washed 3 times with 1 mL of BSA-PBS and then suspended in 200 μL of BSA-PBS.

Subsequently, 10,000 cells and a single cell were dispensed, the base sequence of the nucleic acid labeled to the nucleic acid-labeled lectin bound to each cell was sequenced using a next generation sequencer (product name: "MiSeq", Illumina, Inc.), and the number of reads of the detected base sequence was totaled.

Figure 15:
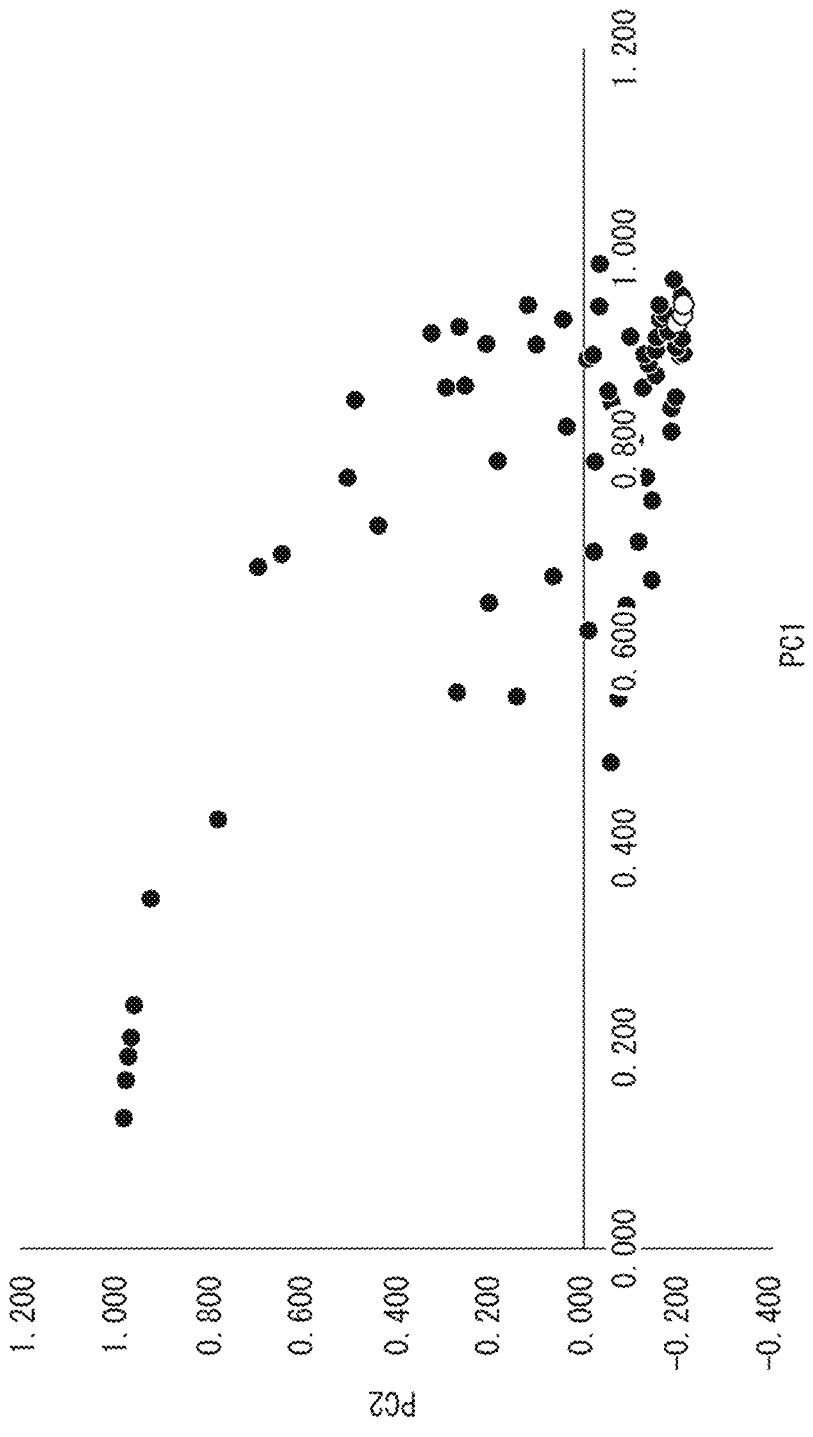
FIG. 15 is a graph showing the results of Experimental Example 13.

FIG. 15 is a graph showing the results obtained by subjecting the obtained number of reads to the main component analysis. In FIG. 15, "PC1" indicates a Principal component 1 (a main component 1), and "PC2" indicates a Principal component 2 (a main component 2). In the graph, black circles indicate the results of the analysis at a single cell level, and white circles indicate the results of the analysis at the level of 10,000 cells.

As a result, it was revealed that the binding of the lectin to the cell can be analyzed at a single cell level by reacting a mixture of the nucleic acid-labeled lectins with cells and sequencing the nucleic acid bonded to the nucleic acid-labeled lectin with a next generation sequencer. In addition, it was revealed that although the analysis result at a single cell level is similar to the analysis result of 10,000 cells, this cell population has considerably heterogeneous glycans.

Experimental Example 14

(Examination of Reactivity of Nucleic Acid-Labeled Lectin 7)

Each mixture of a plurality of kinds of nucleic acid-labeled lectins was reacted with 10,000 cells of the microorganism, and the binding thereof was analyzed using a next generation sequencer. Nucleic acid-labeled lectins (rBC2LCN, rAAL, rABA, rLSLN, rPSL1a, rDiscoidin I, rF17AG, rPVL, rCGL2, rPAIL, rPPL, rRSIIL, rCNL, WFA, HPA, SSA, rOrysata, rPALa, and rDiscoidin II) prepared in the same manner as in Example 4 were used as the nucleic acid-labeled lectin. As the microorganism, *Escherichia coli*, Deinococcus radiodurans, and budding yeast (*Saccharomyces cerevisiae*) were used.

First, each aliquot of 1,000,000 cells of each microorganism was suspended in 100 μL of BSA-PBS and dispensed into a tube. Subsequently, 0.5 ng of each nucleic acid-labeled lectin was added to each cell suspension and reacted at 4° C. for 1 hour. Subsequently, each microorganism was washed 3 times with 1 mL of BSA-PBS and then suspended in 200 μL of BSA-PBS.

Subsequently, 100,000 microorganisms of each microorganism were dispensed, the base sequence of the nucleic acid labeled to the nucleic acid-labeled lectin bound to each microorganism was sequenced using a next generation sequencer (product name: "MiSeq", Illumina, Inc.), and the number of reads of the detected base sequence was totaled. The sequencing was independently carried out 3 times for each microorganism.

Figure 16:
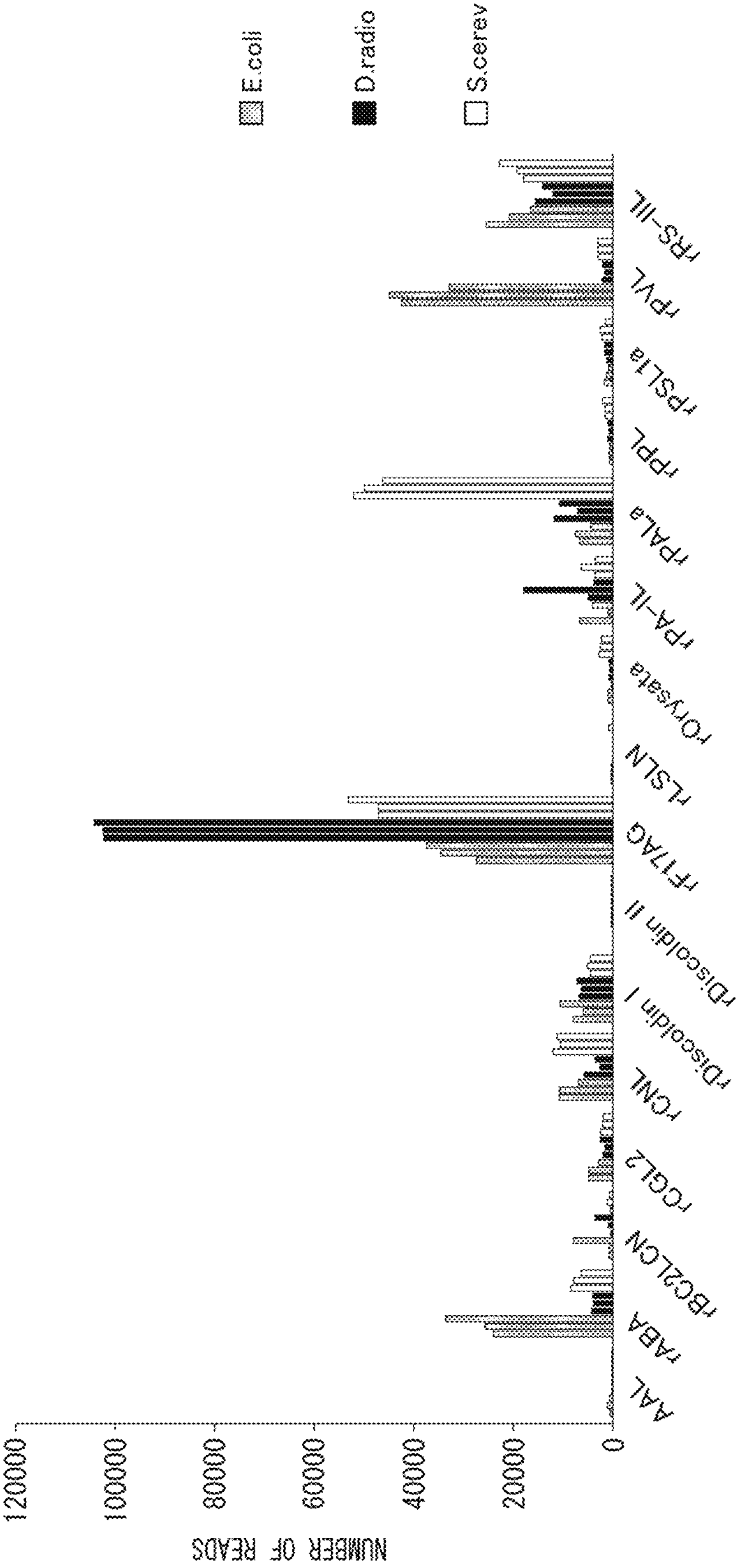
FIG. 16 is a graph showing the results of Experimental Example 14.

FIG. 16 is a graph showing the number of reads of the base sequence of the nucleic acid labeled to each lectin. In FIG. 16, "*E. coli*" indicates *Escherichia coli*, "D. radio" indicates Deinococcus radiodurans, and "*S. cerevisiae*" indicates *Saccharomyces cerevisiae.*

As a result, it was revealed that the binding of the lectin to the microorganism can be analyzed at the level of a single microorganism by reacting the nucleic acid-labeled lectin with cells of the microorganism and sequencing the nucleic acid bonded to the nucleic acid-labeled lectin with a next generation sequencer.

Experimental Example 15

(Examination of Reactivity of Nucleic Acid-Labeled Lectin 8)

A human iPS cell 201B7 line was differentiated into ectoderm by using a commercially available kit (product name: "STEMdiff SMADi Neural Induction Kit, 2 pack", catalog number: "#08582", STEMCELL Technologies), and the cell was recovered on the 4th day and the 11th day. Subsequently, each plurality of kinds of nucleic acid-labeled lectins was subjected to a reaction, and the binding thereof was analyzed using a next generation sequencer.

Nucleic acid-labeled lectins (SNA, ConA, GSLII, rBC2LCN, rAAL, rABA, rLSLN, rPSL1a, rDiscoidin I, rF17AG, rPVL, rCGL2, rPAIL, rPPL, rRSIIL, rCNL, WFA, HPA, SSA, rOrysata, rPALa, rDiscoidin II, CSA, rGRFT, rSRL, rAOL, rBanana, rBC2LA, rC14, rCalsepa, rGal3C, rGC2, rMalectin, rMOA, rPTL, rRSL, TJAI, TJAII, and, UEAI) prepared in the same manner as in Example 4 were used as the nucleic acid-labeled lectin, and a podocalyxin (PODXL) antibody was used.

First, each aliquot of 100,000 cells of each cell was suspended in 100 μL of BSA-PBS and dispensed into a tube. Subsequently, 0.5 ng of each nucleic acid-labeled lectin was added to each cell suspension and reacted at 4° C. for 1 hour. Subsequently, the cells were washed 3 times with 1 mL of BSA-PBS and then suspended in 200 μL of BSA-PBS.

Subsequently, 10,000 cells and a single cell were dispensed, the base sequence of the nucleic acid labeled to the nucleic acid-labeled lectin bound to each cell was sequenced using a next generation sequencer (product name: "MiSeq®", Illumina, Inc.), and the number of reads of the detected base sequence was totaled.

Figure 17A:
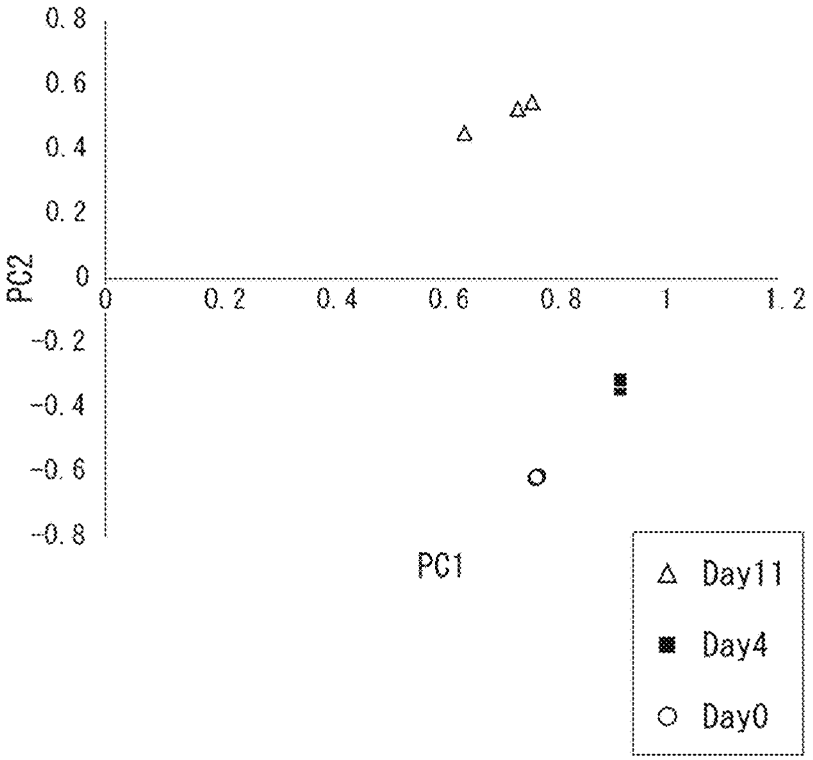
FIG. 17A is a graph showing the results of Experimental Example 15.
Figure 17B:
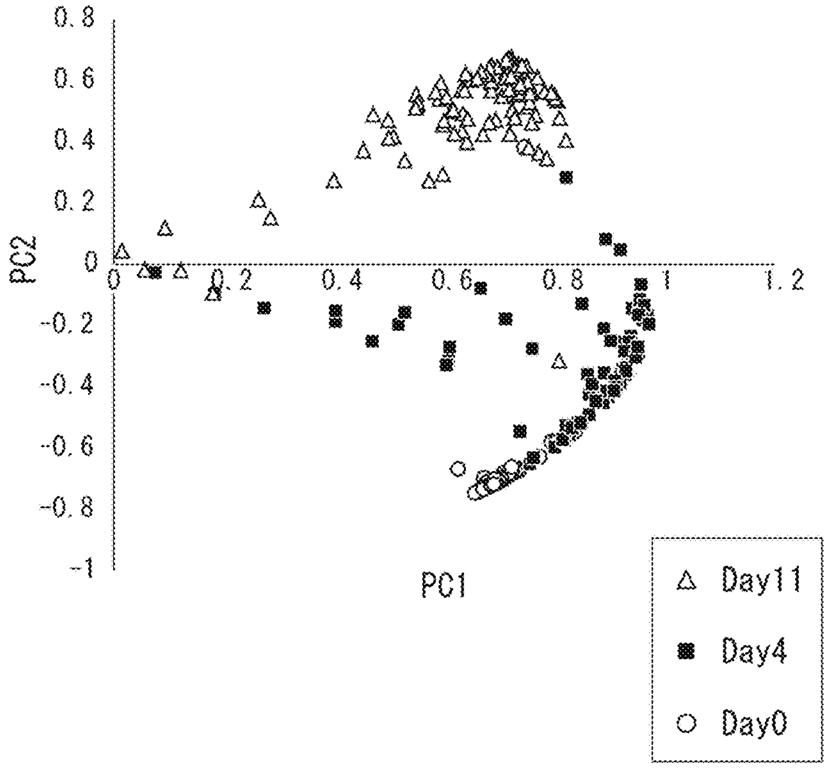
FIG. 17B is a graph showing the results of Experimental Example 15.

FIG. 17A and FIG. 17B are graphs showing the results obtained by subjecting the obtained number of reads to the main component analysis. FIG. 17A shows the results of the analysis at the level of 10,000 cells (the average value, n=3). Further, FIG. 17B shows the results of the analysis at a single cell level (n=3). In FIG. 17A and FIG. 17B, "PC1" indicates a Principal component 1 (a main component 1), and "PC2" indicates a Principal component 2 (a main component 2). In addition, "Day 0" indicates that it is the result of the iPS cell before differentiation induction, "Day 4" indicates that it is the result of the iPS cell on the 4th day after differentiation induction, and "Day 7" indicates that it is the result of the iPS cell on the 7th day after differentiation induction.

As a result, it was revealed that the binding of the lectin to the cell can be analyzed at a single cell level by reacting a mixture of the nucleic acid-labeled lectins with cells and sequencing the nucleic acid bonded to the nucleic acid-labeled lectin with a next generation sequencer. In addition, it was revealed that although the analysis result at a single cell level is similar to the analysis result of 10,000 cells, this cell population has considerably heterogeneous glycans.

In addition, from the analysis results at the level of 10,000 cells, it was revealed that the glycan structure changes with the elapse of time after the induction of differentiation. In addition, from the analysis results at a single cell level, it was revealed that although the iPS cell is a relatively homogeneous cell population, it becomes a cell population having various glycans after the induction of differentiation.

This result further supports that the glycan of individual cells constituting a cell population can be analyzed at a single cell level.

Experimental Example 16

(Analysis of a Cell Surface Glycan and RNA in Cell at a Single Cell Level 1)

Each aliquot of 100,000 cells of a human iPS cell 201B7 line was suspended in 100 μL of BSA-PBS and dispensed into a tube. Subsequently, 0.5 ng of each nucleic acid-labeled lectin was added to each cell suspension and reacted at 4° C. for 1 hour. Subsequently, the cells were washed 3 times with 1 mL of BSA-PBS and then suspended in 200 μL of BSA-PBS.

Subsequently, an ultraviolet (UV) irradiation device (catalog number: "95-0042-14", Funakoshi Co., Ltd.) was used to carry out irradiation with ultraviolet rays having a peak wavelength at a wavelength of 365 nm at 15 W for 15 minutes and to release the oligonucleotide from the nucleic acid-labeled lectin, thereby recovering the supernatant after centrifugation. Subsequently, a PCR reaction was carried out using this as a template, and the analysis was carried out using a next generation sequencer.

In addition, a cDNA library was prepared from the total RNA of a single cell precipitated after centrifugation by using GenNext® RamDA-seq™ Single Cell Kit (Toyobo Co., Ltd.).

Subsequently, the sample was treated using Nextera® XT DNA Sample Preparation Kit (Illumina, Inc.) and then sequenced using a next generation sequencer (product name: "MiSeq®" "MiSeq", Illumina, Inc.), and the number of reads of the detected base sequence was totaled.

Figure 18A:
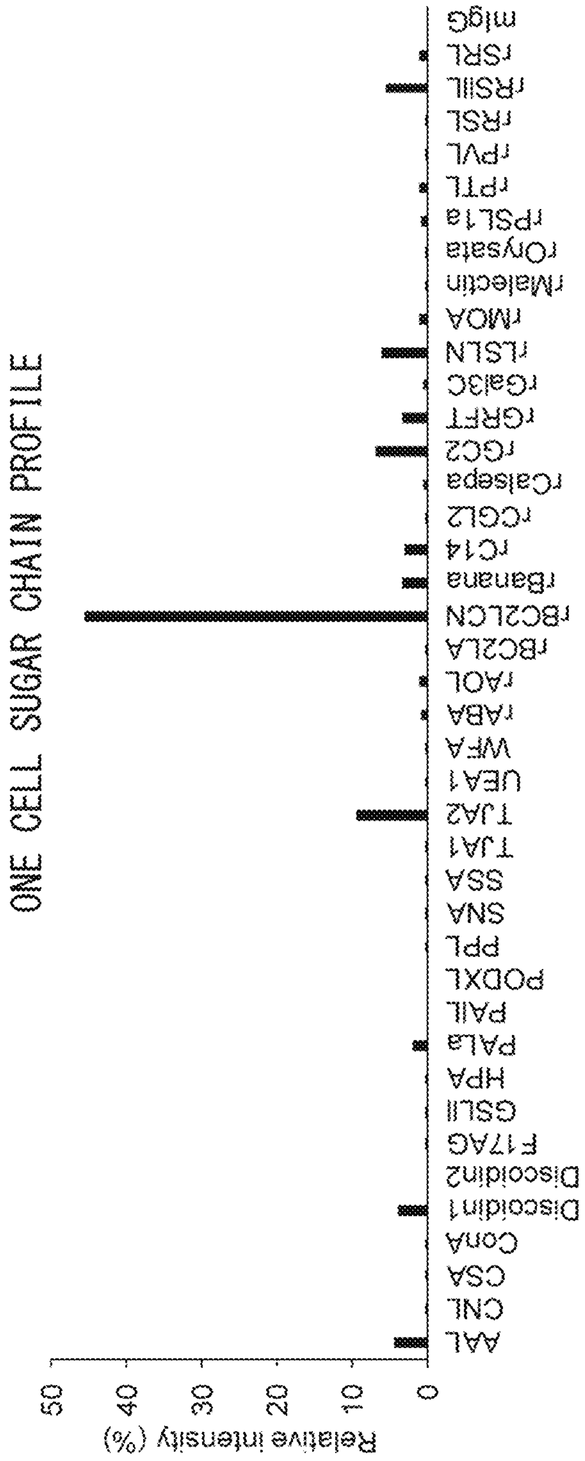
FIG. 18A is a graph showing representative results obtained by analyzing a cell surface glycan and RNA in cells at a single cell level in Experimental Example 16.
Figure 18B:
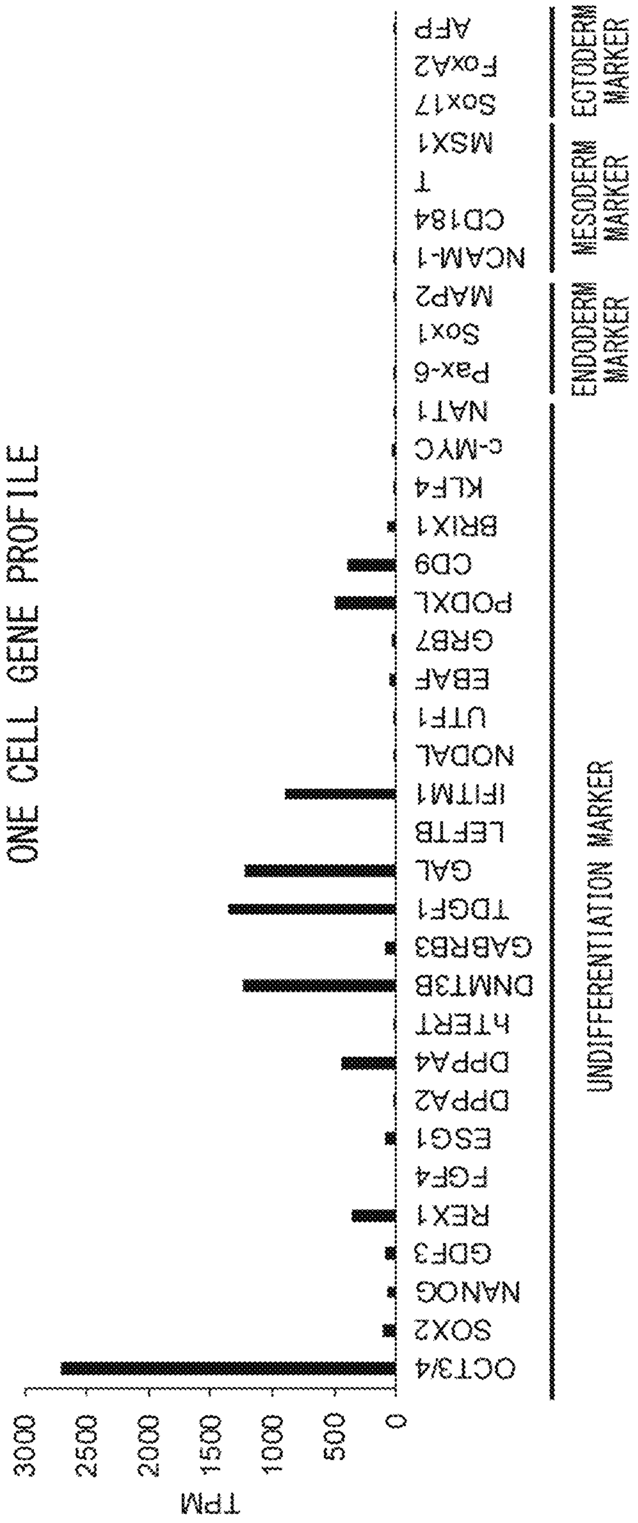
FIG. 18B is a graph showing representative results obtained by analyzing a cell surface glycan and RNA in cells at a single cell level in Experimental Example 16.

FIG. 18A and FIG. 18B are graphs showing representative results obtained by analyzing a cell surface glycan and RNA in cells at a single cell level. FIG. 18A is the results of the glycan profile, and FIG. 18B is the results of the gene profile. In FIG. 18A, the vertical axis indicates the signal intensity (the relative value), and the lateral axis indicates the kind of lectin. Further, in FIG. 18B, the vertical axis indicates transcripts per million (TPM), and the lateral axis indicates the gene name of each marker gene of the undifferentiation marker, endoderm marker, mesoderm marker, and ectoderm marker.

As a result, it was revealed that RNA information as well as glycan information on the cell surface can be obtained from a single cell.

Experimental Example 17

(Analysis of a Cell Surface Glycan and RNA in Cell at a Single Cell Level 2)

The human iPS cell 201B7 line was differentiated into ectoderm (nerve), and the cell surface glycan on the 0th day and 11th day and the RNA in the cell were analyzed at a single cell level.

Specifically, first, the human iPS cell 201B7 line was differentiated into ectoderm (nerve) by using a commercially available kit (product name: "STEMdiff SMADi Neural Induction Kit, 2 pack", catalog number: "#08582", STEMCELL Technologies), and the cell was recovered on the 0th day and the 11th day.

Subsequently, each plurality of kinds of nucleic acid-labeled lectins was reacted with each recovered cell, and the binding thereof was analyzed using a next generation sequencer. Nucleic acid-labeled lectins (SNA, ConA, GSLII, rBC2LCN, rAAL, rABA, rLSLN, rPSL1a, rDiscoidin I, rF17AG, rPVL, rCGL2, rPAIL, rPPL, rRSIIL, rCNL, WFA, HPA, SSA, rOrysata, rPALa, rDiscoidin II, CSA, rGRFT, rSRL, rAOL, rBanana, rBC2LA, rC14, rCalsepa, rGal3C, rGC2, rMalectin, rMOA, rPTL, rRSL, TJAI, TJAII, and, UEAI) prepared in the same manner as in Example 4 were used as the nucleic acid-labeled lectin, and a podocalyxin (PODXL) antibody was used.

Each aliquot of 100,000 cells of each cell was suspended in 100 μL of BSA-PBS and dispensed into a tube. Subsequently, 0.5 ng of each nucleic acid-labeled lectin was added to each cell suspension and reacted at 4° C. for 1 hour. Subsequently, the cells were washed 3 times with 1 mL of BSA-PBS and then suspended in 200 μL of BSA-PBS.

Subsequently, cells were dispensed to a single cell, and an ultraviolet (UV) irradiation device (catalog number: "95-0042-14", Funakoshi Co., Ltd.) was used to carry out irradiation with ultraviolet rays having a peak wavelength at a wavelength of 365 nm at 15 W for 15 minutes and to release the oligonucleotide from the nucleic acid-labeled lectin, thereby recovering the supernatant after centrifugation. Subsequently, a PCR reaction was carried out using the recovered supernatant as a template, the PCR product was sequenced using a next generation sequencer (product name: "MiSeq®", Illumina, Inc.), and the number of reads of the detected base sequence was totaled.

In addition, a cDNA library was prepared from the total RNA of a single cell precipitated after centrifugation by using GenNext® RamDA-seq™ Single Cell Kit (Toyobo Co., Ltd.).

Subsequently, the sample was treated using Nextera XT DNA Sample Preparation Kit (Illumina, Inc.) and then sequenced using a next generation sequencer (product name: "NovaSeq 6000", Illumina, Inc.), and the quality of the raw data was checked using FastQC v0.11.7 (https://www.bioinformatics.babraham.ac.uk/projects/fastqc/).

Then, trimming was carried out with Trimmomatic 0.38 (http://www.usadellab.org/cms/?page=trimmomatic), and mapping to the genome was carried out using HISAT2 v2.1.0 (http://daehwankimlab.github.io/hisat2/) and Bowtie2 2.3.5.1 (https://sourceforge.net/projects/bowtie-bio/files/bowtie2/2.3.5.1/). Further, mapping to the transcript was carried out using StringTie v1.3.4d (https://ccb.jhu.edu/software/stringtie/).

Figure 19A:
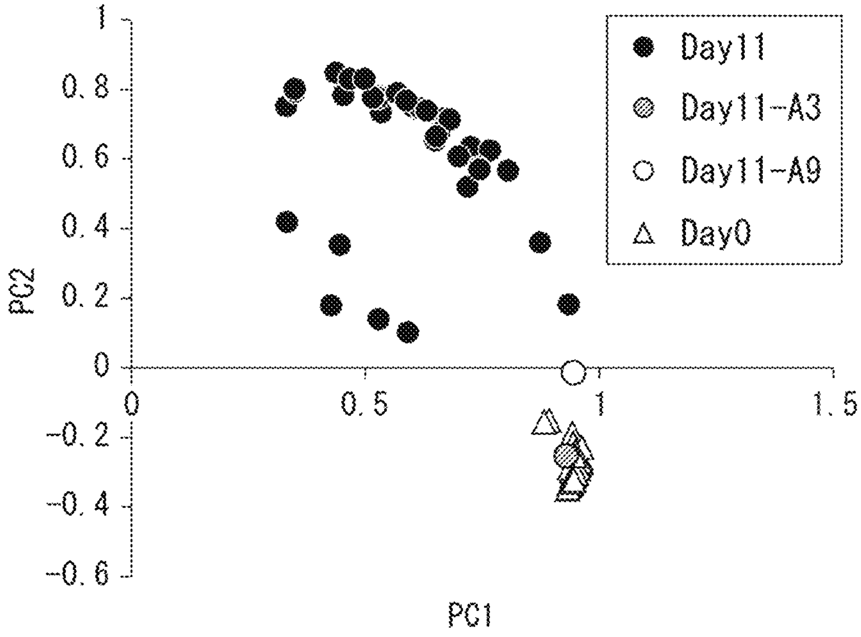
FIG. 19A is a graph showing the results obtained by subjecting the glycan profile of iPS cells induced to differentiate into the nerve to the main component analysis in Experimental Example 17.

FIG. 19A is a graph showing the results obtained by subjecting the obtained glycan profile to main component analysis. As a result, it was revealed that the heterogeneity of the glycan profile is increased in the cell on the 11th day after differentiation induction as compared with the cell on the 0th day.

Subsequently, the expression of the neural differentiation marker OTX2 gene and the undifferentiated marker POU5F1 gene was checked in each of the cells of Day11-A3 and Day11-A9, which showed a glycan profile close to that on the 0th day.

Figure 19B:
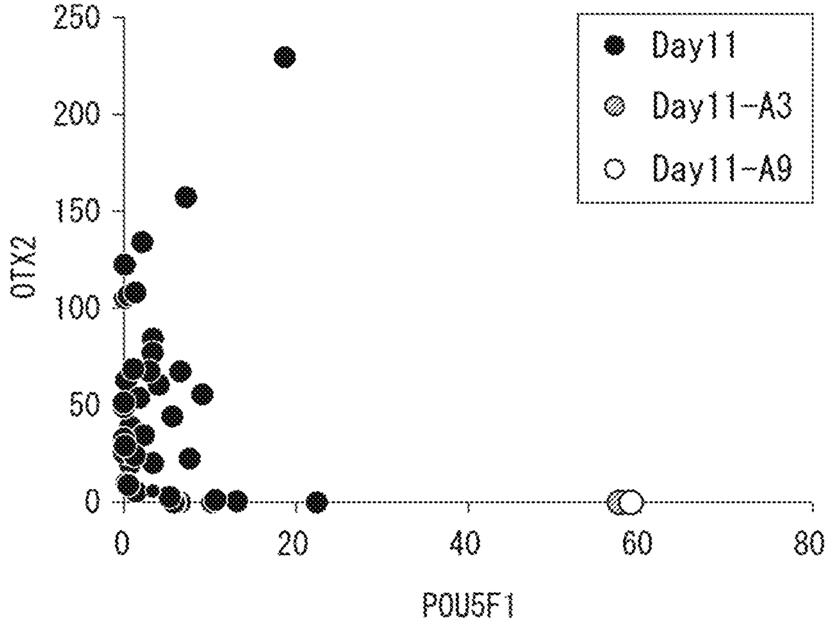
FIG. 19B is a graph showing the results obtained by analyzing the expression level of marker genes of iPS cells induced to differentiate into the nerve in Experimental Example 17.

FIG. 19B is a graph showing the results obtained by analyzing the expression level of each marker gene. As a result, it was revealed that the expression of the neural differentiation marker is low and the expression of the undifferentiation marker is high in each of the cells of Day11-A3 and Day11-A9. That is, it was revealed that these cells are in an undifferentiated state without being induced to differentiate even on the 11th day after differentiation induction to ectoderm (nerve).

Figure 20A:
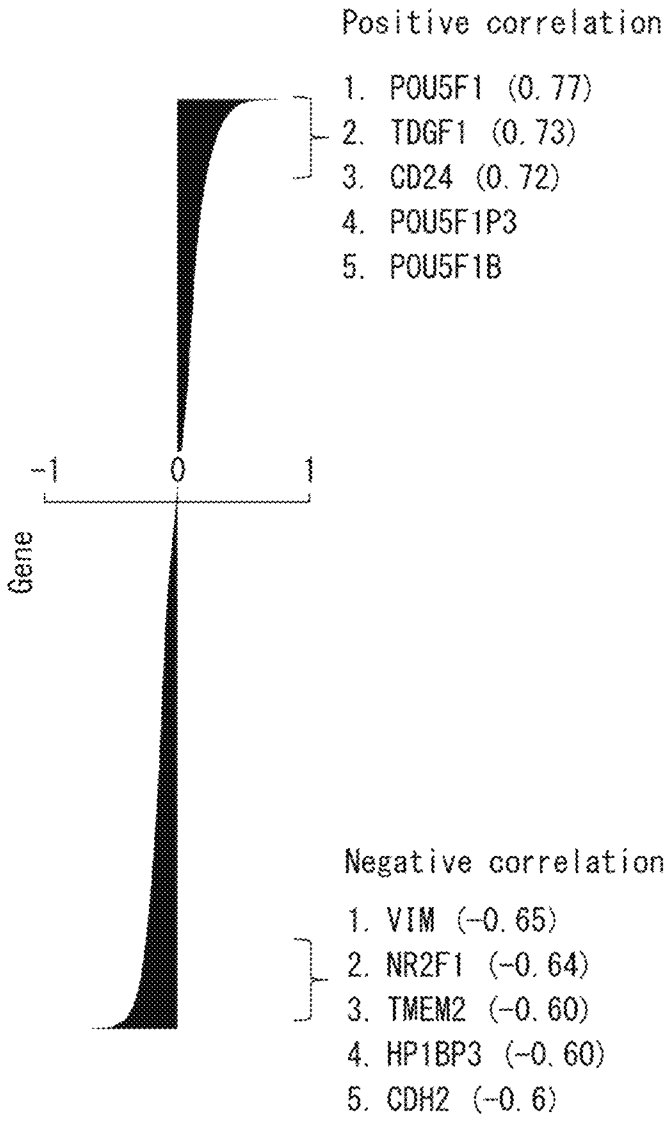
FIG. 20A is a graph showing the results of calculating the correlation coefficient between the amount of the rBC2LCN lectin bound to human iPS cells and the expression level of a group of 27,686 genes and arranging them in descending order of numerical values in Experimental Example 17.

FIG. 20A is a graph showing the results of calculating the correlation coefficient between the amount of the rBC2LCN lectin bound to each cell, where the rBC2LCN lectin specifically binds to the human iPS cell, and the expression level of a group of 27,686 genes, and arranging them in descending order of numerical values.

As a result, it was revealed that the gene showing the highest positive correlation is the undifferentiation marker POU5F1. On the other hand, it was revealed that the gene showing the highest negative correlation is the neural differentiation marker VIM.

Figure 20B:
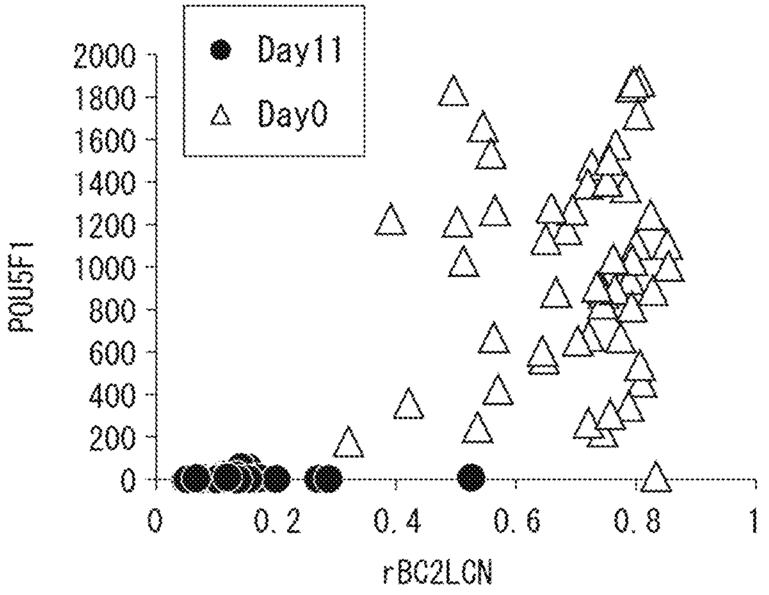
FIG. 20B is a scatter plot showing the amount of the rBC2LCN lectin bound to each cell and the expression level of the POU5F1 gene expression level in each cell in Experimental Example 17.
Figure 20C:
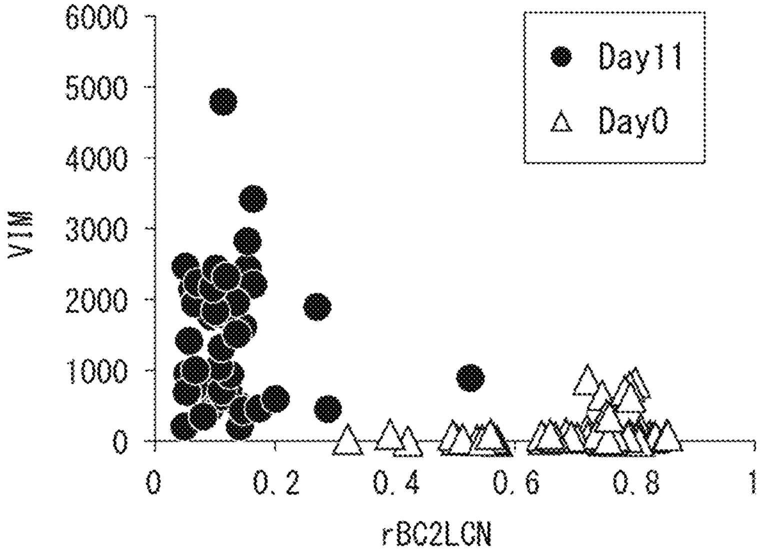
FIG. 20C is a scatter plot showing the amount of the rBC2LCN lectin bound to each cell and the expression level of the VIM gene expression level in each cell in Experimental Example 17.

FIG. 20B is a scatter plot showing the amount of the rBC2LCN lectin bound to each cell and the expression level of the undifferentiation marker POU5F1 gene. FIG. 20C is a scatter plot showing the amount of the rBC2LCN lectin bound to each cell and the expression level of the neural differentiation marker VIM gene.

As a result, it was revealed that the binding amount of the rBC2LCN lectin shows a positive correlation with the expression level of the POU5F1 gene and shows a negative correlation with the expression level of the VIM gene. That is, it was revealed that the rBC2LCN lectin binds to a cell in which the expression of the undifferentiation marker POU5F1 gene is high and the expression of the neural differentiation marker VIM gene is low.

Figure 21A:
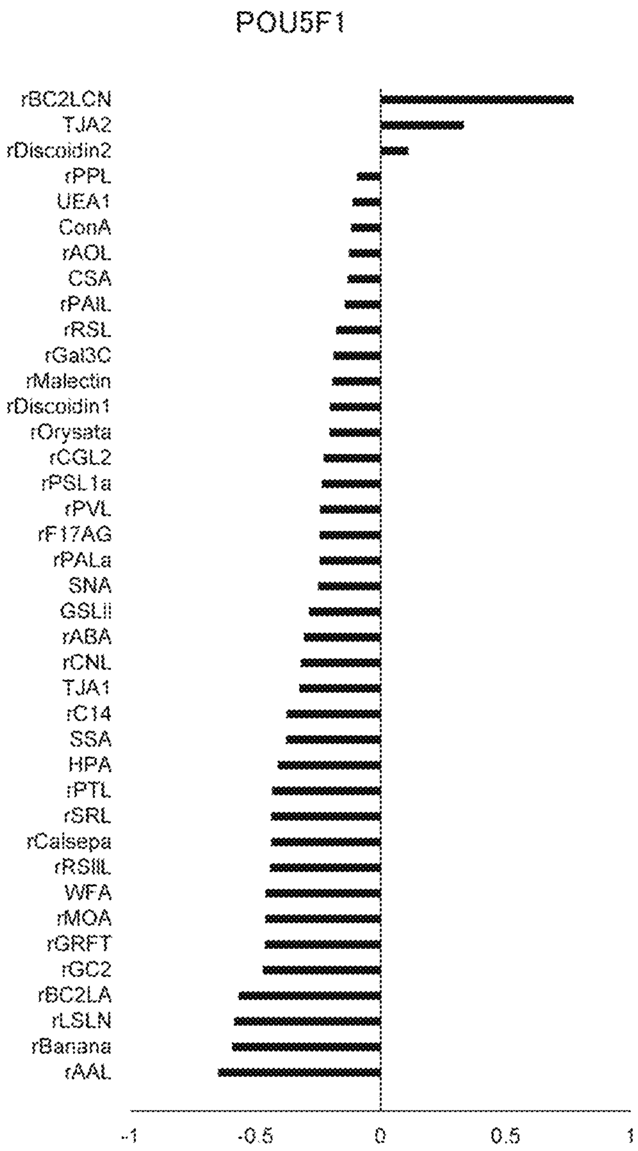
FIG. 21A is a graph in which the correlation coefficient between the expression level of the POU5F1 gene in each cell and the binding amount of 39 kinds of lectins is calculated and arranged in descending order in Experimental Example 17.
Figure 21B:
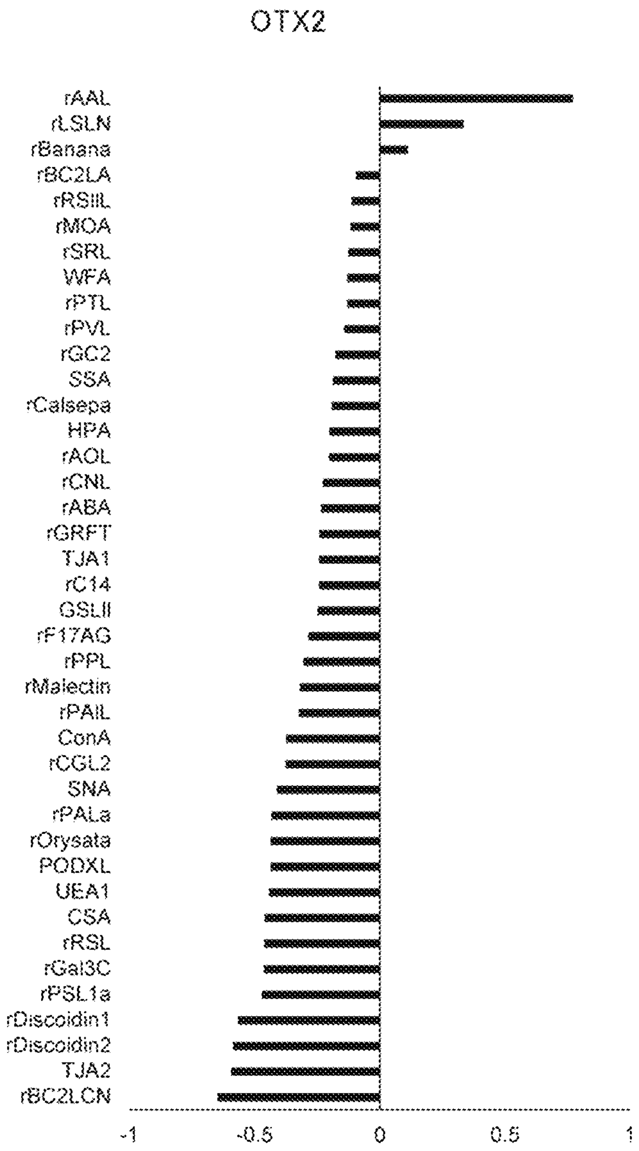
FIG. 21B is a graph in which the correlation coefficient between the expression level of the OTX2 gene in each cell and the binding amount of 39 kinds of lectins is calculated and arranged in descending order in Experimental Example 17.

FIG. 21A is a graph in which the correlation coefficient between the expression level of the undifferentiation marker POU5F1 gene in each cell and the binding amount of 39 kinds of lectins is calculated and arranged in descending order. In addition, FIG. 21B is a graph in which the correlation coefficient between the expression level of the neural differentiation marker OTX2 gene in each cell and the binding amount of 39 kinds of lectins is calculated and arranged in descending order.

As a result, it was revealed that the lectin showing the highest positive correlation coefficient with respect to the expression level of the undifferentiation marker POU5F1 gene is rBC2LCN. In addition, it was revealed that the lectin showing the highest positive correlation coefficient with respect to the expression level of the neural differentiation marker OTX2 gene is rAAL. That is, it was conceivable that rAAL may show significantly high reactivity to nerve cells after differentiation induction as compared with human iPS cells.

From the above results, it was shown that according to the method of the present experimental example, it is possible to simultaneously measure glycans and genes, which are expressed in heterogeneous and diverse cell populations at a single cell level, and further, it is possible to reveal the relationship between the expressed glycans and the expressed genes from the obtained data, at a single cell level.

INDUSTRIAL APPLICABILITY

According to the present invention, it is possible to provide a novel technique for analyzing a glycan.

The invention claimed is:

1. A method for analyzing at least one cell, the method comprising:

preparing a mix of glycan-binding substances for analyzing glycans on a surface of subject cells, each glycan-binding substance of the mix of glycan-binding substances being labeled with a respective nucleic acid, each nucleic acid having a specific base sequence which specifies the glycan-binding substance, and corresponds to a kind of glycan, the mix including ten or more kinds of glycan-binding substances;

bringing the mix into contact with the subject cells in a solution, whereby a bound portion of the mix binds to the glycans of the subject cells while an unbound portion of the mix remains in the solution;

removing the unbound portion of the mix from the solution;

isolating a single cell from the subject cells after the steps of bringing and removing, the subject cells and the single cell being alive during the step of isolating;

detecting the nucleic acids labeled on glycan-binding substances that are associated with the single cell; and determining glycan profile of the single cell that is alive based on the detected nucleic acids and their quantities as indicators of kinds and quantities of the glycans on the surface of the single cell.

2. The method according to claim 1, further comprising:

analyzing a phenotype of the single cell or RNA information in the single cell, together with the glycan.

3. The method according to claim 1, wherein the step of bringing is carried out in a buffer solution containing albumin.

4. The method according to claim 1, wherein the step of detection is carried in a state where the glycan-binding substances each labeled with the nucleic acid are bound to the single cell.

5. The method according to claim 1, wherein the mix of glycan-binding substances recognizes at least sialic acid (Sia), N-acetyl-glucosamine (GlcNAc), mannose (Man), D-galactose (Gal), N-acetyl-galactosamine (GalNAc), and L-fucose (Fuc), which are monosaccharides constituting the glycans on the surface of the subject cells.

6. The method according to claim 5, further comprising, before the step of detecting, amplifying the nucleic acids relating to the single cell by PCR.

7. The method according to claim 1, wherein the kinds and quantities of the glycans of the single cell represents the glycome of a living cell.

8. The method according to claim 1, wherein the mix of glycan-binding substances is a mix of lectins.

9. The method according to claim 1, wherein:

in the step of preparing, each of the glycan-binding substances is bound to the respective nucleic acid via a cleavable spacer, after the step of isolating, the method further comprises detaching the nucleic acids from the glycan-binding substances using the cleavable spacer, and collecting the nucleic acids relating to the single cell from the solution, and the step of detecting is carried out using the collected portion of nucleic acids.

10. A method for analyzing at least one cell, the method comprising:

preparing a mix of glycan-binding substances for analyzing glycans on a surface of cells, each of the glycan-binding substances being labeled with a respective nucleic acid, each nucleic acid having a specific base sequence that specifies the glycan-binding substance and corresponds to a kind of glycan, the mix including ten or more kinds of glycan-binding substances;

contacting the mix with subject cells that are alive in a solution, whereby a portion of the mix binds to the glycans of the subject cells while a remaining portion of the mix remains unbound in the solution;

washing away the remaining portion of the mix;

isolating a single cell from the subject cells after the steps of contacting and washing;

detecting nucleic acids labeled on glycan-binding substances that are associated with the single cell and RNA information in the single cell, wherein the detected nucleic acids and their quantities correspond to kinds and quantities of the glycans on the surface of the single cell that is alive; and obtaining a set of data of the kinds and quantities of the glycans and expressed genes of the RNA information for the single cell.

11. The method according to claim 10, wherein the step of detection is carried in a state where the glycan-binding substances each labeled with the nucleic acid are bound to the single cell.

12. The method according to claim 10, wherein the RNA information in the single cell is a base sequence information or an expression level information on mRNA in the single cell.

* * * * *